US009833411B2

(12) United States Patent
Vrettos et al.

(10) Patent No.: US 9,833,411 B2
(45) Date of Patent: Dec. 5, 2017

(54) SOLID ORAL DOSAGE FORMS

(71) Applicant: Enteris Biopharma, Inc., Boonton, NJ (US)

(72) Inventors: John Vrettos, Union, NJ (US); Thomas Daggs, Verona, NJ (US); Paul Shields, North Caldwell, NJ (US); Raymundo Claudio, Lincoln Park, NJ (US)

(73) Assignee: Enteris BioPharma, Inc., Boonton, NJ (US)

( * ) Notice: Subject to any disclaimer, the term of this patent is extended or adjusted under 35 U.S.C. 154(b) by 0 days.

(21) Appl. No.: 14/993,294

(22) Filed: Jan. 12, 2016

(65) Prior Publication Data

US 2016/0199303 A1    Jul. 14, 2016

Related U.S. Application Data

(60) Provisional application No. 62/102,263, filed on Jan. 12, 2015.

(51) Int. Cl.
| | | |
|---|---|---|
| *A61K 9/20* | (2006.01) | |
| *A61K 38/09* | (2006.01) | |
| *A61K 31/00* | (2006.01) | |
| *A61K 47/69* | (2017.01) | |

(52) U.S. Cl.
CPC ............ *A61K 9/2054* (2013.01); *A61K 9/205* (2013.01); *A61K 9/2013* (2013.01); *A61K 9/2031* (2013.01); *A61K 31/00* (2013.01); *A61K 38/09* (2013.01); *A61K 47/6903* (2017.08)

(58) Field of Classification Search
CPC ...... A61K 31/00; A61K 9/0053; A61K 9/146; A61K 9/2013; A61K 9/28; A61K 9/205
See application file for complete search history.

(56) References Cited

U.S. PATENT DOCUMENTS

| | | | |
|---|---|---|---|
| 2,956,926 A * | 10/1960 | Greif ........................ | A61K 9/50 252/384 |
| 4,708,934 A | 11/1987 | Gilligan et al. | |
| 4,751,284 A | 6/1988 | Forsmann | |
| 4,849,227 A | 7/1989 | Cho | |
| 5,087,613 A | 2/1992 | Courtney et al. | |
| 5,433,940 A | 7/1995 | Maraganore et al. | |
| 5,789,234 A | 8/1998 | Bertelsen et al. | |
| 5,912,014 A | 6/1999 | Stern et al. | |
| 5,929,027 A | 7/1999 | Takama | |
| 6,086,918 A | 7/2000 | Stern et al. | |
| 6,103,495 A | 8/2000 | Mehta et al. | |
| 6,210,925 B1 | 4/2001 | Mehta et al. | |
| 6,248,717 B1 | 6/2001 | Carpino et al. | |
| 6,268,343 B1 | 7/2001 | Knudsen et al. | |
| 6,384,016 B1 | 5/2002 | Kaarsholm | |
| 6,440,392 B1 | 8/2002 | Stern | |
| 6,627,438 B2 | 9/2003 | Mehta et al. | |
| 6,673,574 B2 | 1/2004 | Stern et al. | |
| 6,737,250 B2 | 5/2004 | Mehta et al. | |
| 7,235,627 B2 | 6/2007 | Knudsen et al. | |
| 7,316,819 B2 | 1/2008 | Crotts et al. | |
| 7,445,911 B2 | 11/2008 | Consalvo et al. | |
| RE40,812 E | 6/2009 | Stern | |
| 7,553,655 B2 | 6/2009 | Mehta et al. | |
| 7,595,293 B2 | 9/2009 | Engelund et al. | |
| 7,666,446 B2 | 2/2010 | Choi et al. | |
| 7,968,311 B2 | 6/2011 | Mehta et al. | |
| 8,088,734 B2 | 1/2012 | Mehta et al. | |
| 8,093,207 B2 | 1/2012 | Stern et al. | |
| 8,097,698 B2 | 1/2012 | Knudsen et al. | |
| 8,163,871 B2 | 4/2012 | Consalvo et al. | |
| 8,216,822 B2 | 7/2012 | Mehta et al. | |
| 8,227,241 B2 | 7/2012 | Mehta et al. | |
| RE43,580 E | 8/2012 | Stern | |
| 8,252,580 B2 | 8/2012 | Mehta et al. | |
| 8,377,863 B2 | 2/2013 | Stern et al. | |
| 8,513,183 B2 | 8/2013 | Stern et al. | |
| 8,592,366 B2 | 11/2013 | Stern et al. | |
| 8,664,178 B2 | 3/2014 | Stern et al. | |
| 8,815,583 B2 | 8/2014 | Miller et al. | |
| 8,835,161 B2 | 9/2014 | Mehta et al. | |
| 8,835,377 B2 | 9/2014 | Mehta et al. | |
| 9,278,123 B2 | 3/2016 | Sauerberg et al. | |
| 9,399,017 B2 | 7/2016 | Stern et al. | |
| 2001/0055648 A1 | 12/2001 | Lee et al. | |

(Continued)

FOREIGN PATENT DOCUMENTS

| | | |
|---|---|---|
| CA | 2070061 | 2/2004 |
| EP | 308067 | 3/1978 |

(Continued)

OTHER PUBLICATIONS

Kagatani et al (Pharmaceutical Research, 1996, vol. 13, pp. 739-743).*
Bastin et al., "Salt Selection and Optimisation Procedures for Pharmaceutical New Chemical Entities", Organic Process Research & Development 2000, vol. 4, No. 5, pp. 427-435.
Mehta, Nozer M., "Oral Delivery and Recombinant Production of Peptide Hormones, Part II: Recombinant Production of Therapeutic Peptides", Biopharm International, Jul. 2004, pp. 44-46.
Ray et al., "Production of Salmon Calcitonin by Direct Expression of a Glycine-Extended Precursor in *Escherichia coli*", Protein Expresion & Purification 26 2002, pp. 249-259.
Ray et al., "Production of Recombinant Salmon Calcitonin by In Vitro Amidation of an *Escherichia coli* Produced Precursor Peptide", Biotechnology vol. 11, Jan. 1993, pp. 64-70.

(Continued)

*Primary Examiner* — Mark V Stevens
(74) *Attorney, Agent, or Firm* — Greenberg Traurig, LLP; David J. Dykeman; Natalie Salem

(57) ABSTRACT

The present invention provides pharmaceutical compositions suitable for oral delivery of active agent, such as peptides and small molecules, and methods for treating subjects in need thereof. The pharmaceutical compositions of the present invention enhance the bioavailability of therapeutic active agents.

17 Claims, 28 Drawing Sheets

(56) References Cited

U.S. PATENT DOCUMENTS

| | | |
|---|---|---|
| 2003/0017203 A1* | 1/2003 | Crotts ............. A61K 9/2086 424/477 |
| 2004/0197323 A1 | 10/2004 | Mehta et al. |
| 2005/0112206 A1* | 5/2005 | Watanabe ........... A61K 9/2027 424/487 |
| 2005/0123507 A1 | 6/2005 | Ameri et al. |
| 2005/0215476 A1 | 9/2005 | Mehta et al. |
| 2005/0282756 A1 | 12/2005 | Mehta et al. |
| 2006/0127995 A1 | 6/2006 | Consalvo et al. |
| 2006/0199763 A1 | 9/2006 | Knudsen et al. |
| 2006/0247167 A1 | 11/2006 | Schlein et al. |
| 2006/0270603 A1 | 11/2006 | Mehta et al. |
| 2006/0292672 A1 | 12/2006 | Miller et al. |
| 2007/0134279 A1 | 6/2007 | Stern |
| 2007/0243244 A1 | 10/2007 | Shah et al. |
| 2008/0125361 A1 | 5/2008 | Ludvigsen et al. |
| 2009/0011976 A1 | 1/2009 | Ludvigsen et al. |
| 2009/0060861 A1 | 3/2009 | Poulsen |
| 2009/0317462 A1 | 12/2009 | Stern et al. |
| 2010/0239667 A1* | 9/2010 | Hemmingsen ....... A61K 9/2072 424/466 |
| 2010/0256060 A1 | 10/2010 | Stern |
| 2011/0045029 A1 | 2/2011 | Choi et al. |
| 2012/0040000 A1 | 2/2012 | Stern et al. |
| 2012/0071410 A1 | 3/2012 | Mehta et al. |
| 2012/0315325 A1 | 12/2012 | Stern et al. |
| 2013/0034600 A1 | 2/2013 | Stern et al. |
| 2013/0072446 A1 | 3/2013 | Consalvo et al. |
| 2013/0171248 A1 | 7/2013 | Choi et al. |
| 2013/0345134 A1 | 12/2013 | Sauerberg et al. |
| 2014/0004198 A1 | 1/2014 | Balschmidt et al. |
| 2014/0045754 A1 | 2/2014 | Drustrup et al. |
| 2014/0249085 A1 | 9/2014 | Mehta et al. |
| 2014/0255479 A1 | 9/2014 | Carl et al. |
| 2014/0335169 A1 | 11/2014 | Stern et al. |
| 2015/0031606 A1 | 1/2015 | Vilhelmsen |
| 2015/0125522 A1 | 5/2015 | Mehta et al. |
| 2015/0150811 A1 | 6/2015 | Jensen et al. |
| 2015/0273069 A1 | 10/2015 | Bjerregaard et al. |
| 2016/0067184 A1 | 3/2016 | Nielsen et al. |
| 2016/0106814 A1 | 4/2016 | Rasmussen et al. |
| 2016/0151462 A1 | 6/2016 | Sauerberg et al. |
| 2016/0296624 A1 | 10/2016 | Carl et al. |

FOREIGN PATENT DOCUMENTS

| | | |
|---|---|---|
| EP | 382403 | 8/1990 |
| EP | 517211 | 12/1992 |
| WO | 1997/033531 | 9/1997 |
| WO | 1998/046722 | 10/1998 |
| WO | 2001/056594 | 8/2001 |
| WO | 2002/043767 | 6/2002 |
| WO | 2002/072075 | 9/2002 |
| WO | 2002/087621 | 11/2002 |
| WO | 2004/064758 | 8/2004 |
| WO | 2005/089182 | 9/2005 |
| WO | 2006/026592 | 3/2006 |
| WO | 2006051103 A2 | 5/2006 |
| WO | 2006/058225 | 6/2006 |
| WO | 2007/002532 | 1/2007 |
| WO | 2007/070450 | 6/2007 |
| WO | 2008/150426 | 12/2008 |
| WO | 2012080471 A1 | 6/2012 |
| WO | 2012098188 A1 | 7/2012 |
| WO | 2012/174117 | 12/2012 |
| WO | 2012/174397 | 12/2012 |
| WO | 2013139695 A1 | 9/2013 |
| WO | 2013189988 A1 | 12/2013 |
| WO | 2014060472 A1 | 4/2014 |
| WO | 2014177683 A1 | 6/2014 |
| WO | 2014/138241 | 9/2014 |
| WO | 2014191545 A1 | 12/2014 |
| WO | 2015162195 A1 | 10/2015 |
| WO | 2016120380 A1 | 1/2016 |
| WO | 2016120378 A1 | 8/2016 |

OTHER PUBLICATIONS

International Search Report and Written Opinion issued in International Application No. PCT/US2016/012970 dated Apr. 22, 2016.
Constantinides, P. et al., "Considerations and recommendations on traditional and non-traditional uses of excipients in oral drug products", AAPS Open 2:3, pp. 1-6 (May 10, 2016).

* cited by examiner

SOLID ORAL DOSAGE FORMS

CROSS-REFERENCE TO RELATED APPLICATIONS

This application claims priority to, and the benefit of, U.S. provisional Application No. 62/102,263, filed Jan. 12, 2015, the content of which is incorporated herein by reference in its entirety.

FIELD OF THE INVENTION

The present invention relates to compositions for the oral delivery of pharmacologically active agents, particularly for the delivery of a peptide or small molecule active agent.

BACKGROUND

Oral delivery of active pharmaceutical ingredients is generally the delivery route of choice since it is convenient, relatively easy and generally painless, resulting in greater patient compliance relative to other modes of delivery. However, effective oral delivery of active pharmaceutical ingredients, such as peptides or small molecules, can be challenging because of the pre-systemic degradation of the API, poor permeability across the intestinal epithelium, low solubility, and varying pH in the gastrointestinal tract, thereby leading to low or erratic bioavailability. There is a need for oral formulations that are capable of providing suitable bioavailability of administered peptides and small molecule agents.

SUMMARY

Solid oral dosage forms are disclosed herein. According to some aspects, disclosed herein are solid oral dosage forms that include a therapeutically effective amount of an active pharmaceutical ingredient, such as a peptide, hormone or a small molecule. Such oral dosage forms are designed to be released in a suitable part of the GI tract to achieve maximal systemic bioavailability to treat or prevent a disease in a subject in need thereof.

According to some aspects, disclosed herein are modified release solid oral compositions. In some embodiments, the modified release solid dosage composition comprise (a) a core comprising (i) an effective amount of active pharmaceutical ingredient, (ii) a pH lowering agent, (iii) an absorption enhancer, (iv) a filler comprising an hydrogel-forming polymer, and (v) less than 10% by weight of disintegrant; and (b) an enteric coating surrounding the core, the composition providing a pharmacokinetic profile for the active agent with a $T_{lag}$ greater than 1.0 h and less than 16 h post-administration and a $T_{max}$ greater than ($T_{lag}$+0.5 h) and less than 20 h post-administration.

In some embodiments, the pharmacokinetic release profile targets release of the pharmaceutical active ingredient to the jejunum, the ileum or the jejunum and the ileum. In some embodiments, the composition is designed so that substantially no active pharmaceutical ingredient is released in the stomach, the duodenum or the stomach and duodenum post-administration.

In some embodiments, the composition further comprises a water soluble barrier beneath the enteric coating. In some embodiments, the water soluble barrier is in amount from about 6% to about 15% by weight. In some embodiments, the water soluble barrier can be polyvinylpyrrolidone, hydroxymethylcellulose, hydroxypropylcellulose, methylcellulose or combinations thereof.

In some embodiments, the absorption enhancer has a critical micelle concentration of from about 1.0 mM to about 40 mM or of from about 1.0 mM to about 15 mM.

In some embodiments, the hydrogel-forming polymer has a viscosity of about 3,000 to about 120,000 cP at 20° C. In some embodiments, the hydrogel-forming polymer comprises hydroxypropylcellulose, hydroxypropylmethylcellulose or a combination thereof. In some embodiments, the filler comprises microcrystalline cellulose, hydroxypropylcellulose, hydroxypropylmethylcellulose, chitosan or a combination thereof.

In some embodiments, the active pharmaceutical ingredient comprises a peptide and/or a peptidomimetic. In some embodiments, the peptide can be leuprolide, insulin, vasopressin, calcitonin, calcitonin gene-related peptide, parathyroid hormone, desmopressin, gonadotrophin releasing hormone (GnRH), luteinizing hormone-releasing factor, erythropoietin, tissue plasminogen activators, human growth hormone, adrenocorticotropin, interleukins, enkephalin, glucagon-like peptide-1, desmopressin, 2,6-dimethyltyrosine-D-arginine-phenylalanine-lysine amide or analogs thereof or combinations thereof.

In some embodiments, the active pharmaceutical ingredient comprises a small molecule. In some embodiments, the small molecule is classified as BCS Class II, BCS Class III or BCS Class IV. In some embodiments, the small molecule can be tigecycline, zanamivir, kanamycin, tobramycin, fenofibrate or combinations thereof.

In some embodiments, the absorption enhancer comprises a cationic surface active agent, an anionic surface active agent or a combination thereof. In some embodiments, the cationic surface active agent comprises an acylcarnitine. In some embodiments, the anionic surface active agent comprises sodium dodecyl sulfate. In some embodiments, the absorption enhancer comprises sodium dodecyl sulfate.

In some embodiments, the pH lowering agent comprises citric acid, tartaric acid or a combination thereof. In some embodiments, the pH lowering agent is in the form of coated acid particles. In some embodiments, the acid particles are coated with a water-soluble coating. In some embodiments, the pH lowering agent is in the form of coated citric acid particles. In some embodiments, the composition comprises from about 50 mg to about 500 mg of citric acid. In some embodiments, the composition comprises from about 250 mg to about 500 mg of citric acid. In some embodiments, the citric acid is in the form of coated citric acid.

In some embodiments, the composition comprises from about 5 mg/cm² to about 25 mg/cm² of enteric coating.

In some aspects, the modified release solid oral composition comprises (a) a core comprising (i) an effective amount of active pharmaceutical ingredient, (ii) a pH lowering agent, (iii) an absorption enhancer, (iv) a filler comprising an hydrogel-forming polymer, wherein the core is substantially free of disintegrant, and (b) an enteric coating surrounding the core, the composition providing a pharmacokinetic profile for the active agent with a $T_{lag}$ greater than 1.0 h and less than 16 h post-administration and a $T_{max}$ greater than ($T_{lag}$+0.5 h) and less than 20 h post-administration.

In some embodiments, the pharmacokinetic release profile targets release of the pharmaceutical active ingredient to the jejunum, the ileum or the jejunum and the ileum. In some embodiments, the composition is designed so that substantially no active pharmaceutical ingredient is released in the stomach, the duodenum or the stomach and duodenum post-administration.

In some embodiments, the composition further comprises a water soluble barrier beneath the enteric coating. In some embodiments, the water soluble barrier is in amount from about 6% to about 15% by weight. In some embodiments, the water soluble barrier can be polyvinylpyrrolidone, hydroxymethylcellulose, hydroxypropylcellulose, methylcellulose and combinations thereof.

In some embodiments, the absorption enhancer has a critical micelle concentration of from about 1.0 to about 40 mM or of from about 1.0 to about 15 mM.

In some embodiments, the hydrogel-forming polymer has a viscosity of about 3,000 to about 120,000 cP at 20° C. In some embodiments, the hydrogel-forming polymer comprises hydroxypropylcellulose, hydroxypropylmethylcellulose or a combination thereof. In some embodiments, the filler comprises microcrystalline cellulose, hydroxypropylcellulose, hydroxypropylmethylcellulose, chitosan or a combination thereof.

In some embodiments, the active pharmaceutical ingredient comprises a peptide and/or a peptidomimetic. In some embodiments, the peptide can be leuprolide, insulin, vasopressin, calcitonin, calcitonin gene-related peptide, parathyroid hormone, desmopressin, gonadotrophin releasing hormone (GnRH), luteinizing hormone-releasing factor, erythropoietin, tissue plasminogen activators, human growth hormone, adrenocorticotropin, interleukins, enkephalin, glucagon-like peptide-1, desmopressin, 2,6-dimethyltyrosine-D-arginine-phenylalanine-lysine amide or analogs thereof or combinations thereof.

In some embodiments, the active pharmaceutical ingredient comprises a small molecule. In some embodiments, the small molecule is classified as BCS Class II, BCS Class III or BCS Class IV. In some embodiments, the small molecule can be tigecycline, zanamivir, kanamycin, tobramycin, fenofibrate or a combination thereof.

In some embodiments, the absorption enhancer comprises a cationic surface active agent, an anionic surface active agent or a combination thereof. In some embodiments, the cationic surface active agent comprises an acylcarnitine. In some embodiments, the anionic surface active agent comprises sodium dodecyl sulfate. In some embodiments, the absorption enhancer comprises sodium dodecyl sulfate.

In some embodiments, the pH lowering agent comprises citric acid, tartaric acid or a combination thereof. In some embodiments, the pH lowering agent is in the form of coated acid particles. In some embodiments, the acid particles are coated with a water-soluble coating. In some embodiments, the pH lowering agent is in the form of coated citric acid particles. In some embodiments, the composition comprises from about 50 mg to about 500 mg of citric acid. In some embodiments, the composition comprises from about 250 mg to about 500 mg of citric acid. In some embodiments, the citric acid is in the form of coated citric acid.

In some embodiments, the composition comprises from about 5 mg/cm$^2$ to about 25 mg/cm$^2$ of enteric coating.

According to aspects illustrated herein, there is disclosed a method of increasing plasma concentration of an active pharmaceutical ingredient, such as a peptide, hormone or a small molecule that includes orally administering to a subject in need thereof a pharmaceutical composition of the present disclosure.

Some aspects relate to methods of treating a patient are disclosed. In some embodiments, the method of treating comprises (a) providing a solid oral dosage form comprising (i) a core comprising an effective amount of active pharmaceutical ingredient, a pH lowering agent, an absorption enhancer, a filler comprising an hydrogel-forming polymer, and less than 10% by weight of disintegrant; and (ii) an enteric coating surrounding the core; and (b) administering orally to a patient, the solid oral dosage form, wherein the solid oral dosage form provides a pharmacokinetic release profile for the active agent with a $T_{lag}$ greater than 1.0 h and less than 16 h post-administration and a $T_{max}$ greater than ($T_{lag}$+0.5 h) and less than 20 h post-administration.

In some embodiments, the pharmacokinetic release profile targets release of the pharmaceutical active ingredient to the jejunum, the ileum or the jejunum and the ileum.

In some embodiments, the solid oral dosage form is substantially free of disintegrant. In some embodiments, the solid oral dosage form further comprises a water soluble barrier beneath the enteric coating.

In some embodiments, the absorption enhancer has a critical micelle concentration of from about 1.0 to about 40 mM. In some embodiments, the absorption enhancer has a critical micelle concentration of from about 1.0 to about 15 mM.

In some embodiments, the hydrogel-forming polymer has a viscosity of about 3,000 to about 120,000 cP at 20° C. In some embodiments, the filler comprises microcrystalline cellulose, hydroxypropyl cellulose, hydroxypropyl methyl cellulose, chitosan or a combination thereof. In some embodiments, the hydrogel-forming polymer comprises hydroxypropyl cellulose, hydroxypropyl methyl cellulose or a combination thereof.

In some embodiments, the active pharmaceutical ingredient comprises a peptide or a peptidomimetic. In some embodiments, the peptide is one of leuprolide, insulin, vasopressin, calcitonin, calcitonin gene-related peptide, parathyroid hormone, desmopressin, gonadotrophin releasing hormone (GnRH), luteinizing hormone-releasing factor, erythropoietin, tissue plasminogen activators, human growth hormone, adrenocorticotropin, interleukins, enkephalin, glucagon-like peptide-1, desmopressin, 2,6-dimethyltyrosine-D-arginine-phenylalanine-lysine amide and analogs thereof.

In some embodiments, the active pharmaceutical ingredient comprises a small molecule. In some embodiments, the small molecule is classified as BCS Class II, BCS Class III or BCS Class IV. In some embodiments, the small molecule is one of tigecycline, zanamivir, kanamycin, tobramycin and fenofibrate.

In some embodiments, the absorption enhancer comprises a cationic surface active agent, an anionic surface active agent or a combination thereof. In some embodiments, the cationic surface active agent comprises an acylcarnitine. In some embodiments, the anionic surface active agent comprises sodium dodecyl sulfate. In some embodiments, the absorption enhancer comprises sodium dodecyl sulfate.

In some embodiments, the pH lowering agent comprises citric acid, tartaric acid or a combination thereof. In some embodiments, the pH lowering agent is in the form of coated acid particles. In some embodiments, the acid particles are coated with a water-soluble coating. In some embodiments, the pH lowering agent is in the form of coated citric acid particles. In some embodiments, the composition comprises from about 50 mg to about 500 mg of citric acid. In some embodiments, the composition comprises from about 250 mg to about 500 mg of citric acid. In some embodiments, the citric acid is in the form of coated citric acid.

In some embodiments, the composition comprises from about 5 mg/cm$^2$ to about 25 mg/cm$^2$ of enteric coating.

These and other aspects of the present invention will become apparent upon reference to the following detailed description.

BRIEF DESCRIPTION OF THE DRAWINGS

The present invention will be further explained with reference to the attached drawings.

Figure 1:
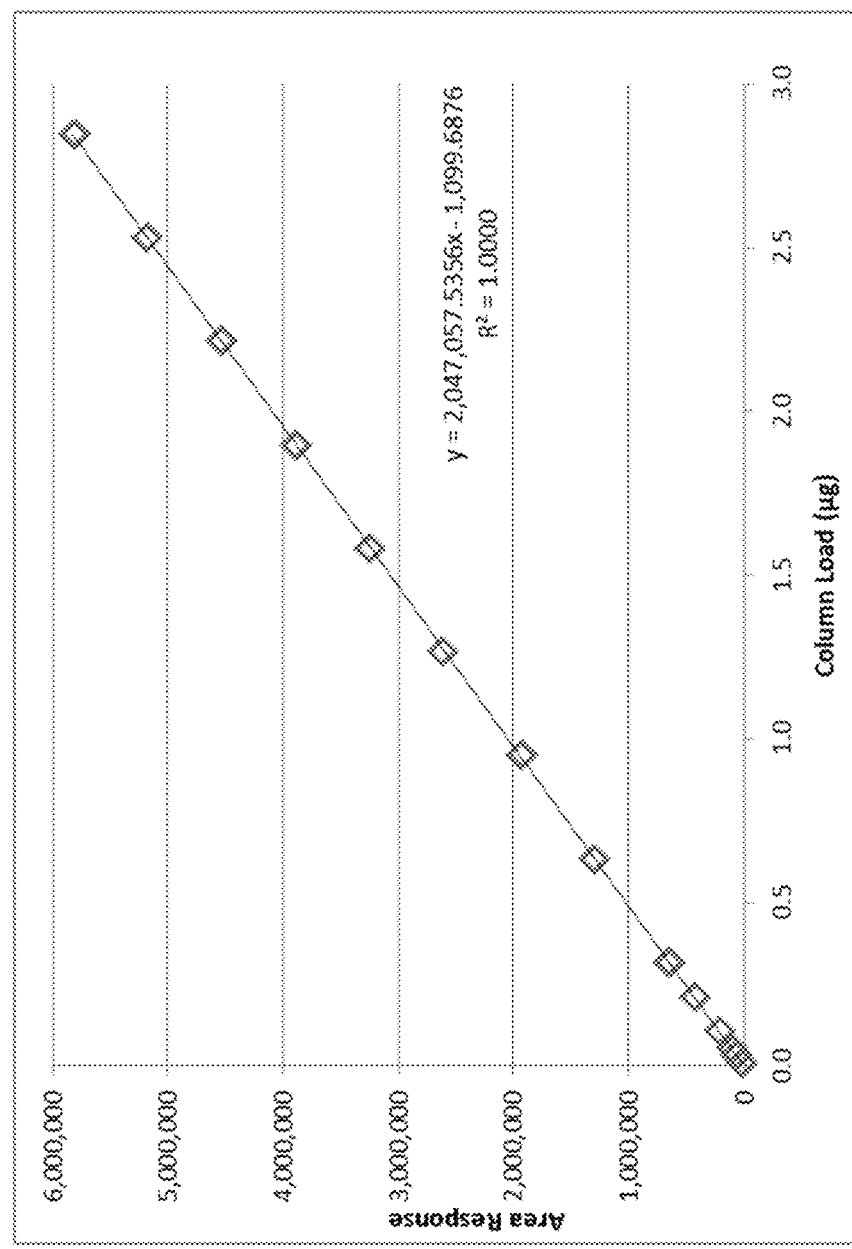
FIG. 1 shows a linearity curve (RP-HPLC) for leuprolide.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed invention.

DETAILED DESCRIPTION

It is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Pharmaceutical Compositions

As used herein, the terms "formulation" and "composition" are used interchangeably and refer to a mixture of two or more compounds, elements, or molecules. In some aspects the terms "formulation" and "composition" may be used to refer to a mixture of one or more active agents with a pH lowering agent, an absorption enhancer or other excipients. All references to residence times in the gastrointestinal tract (GIT) assume a fasted state. All references to bioavailability (% F) denote absolute bioavailability (relative to intravenous injection), unless otherwise stated.

The terms "API", "active agent" and "drug" are used interchangeably herein to refer to a therapeutically, and/or prophylactically active compound that has physiologic, pharmaceutical, pharmacological, or therapeutic effect. The term is intended to include the API in any suitable form such as e.g. a pharmaceutically acceptable salt, complex, solvate or prodrug thereof of or, if relevant, in any stereoisomer form including any enantiomeric or racemic form, or a combination of any of the above. Examples of API include, but are not limited to, a hormone, a peptide, a small molecule or prodrug thereof.

As used herein, the terms "dosage form" and "pharmaceutical composition" are used interchangeably herein to refer to physically discrete units suitable as unitary dosages for human subjects and other mammals, each unit containing a predetermined quantity of therapeutic agent calculated to produce the desired onset, tolerability, and therapeutic effects, in association with one or more suitable pharmaceutical excipients. Methods for preparing such dosage forms are known or will be apparent to those skilled in the art. The dosage forms of the present invention may take the form of tablets, pills, capsules, or the like. In some embodiments, the dosage form is a tablet. In other embodiments, the dosage form is a capsule.

As used herein, an "effective amount" or a "therapeutically effective amount" of an API refers to a non-toxic, but sufficient amount of the API, to achieve therapeutic results in treating a condition for which the API is known to be effective. It is understood that various biological factors may affect the ability of a substance to perform its intended task.

Numerous human hormones, neurotransmitters, and other important biological compounds have peptides as a substantial part of their molecular structures. Many diseases respond positively to raising the level of these peptide compounds in patients. Other therapeutically active agents, such as small molecule active agents are actively pursued to complement the therapeutic advances made with peptide based drugs. Therapeutically effective amounts of such biologically relevant therapeutically active agents may be administered to patients in a variety of ways, for example, by the oral route.

Delivering therapeutically active peptides and small molecules by the oral route has been a challenge and a goal for many decades. Some of the challenges include, but are not limited to, digestive enzymes and strongly acidic environment of the stomach, intestinal digestive enzymes, components of pancreatic juices and secretions of the biliary system, and composition and thickness of outer and inner mucus layers of the intestine. Furthermore, the compositions and concentrations of intestinal components are not uniform, but vary within the segments of the intestine (duodenum, jejunum, ileum, colon). All of these factors, and more, are chemical and physical hurdles to the oral delivery of peptides and small molecules into systemic circulation. For examples, proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima).

The problem of the oral delivery of pharmaceutically active peptides and small molecules is further confounded by the fact that different peptides and small molecules may have different physical-chemical properties, such as: net charge, solubility, hydrophobicity, molecular weight, and for the peptides, protease sensitivity, and others. Thus, there is a need to control key aspects of the dosage form to enable oral delivery of active agents, with maximal bioavailability.

One skilled in the art will appreciate that, to increase efficiency and systemic bioavailability, the dosage form should deliver the active agent (e.g. peptide or small molecule), and any absorption-enhancing agents, to the part of the gastrointestinal tract best suited chemically and physically for absorption of that particular active agent.

Aspects of the invention provide for pharmaceutical compositions (e.g. oral dosage forms) that enable the location and rate of release of the active agent and enhancing excipients from the pharmaceutical compositions in the gastrointestinal (GI) tract. In some embodiments, the dosage form comprises a core (comprising the API) and an enteric coat wherein the core, the coat or the core and the coat are designed to be released in a suitable part of the GI tract to achieve maximal systemic bioavailability to treat or prevent a disease in a subject in need thereof.

Aspects of the invention relate to an oral delivery dosage from that can precisely target a therapeutically active agent beyond the duodenum without prematurely delivering drugs to the upper GI tract. The compositions according to the invention have delayed-release forms controlled by an enteric coating and, in some embodiments, the tablet core dissolution rate, and can reach beyond the distal part of the duodenum such as the jejunum and/or ileum and/or colon. Such oral dosage forms can be advantageous in a number of ways. In some embodiments, such dosage forms can be used to minimize degradation and absorption through the upper GI tract and maximize the amount of therapeutically active agent delivered beyond the duodenum, for example, in the jejunum, ileum or colon. For peptide and small molecule drugs, such oral dosage forms can be used to maximize overall systemic absorption of these active agents. As one skilled in the art will appreciate, by avoiding exposure of the protein or peptide active agents to the upper GI tract, intraluminal degradation and breakdown of the peptide active agents can be minimized to a large extent.

One of the conventional formulation principles was to make a tablet which dissolved as rapidly as possible after passage through the stomach. That principle was derived, in part, from the expectation that a very fast, concentrated release of the drug and enhancers as a concentrated bolus in the duodenum would result in the highest absorption and that variability would be reduced as a consequence of those higher overall bioavailabilities. The experimental data described herein, however, showed an unexpected and surprising trend in that the solid oral dosage form (e.g. tablet) which was slowest to open and dissolve showed the greatest active agent absorption with the most precise individual absorptions. While the rapidly dissolving formulation can have a highest individual absorption, the average and median % F values can be lower and less precise, when compared to the slow dissolution dosage form. Without being bound by the theory, the experimental data suggest that a longer lag time before dissolution, might moderate the extreme high and low absorption values commonly observed with conventional and more rapidly dissolving tablets.

In some embodiments, the acid-resistant coat thickness, the coat's buffer capacity, the composition of the core, or a combination thereof can be used to maximize the systemic bioavailability of the active agent by controlling key attributes of the dosage form, specifically:

1. $T_{lag}$—the time delay between oral dose administration and the first measurable concentration of the active agent in systemic circulation 2. $T_{max}$—the time at which the maximum concentration of API ($C_{max}$) is in systemic circulation 3. The chemical nature of the permeation enhancer employed, specifically, the critical micelle concentration (CMC). The CMC is the concentration below which the surface tension of the aqueous phase remains linearly dependent of the concentration of surfactant, and at which the surfactant solution equilibrium favors surfactant monomers vs. micelles. Thus, free surfactant is available in solution to interact with the API and/or GIT.

In some embodiments, the dosage forms are designed to ensure that the active ingredients (e.g. API, absorption enhancer(s)) are released prior to entering the colon, based on the typical ranges of GIT transit times in humans. Absorption in the colon is very limited, the water content is low (which may retard dissolution of the tablet), and the dosage form may become entrapped in fecal matter and so be physically unable to deliver the API and enhancers.

In some aspects, the $T_{lag}$ is higher (e.g. at least about 0.5 h higher) than dosage forms having a conventional core and/or enteric coating. In some aspects, the $T_{max}$ is greater than ($T_{lag}$+0.5 h). In some embodiments, (a) the $T_{lag}$ of the solid oral dosage form is about 1.0 h, or greater than about 1.0 h, and less than about 16 h post-administration; and (b) the $T_{max}$ is greater than $T_{lag}$+0.5 h and less than 20 h post-administration. In some embodiments, the $T_{lag}$ of the solid oral dosage greater than 1.5 h and less than about 16 h. In some embodiments, the $T_{lag}$ of the solid oral dosage greater than 2.0 h and less than about 16 h. In some embodiments, the $T_{max}$ is greater $T_{lag}$+1.0 h and less than 20 h post-administration. In some embodiments, the $T_{max}$ is greater $T_{lag}$+1.5 h and less than 20 h post-administration. In some embodiments, the $T_{max}$ is greater $T_{lag}$+2.0 h and less than 20 h post-administration. In some embodiments, (a) the $T_{lag}$ of the solid oral dosage form is greater than about 1.0 h, and less than about 16 h post-administration; and (b) the $T_{max}$ is greater 1.5 h and less than 20 h post-administration. In some embodiments, (a) the $T_{lag}$ of the solid oral dosage form is greater than about 1.0 h, and less than about 16 h post-administration; and (b) the $T_{max}$ is greater 2 h and less than 20 h post-administration. In some embodiments, (a) the $T_{lag}$ of the solid oral dosage form is greater than about 1.0 h, and less than about 16 h post-administration; and (b) the $T_{max}$ is greater 3 h and less than 20 h post-administration. In some embodiments, (a) the $T_{lag}$ of the solid oral dosage form is greater than about 1.5 h, and less than about 16 h post-administration; and (b) the $T_{max}$ is greater 2 h and less than 20 h post-administration. In some embodiments, (a) the $T_{lag}$ of the solid oral dosage form is greater than about 1.5 h, and less than about 16 h post-administration; and (b) the $T_{max}$ is greater 2.5 h and less than 20 h post-administration. In some embodiments, (a) the $T_{lag}$ of the solid oral dosage form is greater than about 1.5 h, and less than about 16 h post-administration; and (b) the $T_{max}$ is greater 3 h and less than 20 h post-administration. In some embodiments, (a) the $T_{lag}$ of the solid oral dosage form is greater than about 2.0 h, and less than about 16 h post-administration; and (b) the $T_{max}$ is greater 2.5 h and less than 20 h post-administration. In some embodiments, (a) the $T_{lag}$ of the solid oral dosage form is greater than about 2.0 h, and less than about 16 h post-administration; and (b) the $T_{max}$ is greater 3.0 h and less than 20 h post-administration. In some embodiments, (a) the $T_{lag}$ of the solid oral dosage form is greater than about 2.0 h, and less than about 16 h post-administration; and (b) the $T_{max}$ is greater 3.5 h and less than 20 h post-administration. In some embodiments, (a) the $T_{lag}$ of the solid oral dosage form is greater than about 2.0 h, and less than about 16 h post-administration; and (b) the $T_{max}$ is greater 4.0 h and less than 20 h post-administration.

Without being bound to the theory, the widths of these ranges can be necessary to allow for the release of the API and absorption enhancers in the appropriate segment of the intestine best suited to absorb a particular API (which can depend on the physical and chemical nature of the API itself).

Enteric Coat

In some embodiments, the solid dosage form can comprise an enteric coat surrounding the core of the dosage form. In some embodiments, the enteric coat can comprise polymers having pH-dependent release properties and lag time properties (delayed-release). In some embodiments, the dissolution profiles of the solid oral dosage form (e.g. tablets) can have a suitable enteric coat film layer thickness resulting in high average systemic bioavailability with improved precision. In some embodiments, the dosage form comprises from about 5 mg/cm$^2$ to 25 mg/cm$^2$ of an enteric coating. In some embodiments, the dosage form comprises from about 10 mg/cm$^2$ to 25 mg/cm$^2$ of an enteric coating. In some embodiments, the dosage form comprises from about 15 mg/cm$^2$ to 25 mg/cm$^2$ of an enteric coating. In some embodiments, the dosage form comprises from about 20 mg/cm$^2$ to 25 mg/cm$^2$ of an enteric coating. In some embodiments, the dosage form comprises from about 5 mg/cm$^2$ to 20 mg/cm$^2$ of an enteric coating. In some embodiments, the dosage form comprises from about 5 mg/cm$^2$ to about 15 mg/cm$^2$ of an enteric coating. In some embodiments, the dosage form comprises from about 5 mg/cm$^2$ to 10 mg/cm$^2$ of an enteric coating. In some embodiments, the solid oral dosage form can have about 15 mg/cm$^2$ enteric coat or an enteric coat corresponding to about 10% weight gain. In some embodiments, the dosage form comprises from about 10 mg/cm$^2$ to 15 mg/cm$^2$ of an enteric coating. In some embodiments, the dosage form comprises from about 10 mg/cm$^2$ to 20 mg/cm$^2$ of an enteric coating. In some embodiments, the dosage form comprises from about 15 mg/cm$^2$ to 20 mg/cm$^2$ of an enteric coating. In some embodiments, the dosage form comprises an enteric coating corresponding to about 7% weight gain. In some embodiments, the dosage form comprises an enteric coating corresponding to about 10% weight gain. In some embodiments, the dosage form comprises an enteric coating corresponding to about 15% weight gain. In some embodiments, the dosage form comprises an enteric coating corresponding to about 20% weight gain. In some embodiments, the dosage form comprises an enteric coating corresponding to about 5% weight gain. In some embodiments, the dosage form comprises from about 15 mg/ cm$^2$ enteric coat or an enteric coat corresponding to about 10% weight gain.

In some embodiments, bioavailabilities between about 1-20% with CVs in the about 50-60%s can be achieved. In some embodiments, bioavailabilities between about 0.1-60% with CVs in the about 10-160% s can be achieved. In some embodiments, bioavailabilities between 10-20% can be achieved. In some embodiments, bioavailabilities between 10-30% can be achieved. In some embodiments, bioavailabilities between 10-40% can be achieved. In some embodiments, bioavailabilities between 10-50% can be achieved. In some embodiments, bioavailabilities between 10-60% can be achieved. In some embodiments, bioavailabilities between 1-20% can be achieved. In some embodiments, bioavailabilities between 1-30% can be achieved. In some embodiments, bioavailabilities between 1-40% can be achieved. In some embodiments, bioavailabilities between 1-50% can be achieved. In some embodiments, bioavailabilities between 1-60% can be achieved. In some embodiments, bioavailabilities between 20-30% can be achieved. In some embodiments, bioavailabilities between 20-40% can be achieved. In some embodiments, bioavailabilities between 20-50% can be achieved. In some embodiments, bioavailabilities between 20-60% can be achieved. In some embodiments, bioavailabilities between 30-40% can be achieved. In some embodiments, bioavailabilities between 30-50% can be achieved. In some embodiments, bioavailabilities between 30-60% can be achieved. In some embodiments, bioavailabilities between 40-50% can be achieved. In some embodiments, bioavailabilities between 40-60% can be achieved.

Without being bound by the theory, it is believed that the thickness of the coating material, and thus longer lag time before dissolution, can moderate the extreme high and low absorption values commonly observed with the more lightly coated and therefore more rapidly dissolving tablets.

In some embodiments, the dosage forms can be coated with an acid-resistant enteric coating, which differ in thickness and/or buffer capacity. As used herein, the term "buffer capacity" means the number of equivalents of base required to initiate dissolution of the enteric coat. The lower the pH of the enteric coating, the higher the buffer capacity is and vice-versa. Dosage forms with thick (e.g. about 7 to about 20% w/w) enteric coats and/or enhanced buffer capacity (e.g. pH of about 2.3 to about 4.7) are expected to open later in the gastrointestinal tract, and hence have a larger value of $T_{lag}$ relative to tablets coated with thinner enteric coat and/or decreased buffer capacity (e.g. pH of about 4.8 to about 5.4). In some embodiments, dosage forms with about 10% w/w enteric coats and/or enhanced buffer capacity (e.g. about pH 2.3) are expected to open later in the gastrointestinal tract, and hence have a larger value of $T_{lag}$ relative to tablets coated with thinner (e.g. about 6% w/w) enteric coat and/or decreased buffer capacity (about pH 5.2-5.3).

In some embodiments, the dosage form comprises a mixture of an enteric coat which dissolves at about pH 5.5 and above and of an enteric coat which dissolves at about pH 7.4 and above. In some embodiments, the enteric coat can comprise acrylate copolymers or mixtures thereof. In some embodiments, such mixtures can delay an onset of dissolution further down the small intestine. In some embodiments, the enteric coat can comprises a mixture of Eudragit® FS 30 D and Eudragit® L 30 D-55. EUDRAGIT® FS 30 D is a methyl acrylate, methyl methacrylate and methacrylic acid copolymer, which is soluble at pH above 7.0. Eudragit® L 30 D-55 is a poly(methacrylic acid-co-ethyl acrylate) copolymer which is soluble at pH above 5.5. For example, the enteric coat can comprise a mixture of Eudragit® FS 30 D: Eudragit® L 30 D-55 at a ratio of about 75:25 to 95:5. In some embodiments, the enteric coat can comprise a mixture of Eudragit® FS 30 D: Eudragit® L 30 D-55 at a ratio of about 75:25. In some embodiments, the enteric coat can comprise a mixture of Eudragit® FS 30 D: Eudragit® L 30 D-55 at a ratio of about 80:20. In some embodiments, the enteric coat can comprise a mixture of Eudragit® FS 30 D: Eudragit® L 30 D-55 at a ratio of about 90:10.

Core

Aspects of the invention relate to a dosage form that contains a core comprising an active pharmaceutical agent, at least one pH-lowering agent, at least one permeation enhancer, the core being enveloped by an acid-resistant protective coat and a water-soluble barrier layer. In some embodiments, the dosage form may comprise one or more of fillers, binders, glidants, lubricants, etc. suitable for manufacturing the final dosage form.

In some embodiments, the dosage form comprises an active agent, a pH-lowering agent, and an absorption enhancer. In some embodiments, the cores of the dosage form can include a filler/binder, and can include or be free a disintegrant, in order to vary the rate of release of the peptide and enhancing agents. In other embodiments, the dosage form comprises a small molecule, a pH-lowering agent, and an absorption enhancer. In some embodiments, the cores of the dosage form can include a filler/binder, and can be manufactured with or without a disintegrant, in order to vary the rate of release of the small molecule and enhancing agents.

To achieve delayed dissolution and desired release profile, solid oral dosage form can include one or more of the following: (1) a core having a filler containing a hydrogel-forming polymer (e.g., HPC or HPMC), where a 2% solution of the polymer under standard conditions has a viscosity between 3,000 to 120,000 cP at 20° C.; (2) a core substantially free of disintegrant; (3) an adequate enteric coat film thickness as described herein.

As used herein, the term "substantially" when used in a negative connotation refers to the complete or near complete lack of ingredient, structure characteristic, property, state, or result. For example, a composition that is "substantially free of" disintegrant would either completely lack disintegrant, or so nearly completely lack disintegrant that the effect would be the same as if it completely lacked disintegrant.

In some embodiments, the solid oral dosage form may include a reduced amount of disintegrant. In some embodiments, the solid oral dosage comprises less than 10% wt, less than 9% wt, less than 8% wt, less than 7% wt, less than 6% wt, less than 5% wt, less than 4% wt, less than 3.5% wt, less than 3% wt, less than 2.5% wt, less than 2% wt, less than 1.5% wt, less than 1% wt, less than 0.5% wt, less than 0.01% wt, less than 0.001% wt disintegrant. In some embodiments, the solid oral dosage does not include a tablet disintegrant.

In some embodiments, the solid oral dosage form may include a hydroxypropyl cellulose (HPC) filler, a hydroxypropyl methyl cellulose (HPMC) filler and/or other viscous additive, to slow the disintegration of the tablet core after the coating film layers dissolve.

In some embodiments, the solid oral dosage form may include one or more of the following (1) an enteric coat film layer thickness (about 15 mg/cm$^2$, or approximately 10% weight gain) and (2) a reduced amount of disintegrant or be substantially free of disintegrant, and (3) a viscous additive (e.g., but not limited to, a HPC or a HPMC filler).

In some embodiments, the solid oral dosage form may include (1) a mixture of Eudragit® L 30 D-55 and Eudragit® FS 30 D; (2) a reduced amount of tablet disintegrant or be substantially free of disintegrant, (3) and a viscous additive (e.g., but not limited to, a HPC or a HPMC filler).

In some embodiments, the filler/binder can include one or more of microcrystalline cellulose, hydroxypropyl cellulose, hydroxypropyl methyl cellulose, and chitosan. As one of skilled in art would appreciate, chitosan is polymer with a mucoadhesive effect. In some embodiments, chitosan is present in up to about 10% by weight, up to about 15% by weight, up to about 20% by weight, up to about 25% by weight, up to about 30% by weight, up to about 35% by weight, up to about 40% by weight, so that the formulation becomes mucoadhesive. In some embodiments, the filler/binder can include a filler that do not modify viscosity, but modify the release of the API by other physical and/or chemical interactions (e.g. slow solubility). In some embodiments, the filler/binder can include a pharmaceutically acceptable wax (e.g., carnauba wax), gum (e.g., acacia, guar), alginic acid or salt thereof (e.g., sodium alginate), or hyaluronic acid. A slower release rate from the dosage form is expected to cause a delay in $T_{max}$.

In some embodiments, the filler/binder can include one or more of microcrystalline cellulose, hydroxypropyl cellulose, hydroxypropyl methyl cellulose, chitosan, a pharmaceutically acceptable wax (e.g., carnauba wax), gum (e.g., acacia, guar), alginic acid or salt thereof (e.g., sodium alginate), and hyaluronic acid.

In some embodiments, the dosage forms can contain a permeation enhancer having a high critical micelle concentration (CMC) resulting in stronger surfactant properties. For example, the dosage forms can contain a permeation enhancer having a critical micelle concentration (CMC) of about 1.0 to about 40 mM. In some embodiments, the dosage forms contain a permeation enhancer having a critical micelle concentration (CMC) of about 1.0 to about 15 mM. In some embodiments, the permeation enhancer is sodium dodecyl sulphate SDS or a pharmaceutically acceptable surfactant having similar CMC.

In some embodiments, the dosage forms can be coated with an acid-resistant enteric coating, which different thickness and buffer capacity. Dosage forms with thick (e.g. about 10% w/w to about 20% w/w) enteric coats and/or enhanced buffer capacity (e.g. pH of about 2.3 to about 4.7) are expected to open later in the gastrointestinal tract, and hence have a larger value of $T_{lag}$ relative to tablets coated with thinner (e.g. 6% w/w or lower) enteric coat and/or decreased buffer capacity (pH about 4.8-5.4).

In some embodiments, the systemic bioavailability of the active agent can be modulated by controlling the $T_{lag}$ and $T_{max}$ of the dosage form. In some embodiments, a longer $T_{lag}$ can be achieved by increasing the thickness or buffer capacity of the enteric coat. In some embodiments, a longer $T_{max}$ can be achieved by increasing the viscosity of the tablet core through the use of viscous fillers (HPC, HPMC, chitosan) in the absence of a disintegrant. In some embodiments, a sufficient amount of active agent is included in the dosage form of the invention to achieve a therapeutically relevant level.

In some embodiments, the systemic bioavailability of the active agent can be increased by one or a combination of the following (1) increasing the $T_{lag}$ (the time delay between oral dose administration and the first measurable concentration of the active agent in systemic circulation), (2) increasing $T_{max}$, and/or (3) increasing the surfactant strength of the permeation enhancer.

In some embodiments, $T_{lag}$ can by increased by increasing the thickness and/or the buffer capacity of the enteric coat. In some embodiments, $T_{max}$ can be increased by increasing the viscosity of the core of the dosage from. In some embodiments, the surfactant can comprise a surfactant having CMC of about 1.0 mM to about 40 mM.

Peptides

In some embodiments, the peptide compound is a compound that includes a plurality of amino acids and at least one peptide bond in its molecular structure. In some embodiments, the molecular weight of the peptide compound ranges from about 500 Daltons up to about 10,000 Daltons. In some embodiments, the peptide compound is a peptide hormone or analogue thereof. In some embodiments, the hormone or analogue thereof is selected from a gonadotrophin releasing hormone (GnRH) analogue including, but not limited to, triptorelin, leuprorelin and goserelin. In some embodiments, the hormone analogue is leuprorelin.

Peptide compounds which may benefit from oral delivery in accordance with the present disclosure include any therapeutic agent that is physiologically active and has, as part of its molecular structure, a plurality of amino acids and at least one peptide bond. The terms "polypeptide," "peptide" and "protein" are used interchangeably herein to refer to a polymer of amino acid residues. The terms apply to naturally occurring amino acid polymers as well as amino acid polymers in which one or more amino acid residues are a non-natural amino acid. Additionally, such "polypeptides," "peptides" and "proteins" include amino acid chains of any length, including full length proteins, wherein the amino acid residues are linked by covalent peptide bonds. In some embodiments, the peptides can be cyclic peptides. In some embodiments, the API is a peptidomimetic. As used herein the term "peptidomimetic" refers to a small protein-like chain designed to mimic a peptide.

A "non-natural amino acid" refers to an amino acid that is not one of the 20 common amino acids, namely alanine, cysteine, aspartic acid, glutamic acid, phenylalanine, lysine, histidine, isoleucine, lysine, leucine, methionine, asparagine, proline, glutamine, arginine, serine, threonine, valine, tryptophan, and tyrosine, or pyrolysine or selenocysteine. Other terms that may be used synonymously with the term "non-natural amino acid" is "non-naturally encoded amino acid," "unnatural amino acid," "non-naturally-occurring amino acid." The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids. Non-natural amino acids can include amino acids containing the D-isomer configuration since most proteins are comprised primarily or entirely of amino acids in the L-isomer configuration. Peptides containing non-natural amino acids, such as D-amino acids and those including substituted side chains can exhibit improved stability in the gastrointestinal tract as a result of reduced proteolysis.

In some embodiments, peptides can be distinguished from proteins on the basis of size, and as an arbitrary benchmark can be understood to contain approximately 90 or fewer amino acids. In some embodiments, a peptide of the present disclosure includes fewer than 10 amino acids, such as 9 amino acids. In some embodiments, a peptide of the present disclosure includes between about 10 amino acids and about 90 amino acids. In some embodiments, a peptide of the present disclosure includes between about 15 amino acids and about 85 amino acids. In some embodiments, a peptide of the present disclosure includes between about 20 amino acids and about 80 amino acids. In some embodiments, a peptide of the present disclosure includes between about 25 amino acids and about 75 amino acids. In some embodiments, a peptide of the present disclosure includes between about 30 amino acids and about 70 amino acids. In some embodiments, a peptide of the present disclosure includes between about 35 amino acids and about 65 amino acids. In some embodiments, a peptide of the present disclosure includes between about 40 amino acids and about 60 amino acids. In some embodiments, the molecular weight of the peptide compound ranges from about 1000 Daltons up to about 10,000 Daltons. In some embodiments of the present disclosure, degradation of the active ingredients by protease is suppressed by several mechanisms that would otherwise tend to cleave one or more of the peptide bonds of the active ingredient. In addition to natural amino acids, the amino acids may be D-amino acids or unnatural amino acids, some examples of which are discussed infra. The molecular structure may further include other substituents or modifications. For example, if the peptide active ingredient is salmon calcitonin, the salmon calcitonin may be amidated at its C-terminus. Some peptides may be amidated at locations that are not amidated in nature, or may be otherwise modified.

Peptide active ingredients of the present disclosure include, but are not limited to, leuprolide, insulin, vasopressin, calcitonin, calcitonin gene-related peptide, parathyroid hormone, desmopressin, gonadotrophin releasing hormone (GnRH) or analogs thereof, luteinizing hormone-releasing factor, erythropoietin, tissue plasminogen activators, human growth hormone, adrenocorticotropin, various interleukins, enkephalin, glucagon-like peptide-1 (GLP-1), or analogs thereof, desmopressin (DDAVP), 2,6-dimethyltyrosine-D-arginine-phenylalanine-lysine amide (DMT-DALDA), and peptidomimetics.

In some embodiments, a solid oral dosage form of the present disclosure includes a peptide active ingredient selected from one of the following peptide families: tachykinin peptides, vasoactive intestinal peptides, insulin peptides, pancreatic polypeptide-related peptides, opioid peptides and calcitonin peptides. Non-limiting examples of peptides that are part of the tachykinin peptide family include substance P, kassinin, neurokinin A, eledoisin, and neurokinin B. Non-limiting examples of peptides that are part of the vasoactive intestinal peptide family include vasoactive intestinal peptide (VIP), pituitary adenylate cyclase activating peptide (PACAP), peptide histidine isoleucine 27 (Peptide PHI 27), growth hormone releasing hormone (GHRH) and glucagon. Non-limiting examples of peptides that are part of the insulin peptide family include insulin, insulin-like growth factor and relaxin family peptides. Non-limiting examples of peptides that are part of the pancreatic polypeptide-related peptide family include neuropeptide Y (NPY), peptide YY (PYY), avian pancreatic polypeptide (APP), and pancreatic polypeptide (PPY). Non-limiting examples of peptides that are part of the opioid peptide family include proopiomelanocortin (POMC) peptides, encephalin pentapeptides and prodynorphin peptides. Non-limiting examples of peptides that are part of the calcitonin peptide family include calcitonin and amylin.

In some embodiments, the hormone or analogue thereof is selected from a gonadotrophin releasing hormone (GnRH) analogue including, but not limited to, triptorelin, leuprorelin and goserelin As used herein, the term "leuprolide" refers to leuprorelin or leuprolide acetate. Leuprolide acetate is a synthetic nonapeptide agonist analog of luteinizing hormone-releasing factor. When leuprolide is used, it preferably comprises from about 0.01% (w/w) to about 20.0% (w/w) by weight relative to the total weight of the overall solid oral dosage form (exclusive of any acid-resistant protective coating). In some embodiments, about 0.1% (w/w) to about 15.0% (w/w) of leuprolide is present in the solid oral dosage form (exclusive of any acid-resistant protective coating). In some embodiments, about 1.0% (w/w) to about 10.0% (w/w) of leuprolide is present in the solid oral dosage form (exclusive of any acid-resistant protective coating). Leuprolide acetate is commercially available (for example, from BACHEM, Torrence, Calif).

Small Molecules

Aspects of the invention provide a dosage form suitable for oral delivery including at least one compound classified as BCS Class II, BCS Class III or BCS Class IV.

The Biopharmaceutical Classification System (BCS), originally developed by G. Amidon, separates pharmaceuticals for oral administration into four classes depending on their aqueous solubility and their permeability through the intestinal cell layer. According to the BCS, drug substances are classified as follows: Class I—High Permeability, High Solubility; Class II—High Permeability, Low Solubility; Class III—Low Permeability, High Solubility; and Class IV—Low Permeability, Low Solubility.

The drugs are classified in BCS on the basis of the following parameters: 1. solubility; 2. permeability; and 3. dissolution. The class boundaries for solubility are based on the highest dose strength of an immediate release product. A drug is considered highly soluble when the highest dose strength is soluble in 250 milliliters (ml) or less of aqueous media over the pH range of 1 to 7.5. The class boundaries for permeability are based indirectly on the extent of absorption of a drug substance in humans and directly on the measurement of rates of mass transfer across human intestinal membrane. Alternative non-human systems capable of predicting the drug absorption in humans can be used (such as in vitro culture methods). A drug substance is considered highly permeable when the extent of absorption in humans is determined to be 90% or more of the administered dose based on a mass-balance determination or in comparison to an intravenous dose. The class boundaries for dissolution for an immediate release product to be considered rapidly dissolving is when no less than 85% of the labeled amount of the drug substance dissolves within 30 minutes using a USP Dissolution Apparatus 1 at 100 RPM or Apparatus 2 at 50 RPM in a volume of 900 ml or less in a media of 0.1N HCl or simulated gastric fluid or pH 4.5 buffer and pH 6.8 buffer or simulated intestinal fluid.

As used herein, a compound is considered highly soluble when the highest dose strength is soluble in <250 ml water over a pH range of 1 to 7.5. As used herein, a compound is considered highly permeable when the extent of absorption in humans is determined to be >90% of an administered dose, based on mass-balance or in comparison to an intravenous reference dose. As used herein, a compound is considered to be rapidly dissolving when >85% of the labeled amount of drug substance dissolves within 30 minutes using USP apparatus I or II in a volume of <900 ml buffer solutions.

In some embodiments, the active agent can include a small molecule. As used herein, the term small molecule as used herein refers to a low molecular weight organic, inorganic, or organometallic compound which does not include a peptide bond in its molecular structure. A small molecule may have a molecular weight of less than about 2000 Daltons, less than about 1500 Daltons, less than about 1000 Daltons, or less than about 500 Daltons. A small molecule may have a molecular weight of about 50 to about 500 Daltons, of about 50 to about 1000 Daltons, of about 50 to about 1500 Daltons, or of about 50 to about 2000 Daltons.

In some embodiments, the active agent can be a compound that targets bacterial functions or growth processes, for example an antibiotic. In some embodiments, the antibiotic can be an antibiotic that contains a central four-ring carbocyclic skeleton. In some embodiments, the antibiotic can be a tetracycline or glycylcycline antibiotic. In some embodiments, the antibiotic is tigecycline. The active agent can be capable of binding to a ribosomal subunit of a bacterium. In some embodiments, the active agent can be an antiviral agent or compound and can target a virus or viral particle.

The active agent can be classified as a BCS class II drug, a class III drug, or a BCS class IV drug. Non-limiting examples of BCS class II drugs are: glibenclamide, bicalutamide, ezetimibe, fenofibrate, glipizide, atovaquone, carbamazepine, danazol, griseofulvin, ketoconazole, toglitazone, ibuprofen, nifedipine, nitrofurantoin, phenyloin, sulfamethoxazole, trimethoprim, valproic acid, praziquantel, retinol palmitate, and sulfasalazine. Non-limiting examples of BCS class III drugs are: cimetidine, acyclovir, atenolol, ranitidine, abacavir, captopril, chloramphenicol, codeine, colchicine, dapsone, ergotamine, kanamycin, tobramycin, tigecycline, zanamivir, hydralazine, hydrochlorothiazide, levothyroxine, methyldopa, paracetamol, propylthiouracil, pyrodostigmine, sodium cloxacillin, thiamine, benzidazole, didanosine, ethambutol, ethosuximide, folic acid, nicotinamide, nifurtimox, and salbutamol sulfate. Non-limiting examples of BCS class IV drugs are: hydrochlorothiazide, furosemide, cyclosporin A, itraconazole, indinavir, nelfinavir, ritonavir, saquinavir, nitrofurantoin, albendazole, acetazolamide, azithromycin.

In some aspects of the invention, the active agent is Tigecycline. Tigecycline is the first approved member in a new class of glycylcycline-based tetracycline antibiotics. Tigecycline exhibits activity against a variety of gram-positive and gram-negative bacterial pathogens, many of which are resistant to existing antibiotics—including activity against Methicillin-Resistant Staphylococcus aureus (MRSA), Stenotrophomonas maltophilia, Haemophilus influenzae, and Neisseria gonorrhoeae (with MIC values reported at 2 mcg/mL) and multi-drug resistant strains of Acinetobacter baumannii, as non-limiting examples. Tigecycline is licensed for the treatment of skin and soft tissue infections as well as intra-abdominal infections and has been previously utilized as a lyophilized powder for reconstitution for IV infusion in the hospital setting primarily due to its inherently low innate permeability. Tigecycline's aqueous solubility is approximately 300 mg/mL, its permeability liability makes oral administration a challenge. Known formulations exhibit maximal oral bioavailability % (% F) less than 5%. Commensurate with its high aqueous solubility and poor membrane permeation, tigecycline is not extensively metabolized. The drug is primarily cleared through the biliary route, largely as unchanged drug. In some embodiments, the pharmaceutical composition of the present invention is an improved oral dosage formula of tigecycline. In one aspect, the pharmaceutical composition of the present invention is an oral dosage formula of tigecycline for oral conversion of treatment after a patient's clinical signs have stabilized, indicating control of infection. In one aspect, the oral dosage formulation of tigecycline of the present invention is used to control recurrent infections in patients with no, or minimal hepatic impairment.

In some aspects of the invention, the active agent is tobramycin. In some embodiments, the pharmaceutical composition of the present invention is an improved oral dosage formula of tobramycin. In some embodiments, the pharmaceutical composition comprises from about 50 mg to about 400 mg of tobramycin.

In embodiments in which an absorption enhancer is used, the enhancer, which may be a solubility enhancer and/or transport enhancer (as described in more detail below), aids transport of the peptide agent from the intestine to the blood, and may promote the process so that it better occurs during the time period of reduced intestinal pH and reduced intestinal proteolytic activity. Many surface active agents may act as both solubility enhancers and transport (uptake) enhancers. Again without intending to be bound by theory, it is believed that enhancing solubility desirably provides better solubility of the API in, and transport through, a mucous layer along the intestinal walls. Once the API reaches the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition. In other embodiments, separate absorption enhancers may provide the two functions separately.

Components of solid oral dosage forms of the present disclosure, including optional components, are discussed in separate sections below. Species suggested for each component can be used alone or in combination with other species. For example, combinations of multiple pH-lowering agents, or (where an absorption enhancer is used) multiple enhancers can be used as well as using just a single pH-lowering agent and/or single enhancer. Some preferred combinations are also discussed below. One or more optional components may be included in combination with other optional components.

The pH-Lowering Agent (Acid)

Proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima). Proteolytic degradation of peptides may contribute to limited systemic bioavailability of the peptide.

The acid is believed to lower the local intestinal pH (where the active agent has been released) to levels below the optimal range for many intestinal proteases. It is believed that this decrease in pH reduces the proteolytic activity of the intestinal proteases, thus affording protection to the peptide from potential degradation. The activity of these proteases is diminished by the temporarily acidic environment provided by the invention.

The total amount of the pH-lowering agent to be administered with each administration of peptide active ingredient should preferably be an amount which, when it is released into the intestine, is sufficient to lower the local intestinal pH substantially below the pH optima for proteases found there. The quantity required will necessarily vary with several factors including the type of pH-lowering agent used (discussed in section "pH-lowering agent") and the equivalents of protons provided by a given pH-lowering agent. In practice, the amount of pH-lowering agent expected to provide good bioavailability is an amount which, if the pharmaceutical composition of the invention were added to a solution of 10 milliliters of 0.1 M sodium bicarbonate, would lower the pH of that sodium bicarbonate solution to no higher than 5.5, and preferably no higher than 4.7, most preferably no higher than 3.5. The foregoing test for sufficient acidity is referenced elsewhere herein as "sodium bicarbonate test" and assumes sufficient passage of time for substantially complete dissolution of the pharmaceutical composition and intermixing thereof with the sodium bicarbonate solution.

In some aspects of the invention, the acid can be used with non-peptidic active agents, such as small molecules.

The acid can for example promote neutralization and the collapse of the GI tract mucus layers, thereby enhancing absorption. In some embodiments, the acid agent has substantially no chelating activity in the lumen of the intestine due to the pH of the environment. One of skilled in the art would appreciate that the chelating properties of an acid, such as citric acid (CA), are strongly pH-dependent. For example, the citric acid capacity to chelate calcium increases about 10 fold for each pH unit from pH 3.0 to pH 6.0. To be able to form a chelation complex, the carboxylic acid groups of citric acid must be deprotonated, to form the citrate anion. Fully deprotonated citrate anion is a potent chelator of calcium, while mono-protonated, di-protonated, and fully protonated citrate are exponentially less potent chelators. To become deprotonated, the pH must be higher than the pKa of the acid group. In the example of citric acid, the reported pKas for CA are 3.1, 4.7 and 6.4. Thus, at high pH, there is more citrate anion, while at low pH there is more fully-protonated citric acid. In other words, the capacity of citric acid to chelate calcium is expected to be higher at a high pH than at a low pH.

Tetracycline analogues, such as tigecycline, are known to interact with calcium ions, resulting in a calcium-tigecycline chelation complex. Chelation of tigecycline with calcium is a known contributing factor to its poor permeability, due to insolubility of the calcium-tigecycline complex. Citric acid (CA) is known to be a potent calcium chelator. It would have been expected that systemic bioavailability of a small molecule such as tigecycline would increase with increased pH (i.e. addition of a base), and, conversely, decrease with decreasing pH (i.e. addition of an acid). It has been shown that the systemic bioavailability of tigecycline increased at pH of 3.5 relative to pH 6.0. It is believed that chelation of intraluminal calcium by citrate anion is not a major factor in increasing the bioavailability of the small molecule, such as tigecycline, as expected and that low pH conditions act synergistically with the absorption enhancer to increase the systemic bioavailability of the small molecule, such as tigecycline (see co-pending U.S. patent application No. 2014/0255479, which is incorporated by reference it its entirety).

In some embodiments, the amount of pH-lowering agent used in a solid oral dosage form of the present disclosure ranges from about 50 milligrams up to about 500 milligrams. In some embodiments, the amount of pH-lowering agent used in a solid oral dosage form of the present disclosure ranges from about 100 milligrams up to about 500 milligrams. In some embodiments, the amount of pH-lowering agent used in a solid oral dosage form of the present disclosure ranges from about 150 milligrams up to about 500 milligrams. In some embodiments, the amount of pH-lowering agent used in a solid oral dosage form of the present disclosure ranges from about 200 milligrams up to about 500 milligrams. In some embodiments, the amount of pH-lowering agent used in a solid oral dosage form of the present disclosure ranges from about 250 milligrams up to about 500 milligrams. In some embodiments, the amount of pH-lowering agent used in a solid oral dosage form of the present disclosure ranges from about 300 milligrams up to about 500 milligrams. In some embodiments, the amount of pH-lowering agent used in a solid oral dosage form of the present disclosure ranges from about 350 milligrams up to about 500 milligrams. In some embodiments, the amount of pH-lowering agent used in a solid oral dosage form of the present disclosure ranges from about 400 milligrams up to about 500 milligrams. In some embodiments, the amount of pH-lowering agent used in a solid oral dosage form of the present disclosure ranges from about 450 milligrams up to about 500 milligrams. In some embodiments, the amount of pH-lowering agent used in a solid oral dosage form of the present disclosure ranges from about 50 milligrams up to about 450 milligrams. In some embodiments, the amount of pH-lowering agent used in a solid oral dosage form of the present disclosure ranges from about 100 milligrams up to about 450 milligrams. In some embodiments, the amount of pH-lowering agent used in a solid oral dosage form of the present disclosure ranges from about 150 milligrams up to about 450 milligrams. In some embodiments, the amount of pH-lowering agent used in a solid oral dosage form of the present disclosure ranges from about 200 milligrams up to about 450 milligrams. In some embodiments, the amount of pH-lowering agent used in a solid oral dosage form of the present disclosure ranges from about 250 milligrams up to about 450 milligrams. In some embodiments, the amount of pH-lowering agent used in a solid oral dosage form of the present disclosure ranges from about 300 milligrams up to about 450 milligrams. In some embodiments, the amount of pH-lowering agent used in a solid oral dosage form of the present disclosure ranges from about 350 milligrams up to about 450 milligrams. In some embodiments, the amount of pH-lowering agent used in a solid oral dosage form of the present disclosure ranges from about 400 milligrams up to about 450 milligrams. In some embodiments, the amount of pH-lowering agent used in a solid oral dosage form of the present disclosure ranges from about 50 milligrams up to about 400 milligrams. In some embodiments, the amount of pH-lowering agent used in a solid oral dosage form of the present disclosure ranges from about 100 milligrams up to about 400 milligrams. In some embodiments, the amount of pH-lowering agent used in a solid oral dosage form of the present disclosure ranges from about 150 milligrams up to about 400 milligrams. In some embodiments, the amount of pH-lowering agent used in a solid oral dosage form of the present disclosure ranges from about 200 milligrams up to about 400 milligrams. In some embodiments, the amount of pH-lowering agent used in a solid oral dosage form of the present disclosure ranges from about 250 milligrams up to about 400 milligrams. In some embodiments, the amount of pH-lowering agent used in a solid oral dosage form of the present disclosure ranges from about 300 milligrams up to about 400 milligrams. In some embodiments, the amount of pH-lowering agent used in a solid oral dosage form of the present disclosure ranges from about 350 milligrams up to about 400 milligrams. In some embodiments, the amount of pH-lowering agent used in a solid oral dosage form of the present disclosure ranges from about 50 milligrams up to about 350 milligrams. In some embodiments, the amount of pH-lowering agent used in a solid oral dosage form of the present disclosure ranges from about 100 milligrams up to about 350 milligrams. In some embodiments, the amount of pH-lowering agent used in a solid oral dosage form of the present disclosure ranges from about 150 milligrams up to about 350 milligrams. In some embodiments, the amount of pH-lowering agent used in a solid oral dosage form of the present disclosure ranges from about 200 milligrams up to about 350 milligrams. In some embodiments, the amount of pH-lowering agent used in a solid oral dosage form of the present disclosure ranges from about 250 milligrams up to about 350 milligrams. In some embodiments, the amount of pH-lowering agent used in a solid oral dosage form of the present disclosure ranges from about 300 milligrams up to about 350 milligrams. In some embodiments, the amount of pH-lowering agent used in a solid oral dosage form of the present disclosure ranges from about 50 milligrams up to about 300 milligrams. In some embodiments, the amount of pH-lowering agent used in a solid oral dosage form of the present disclosure ranges from about 100 milligrams up to about 300 milligrams. In some embodiments, the amount of pH-lowering agent used in a solid oral dosage form of the present disclosure ranges from about 150 milligrams up to about 300 milligrams. In some embodiments, the amount of pH-lowering agent used in a solid oral dosage form of the present disclosure ranges from about 200 milligrams up to about 300 milligrams. In some embodiments, the amount of pH-lowering agent used in a solid oral dosage form of the present disclosure ranges from about 250 milligrams up to about 300 milligrams. In some embodiments, the amount of pH-lowering agent used in a solid oral dosage form of the present disclosure ranges from about 50 milligrams up to about 250 milligrams. In some embodiments, the amount of pH-lowering agent used in a solid oral dosage form of the present disclosure ranges from about 100 milligrams up to about 250 milligrams. In some embodiments, the amount of pH-lowering agent used in a solid oral dosage form of the present disclosure ranges from about 150 milligrams up to about 250 milligrams. In some embodiments, the amount of pH-lowering agent used in a solid oral dosage form of the present disclosure ranges from about 200 milligrams up to about 250 milligrams. In some embodiments, the amount of pH-lowering agent used in a solid oral dosage form of the present disclosure ranges from about 50 milligrams up to about 200 milligrams. In some embodiments, the amount of pH-lowering agent used in a solid oral dosage form of the present disclosure ranges from about 100 milligrams up to about 200 milligrams. In some embodiments, the amount of pH-lowering agent used in a solid oral dosage form of the present disclosure ranges from about 150 milligrams up to about 200 milligrams. In some embodiments, the amount of pH-lowering agent used in a solid oral dosage form of the present disclosure ranges from about 50 milligrams up to about 150 milligrams. In some embodiments, the amount of pH-lowering agent used in a solid oral dosage form of the present disclosure ranges from about 100 milligrams up to about 150 milligrams. In some embodiments, the amount of pH-lowering agent used in a solid oral dosage form of the present disclosure ranges from about 100 milligrams up to about 100 milligrams. In some embodiments, the amount of pH-lowering agent used in a solid oral dosage form of the present disclosure is about 50 milligrams. In some embodiments, the amount of pH-lowering agent used in a solid oral dosage form of the present disclosure is about 75 milligrams. In some embodiments, the amount of pH-lowering agent used in a solid oral dosage form of the present disclosure is about 100 milligrams. In some embodiments, the amount of pH-lowering agent used in a solid oral dosage form of the present disclosure is about 125 milligrams. In some embodiments, the amount of pH-lowering agent used in a solid oral dosage form of the present disclosure is about 150 milligrams. In some embodiments, the amount of pH-lowering agent used in a solid oral dosage form of the present disclosure is about 175 milligrams. In some embodiments, the amount of pH-lowering agent used in a solid oral dosage form of the present disclosure is about 200 milligrams. In some embodiments, the amount of pH-lowering agent used in a solid oral dosage form of the present disclosure is about 225 milligrams. In some embodiments, the amount of pH-lowering agent used in a solid oral dosage form of the present disclosure is about 250 milligrams. In some embodiments, the amount of pH-lowering agent used in a solid oral dosage form of the present disclosure is about 300 milligrams. In some embodiments, the amount of pH-lowering agent used in a solid oral dosage form of the present disclosure is about 325 milligrams. In some embodiments, the amount of pH-lowering agent used in a solid oral dosage form of the present disclosure is about 350 milligrams. In some embodiments, the amount of pH-lowering agent used in a solid oral dosage form of the present disclosure is about 375 milligrams. In some embodiments, the amount of pH-lowering agent used in a solid oral dosage form of the present disclosure is about 400 milligrams. In some embodiments, the amount of pH-lowering agent used in a solid oral dosage form of the present disclosure is about 425 milligrams. In some embodiments, the amount of pH-lowering agent used in a solid oral dosage form of the present disclosure is about 450 milligrams. In some embodiments, the amount of pH-lowering agent used in a solid oral dosage form of the present disclosure is about 475 milligrams. In some embodiments, the amount of pH-lowering agent used in a solid oral dosage form of the present disclosure is about 500 milligrams or higher. The foregoing preferences relate to the total combined weight of all pH-lowering agents where two or more of such agents are used in combination.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. In some embodiments, the at least one pH-lowering agent has a pKa no higher than 4.2, or no higher than 3.0. In some embodiments, the pH lowering agent has a solubility in water of at least 30 grams per 100 milliliters of water at room temperature. In some embodiments, organic acids are used.

Examples of compounds that induce higher hydrogen ion content include aluminum chloride and zinc chloride. Pharmaceutically acceptable traditional acids include, but are not limited to acid salts of amino acids (e.g. amino acid hydrochlorides) or derivatives thereof.

Examples of these are acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other examples of useful pH-lowering compounds include carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like.

Other useful pH-lowering agents that might not usually be called "acids" in the art, but which may nonetheless be useful in accordance with the invention are phosphate esters (e.g., fructose 1, 6 diphosphate, glucose 1, 6 diphosphate, phosphoglyceric acid, and diphosphoglyceric acid). CARBOPOL® (Trademark BF Goodrich) and polymers such as polycarbophil may also be used to lower pH.

Any combination of pH lowering agents that achieves the required pH level of no higher than 5.5 in the sodium bicarbonate test discussed supra may be used. Some embodiments utilize, as at least one of the pH-lowering agents of the pharmaceutical composition, an acid selected from the group consisting of citric acid, tartaric acid and an acid salt of an amino acid.

In some embodiments, regardless of the acid chosen, the acid is in the form of acid particles coated with a protective coating discussed in a separate section, infra.

In some embodiments, the weight ratio of pH-lowering agent to the API can be from 0.1:1 to 10,000:1. In some embodiments, the weight ratio of pH-lowering agent to the API can exceed 20:1, 200:1, or 800:1 or 2000:1.

Water Soluble Barrier Layer

The water soluble barrier layer can be comprised of a compound that is water soluble in both acidic and basic environments. Examples of compounds useful for this purpose include but are not limited to hydroxypropylmethylcellulose, hydroxypropylcellulose, methylcellulose and polyvinylpyrrolidone. Preferably, water solubility is at least one gram, more preferably at least 11 grams, per 100 milliliters at room temperature. Polyvinylpyrrolidone is preferred in some embodiments. In some embodiments water solubility, at both pH 6.0 and pH 8.0, is in excess of 12 grams per 100 milliliters of water at room temperature. Good solubility in both acid and basic pH aids desirable quick dissolution in the intestinal region where pH is generally basic, but where the pharmaceutical composition's release of significant quantities of acid might at least temporarily impede dissolution of a material that was not also readily soluble in an aqueous acid environment. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form. In some embodiments, the water-soluble barrier layer is present at a weight of from about 6.0% to about 15.0% of the weight of the remainder of the solid oral dosage form. In some embodiments, the water-soluble barrier layer is present at a weight of about 13.0% to about 15.0% of the weight of the remainder of the solid oral dosage form. In some embodiments, the water-soluble barrier layer is present at a weight of from about 12 to about 19 mg/cm$^2$.

Coated Acid Particles

In some embodiments, the acid is provided, at least in part, by acid particles coated with a protective coating to reduce undesirable acid interaction with other components of the formulation, such as the peptide active agent and, where used, the outer enteric coating. In some embodiments, the coating is an hydrophilic coating. In some embodiments, the coating is water soluble coating.

When coated acid particles are used, the particles are coated with a pharmaceutically acceptable protective coating that is non-acidic and preferably has a solubility in water of at least one gram, and preferably at least 10 grams, per 100 milliliters of water at room temperature. As the coating is for the purpose of reducing acid interaction with other components of the pharmaceutical composition, it is important that the coating not itself be acidic such that its own acidity could undesirably cause some of the acid interactions that it is the coating's purpose to prevent.

Appropriate coating materials include but are not limited to monosaccharides (e.g. glucose and fructose), polysaccharides (e.g. maltodextrin), and acid salts (e.g. sodium citrate). When acid salts are used, it is preferred, but not required, that they be salts of the acid being coated (e.g., sodium citrate-coated citric acid particles). In some embodiments, coated citric acid particles used in a solid dosage form of the present disclosure are Citro DC available from Jungbunzlauer. Citro DC is a direct compressible type of citric acid coated with a thin layer of maltodextrin. In some embodiments, coated citric acid particles used in a solid dosage form of the present disclosure are CITROCOAT® N available from Jungbunzlauer. When used as the acid, citric acid or other organic acids can be coated by spraying a coating solution which contains, for example, glucose or sodium citrate onto granules of an organic acid in a fluid-bed dryer. Coatings discussed herein may be used on particles of other acids discussed herein.

Preferred average size of the acid-coated particles is from 30 mesh to 140 mesh.

Absorption/permeation Enhancer

In some embodiments, an absorption enhancer (also referred herein as permeation enhancer) is included in the solid oral dosage form. The absorption enhancers can be present in a quantity that constitutes from 0.1 to 20.0 percent by weight, relative to the overall weight of the solid oral dosage form (exclusive of any enteric coating). In some embodiments, absorption enhancers can be surface active agents which act both as solubility enhancers and uptake enhancers. Generically speaking, "solubility enhancers" improve the ability of the components of the disclosure to be solubilized in either the aqueous environment into which they are originally released or into the lipophilic environment of the mucous layer lining the intestinal walls, or both. "Transport (uptake) enhancers" (which are frequently the same surface active agents used as solubility enhancers) are those which facilitate the ease by which API cross the intestinal wall.

One or more absorption enhancers may perform one function only (e.g., solubility), or one or more absorption enhancers may perform the other function only (e.g., uptake), within the scope of the disclosure. It is also possible to have a mixture of several compounds some of which provide improved solubility, some of which provide improved uptake and/or some of which perform both functions. Without intending to be bound by theory, it is believed that uptake enhancers may act by (1) increasing disorder of the hydrophobic region of the membrane exterior of intestinal cells, allowing for increased transcellular transport; or (2) leaching membrane proteins resulting in increased transcellular transport; or (3) widening the pore radius between cells for increased paracellular transport.

Surface active agents are believed to be useful both as solubility enhancers and as uptake enhancers. For example, detergents are useful in (1) solubilizing all of the active components quickly into the aqueous environment where they are originally released, (2) enhancing lipophilicity of the components of the disclosure, especially the API, aiding its passage into and through the intestinal mucus, (3) enhancing the ability of the normally polar API to cross the epithelial barrier of the brush border membrane; and (4) increasing transcellular and/or paracellular transport as described above.

In some embodiments, when surface active agents are used as the absorption enhancers, they can be free flowing powders for facilitating the mixing and loading of during the manufacturing process. Because of inherent characteristics of some peptide active ingredients (e.g., their isoelectric point, molecular weight, amino acid composition, etc.) certain surface active agents interact best with certain peptides. In some embodiments, the surface active agent used is as an absorption enhancer selected from the group consisting of (i) anionic surface active agents, (ii) cationic surface agents, (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. In some embodiments, the anionic surface active agent is one of a cholesterol derivative (e.g., bile acids), sodium lauryl sulfate (SLS, also known as Sodium dodecyl sulfate (SDS)) or a combination thereof. In some embodiments, the cationic surface agent is an acylcarnitine or the like.

In some embodiments, the absorption enhancer is soluble at acid pH, particularly in the 3.0 to 5.0 range.

In some embodiments, a mixture of cationic surface active agents and anionic surface active agents that are cholesterol derivatives, both of which are soluble at acid pH, are used.

In some embodiments, an acid soluble bile acid is used together with a cationic surface active agent. In some embodiments, an acyl carnitine and a sucrose ester is used. In some embodiments, when a particular absorption enhancer is used alone, it is a cationic surface active agent. Acyl carnitines (e.g., lauroyl carnitine), phospholipids and bile acids are particularly good absorption enhancers, especially acyl carnitine. Anionic surfactants such as cholesterol derivatives or SLS are also used in some embodiments. Sodium lauryl sulfate is an hydrophobic surfactant. In some embodiments, the permeation enhancer is sodium dodecyl sulphate (SDS) or a pharmaceutically acceptable surfactant having suitable CMC.

It is the intent of these preferences to avoid interactions with the API that interfere with absorption of active ingredient into the blood. For example, the API may become entrapped in micelles of the surfactant, and thus physically unavailable for permeation across the intestinal epithelium.

To reduce the likelihood of side effects, preferred detergents, when used as the absorption enhancers of the disclosure, are either biodegradable or reabsorbable (e.g. biologically recyclable compounds such as bile acids, phospholipids, and/or acyl carnitines), preferably biodegradable. Acyl carnitines are believed particularly useful in enhancing paracellular transport. When a bile acid (or another anionic detergent lacking linear hydrocarbons) is used in combination with a cationic detergent, some peptides, such as salmon calcitonin, can be better transported both to and through the intestinal wall. In some embodiments, and without intending to be bound by theory, cationic ion exchange agents (e.g. detergents) are included to provide solubility enhancement by another possible mechanism. In particular, they may prevent the binding of the peptide active ingredient to mucus. Preferred cationic ion exchange agents include protamine chloride or any other polycation.

Preferred absorption enhancers include one or more of: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lyso-phosphatidylethanolamine; (f) acylcarnitines, acylcholines and acyl amino acids such as lauroyl-L-carnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylene-diaminetetraacetic acid; (j) cationic surfactants such as cetylpyridinium chloride; (k) fatty acid derivatives of polyethylene glycol such as Labrasol, Labrafac, etc.; (l) alkylsaccharides such as lauryl maltoside, lauroyl sucrose, myristoyl sucrose, palmitoyl sucrose, etc . . . , (m) sodium lauryl sulfate (SLS), or a pharmaceutically acceptable surfactant having similar CMC or any combinations of the foregoing.

Acid-Resistant Protective Vehicle

An acid-resistant protective vehicle can be utilized to separate the peptide compound from stomach proteases. Any carrier or vehicle that protects the peptide from stomach proteases and then dissolves so that the other ingredients of the invention may be released in the intestine is suitable. Examples include cellulose acetate phthalate, hydroxypropyl methylethylcellulose succinate, hydroxypropyl methylcellulose phthalate, carboxyl methylethylcellulose and methacrylic acid-methyl methacrylate copolymer. In some embodiments, the peptide, absorption enhancers such as solubility and/or uptake enhancer(s) (when included), chymotrypsin inhibitor, and pH-lowering agent(s), are included in a sufficiently viscous protective syrup to permit protected passage of the components of the invention through the stomach.

Suitable enteric coatings for protecting the peptide from stomach proteases may be applied, for example, to capsules after the remaining components of the invention have been loaded within the capsule. In other embodiments, enteric coating is coated on the outside of a tablet or coated on the outer surface of particles of active components which are then pressed into tablet form, or loaded into a capsule, which is itself preferably coated with an enteric coating.

It is desirable that all components of the disclosure be released from the carrier or vehicle, and solubilized in the intestinal environment as simultaneously as possible. In some embodiments, the vehicle or carrier can release the active components in the small intestine where uptake enhancers that increase transcellular or paracellular transport are less likely to cause undesirable side effects than if the same uptake enhancers were later released in the colon. It is emphasized, however, that the present disclosure is believed effective in the colon as well as in the small intestine. In some embodiments, the acid resistant protective vehicle is present at a weight which is from about 3.0% to about 10.0% of the weight of the remainder of the solid oral dosage form (the "remainder" being the solid oral dosage form exclusive of enteric coating itself). In some embodiments, the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, a composition of the present disclosure is an enteric coated capsule that is sufficient to prevent breakdown of the solid oral dosage form of the disclosure in 0.1N HCl for at least two hours, then capable of permitting complete release of all contents of the solid oral dosage form within thirty minutes after pH is increased to 6.8 or pH 6.8 to 7.5 in a dissolution bath in which said composition is rotating at greater than 100 revolutions per minute hours. In embodiments in which the water-soluble barrier layer of the disclosure is used, less enteric coating may be required, sometimes less than the amount of water-soluble barrier layer.

In some embodiments, a composition of the present disclosure is an enteric coated tablet that is sufficient to prevent breakdown of the solid oral dosage form of the disclosure in 0.1N HCl for at least two hours, then capable of permitting complete release of all contents of the solid oral dosage form within thirty-sixty minutes after pH is increased to 6.8 (e.g. pH 6.8-7.5) in an apparatus 2 (paddle) in which said composition is rotating at greater than 100 revolutions per minute.

Filler

In some embodiments, the filler is a cellulose derivative filler, such as carboxymethylcellulose, cellulose acetate, hydroxyethylcellulose, hydroxypropylcellulose, hydroxypropylmethylcellulose. To achieve the desired release profile, a high molecular weight (high viscosity) hydroxypropylcellulose (HPC) can be used. High molecular weight (high viscosity) hydroxypropylcellulose is known to effectively sustain the release of drugs. In some embodiments, the filler has a viscosity of about 3,000 to 120,000 cP at 20° C.

In some embodiments, a filler such as a cellulose filler like PROSOLV™ available from JRS Pharma can be utilized. In some embodiments, a cellulose filler such as Avicel™ PH (microcrystalline cellulose) available from FMC BioPolymer may be utilized. In some embodiments, a cellulose filler such as Avicel™ HFE (microcrystalline cellulose, co-processed with mannitol) available from FMC BioPolymer may be utilized. In some embodiments, a filler such as, Pearlitol™ (mannitol) available from Roquette Freres may be utilized. Other fillers are known in the art.

Optional Pharmaceutical Binder

In some embodiments, the solid oral dosage form is in tablet form and a pharmaceutical binder can be included in the solid oral dosage form. Preferred binders include but are not limited to KOLLIDON VA64, KOLLIDON VA64 fine, KOLLIDON 30, AVICEL PH-101, HPC, PHARMACOAT 606, and MALDEX.

Optional Pharmaceutical Disintegrant

In some embodiments, a pharmaceutical tablet is used as a preferred single oral dosage form. In some embodiments, a pharmaceutically acceptable disintegrant is included. Any disintegrant that performs the function of enhancing dissolution speed may be used. In some embodiments, the disintegrants include but are not limited to KOLLIDON CL, POLYPLASDONE, EXPLOTAB, and AC-DI-SOL, available from International Specialty Products, JRS Pharma and FMC Biopolymer, respectively. In some embodiments, the disintegrant is present in an amount between 1 and 15 percent by weight relative to the total tablet weight (% wt, when tablets are used), exclusive of any water-soluble barrier layer and any acid-resistant protective vehicle. In some embodiments, the solid oral dosage form may include a reduced amount of disintegrant. In some embodiments, the solid oral dosage comprises less than 4% wt, less than 3.5% wt, less than 3% wt, less than 2.5% wt, less than 2% wt, less than 1.5% wt, less than 1% wt, less than 0.5% wt, less than 0.01% wt, less than 0.001% wt disintegrant. In some embodiments, the solid oral dosage does not include a tablet disintegrant.

Optional Pharmaceutical Glidant

In some embodiments, a pharmaceutically acceptable glidant is included. Any glidant that performs the function of enhancing powder flow may be used. Preferred glidants include but are not limited to talc, calcium silicate, magnesium silicate, silicon dioxide. Preferably, the glidant is present in an amount between 0.1 and 2.0 percent by weight relative to the weight of the pharmaceutical composition, exclusive of any water-soluble barrier layer and any acid-resistant protective vehicle.

Optional Pharmaceutical Lubricant

In some embodiments, a pharmaceutically acceptable lubricant is included. Any lubricant that performs the function of preventing powder from sticking to the tooling may be used. Preferred lubricants include but are not limited to stearic acid, magnesium stearate, and hydrogenated vegetable oil type 1. In some embodiments, the lubricant is present in an amount between 0.2 and 5.0 percent by weight relative to the weight of the solid oral dosage form, exclusive of any water-soluble barrier layer and any acid-resistant protective vehicle.

Optional Antioxidant

In some embodiments, a pharmaceutically acceptable antioxidant is included. Any antioxidant that performs the function of preventing the oxidation of labile amino acids in peptides, such as methionine or tryptophan may be used. Preferred antioxidants include but are not limited to sodium pyruvate, derivatives of sodium pyruvate, ascorbic acid, ascorbyl palmitate, butylated hydroxyanisole, butylated hydroxytoluene, sodium bisulfate, and sodium metabisulfite. In some embodiments, the antioxidant is present in an amount between 0.5 and 5 mg per tablet.

Miscellaneous Other Optional Ingredients

In some embodiments, another peptide (such as albumin, casein, soy protein, other animal or vegetable proteins and the like) can be included to reduce non-specific adsorption (e.g., binding of peptide to the intestinal mucus barrier) thereby lowering the necessary concentration of the expensive peptide active ingredient. When added, the peptide is in some embodiments, from 1.0 to 10.0 percent by weight relative to the weight of the overall solid oral dosage form (excluding any water-soluble barrier layer and any acid-resistant protective vehicle). Preferably, this additional peptide is not physiologically active and is most preferably a food peptide such as soybean peptide or the like. Without intending to be bound by theory, this additional non-physiologically active peptide, may also increase bioavailability by acting as a protease scavenger that desirably competes with the peptide active ingredient for protease interaction. The second peptide may also aid the active compound's passage through the liver.

All solid oral dosage forms of the present disclosure may optionally also include common pharmaceutical carriers, diluents or fillers. The solid oral dosage forms may include gelatin capsules, preservatives, colorants and the like in their usual known sizes and amounts.

The optional ingredients discussed herein are not exclusive. Other pharmaceutically acceptable agents may also be included. All optional components may be combined in any combination. Because most preferences stated herein provide benefits by different mechanisms, such combinations should be beneficial.

Inhibitor of Proteolytic Degradation of the Active Agent

When the active agent is a protein or a peptide, a protease inhibitor may be added that prevents or reduces of the proteolytic degradation of the active agent, which may occur under in the environmental conditions of the gastrointestinal tract. Preferably, the protease inhibitor that prevents or reduces the proteolytic degradation of the active agent should be pharmaceutically acceptable in relation to the certain application in animals or in humans. In some embodiments, inhibitors of trypsin or chymotrypsin can be added.

Other Optional Preferences

When prepared in tablet form, it is preferred that the maximum weight loss during friability testing be no greater than 1%. As used herein, friability testing refers to the technique described in "Tablet Friability", Chapter 1216, USP 28 page 2745.

When absorption enhancers are used, it is preferred that the weight ratio of pH-lowering agent(s) (exclusive of coating on any coated acid particles being used) to absorption enhancer(s) be between 5:2 and 20:1, 4:1-12:1, or between 5:1-10:1. The total weight of all pH-lowering agents and the total weight of all absorption enhancers in a given solid oral dosage forms is included in the foregoing preferred ratios. For example, if a solid oral dosage forms includes two pH-lowering agents and three absorption enhancers, the foregoing ratios will be computed on the total combined weight of both pH-lowering agents and the total combined weight of all three absorption enhancers.

In some embodiments, the pH-lowering agent, the API, the absorption enhancer, when used, (whether single compounds or a plurality of compounds in each category) are uniformly dispersed in the solid oral dosage forms. In some embodiments, the solid oral dosage forms comprise granules that include a pharmaceutical binder having the API, the pH-lowering agent and the absorption enhancer uniformly dispersed within said binder. In some embodiments, granules may consist of an acid core, surrounded by a uniform layer of organic acid, a layer of enhancer and a layer of the API that is surrounded by an outer layer of organic acid. Granules may be prepared from an aqueous mixture consisting of pharmaceutical binders such as polyvinyl pyrrolidone or hydroxypropyl methylcellulose, together with the pH-lowering agents, optional absorption enhancers, and API of the disclosure.

In some embodiments, API, acid (preferably coated acid), absorption enhancer, a pharmaceutical binder (when necessary), a disintegrant (when used), a glidant, a stabilizer (when necessary) and a lubricant are thoroughly intermixed, compressed into tablet form, coated with a water-soluble barrier layer (preferably adding at least about 3% to the weight of the tablet (e.g. about 3-6%), which is in turn coated with an enteric coating that adds another about 4-15% to the weight of the tablet (e.g. 4-7%). In some embodiments, the water soluble layer adds more than the enteric coating (e.g. 6% and 4%, respectively).

In some embodiments, a single tablet is used at each administration because a single tablet best provides simultaneous release of the API, pH-lowering agent and absorption enhancers. This is desirable because the acid is best able to reduce undesirable proteolytic attack on the peptide when released in close time proximity to release of the peptide. Near simultaneous release is best achieved by administering all components of the invention as a single tablet. However, the invention also includes, for example, dividing the required amount of acid, and enhancers among two or more tablets which may be administered together such that they together provide the necessary amount of all ingredients. "Pharmaceutical composition" and "solid oral dosage form" as used herein include a complete dosage appropriate to a particular administration to a human patient regardless of how it is subdivided so long as it is for substantially simultaneous administration.

In some embodiments, the single dosage form for oral delivery of an API comprises from about 250 mg to about 500 mg of citric acid; from about 11 mg/cm$^2$ to about 19 mg/cm$^2$ of a water-soluble undercoat; and from about 5 mg/cm$^2$ to about 15 mg/cm$^2$ of an enteric coating; wherein the API and the citric acid are in the same layer of the dosage form.

In some embodiments, the solid oral dosage form comprises an API intermixed with coated acid particles, the coated acid particles comprising an acid that is coated with a pharmaceutically acceptable protective coating to separate the acid from the API in the solid oral dosage form; an acid resistant protective vehicle; and a water-soluble barrier layer that separates the pH-lowering agent from the acid resistant protective vehicle, wherein the acid resistant protective vehicle is present at a weight from about 7% to about 10%, and wherein the water-soluble barrier layer is present at a weight from about 3.0% to about 12.0%.

In some embodiments, the coated acid particles can be present at a range from about 250 mg to about 500 mg. In some embodiments, the acid include carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like. In some embodiments, the acid is selected from citric acid, tartaric acid and an acid salt of an amino acid.

In some embodiments, the absorption enhancer comprises an acyl carnitine, or SDS.

In some embodiments, a solid oral dosage form of the present disclosure includes an acid protective vehicle such as an outer layer of enteric coating. Such vehicles are desirable for enhancing bioavailability, but can slow uptake of the API into the bloodstream. In some embodiments, uniform dissolution of the acid protective vehicle in the intestines may be facilitated by keeping the acid of the solid oral dosage form away from the vehicle during its dissolution. This may be accomplished in accordance with the invention in one of or more of the following ways. First, the use of a protective water soluble barrier layer between the acid protective vehicle and the acid (pH-lowering agent) of the solid oral dosage form can enhance the more uniform release of all solid oral dosage form in the intestines by permitting most of the acid protective vehicle to dissolve in the intestines before the acid (pH-lowering agent) of the solid oral dosage form is released or otherwise comes in contact with the acid protective vehicle. Otherwise the acid (pH-lowering agent) could adversely affect the dissolution of the acid protective vehicle (which is insoluble in acid environment). This water soluble barrier layer is expected to provide this benefit regardless of the form in which the acid (pH-lowering agent) is supplied, and even when coated acid particles (used in other embodiments of the invention) are not present. In some embodiments, the water-soluble barrier layer adds at least 3% to the weight of the solid oral dosage form, exclusive of any acid-protective vehicle. In some embodiments, the water-soluble barrier layer adds from about 3% to about 12% to the weight of the solid oral dosage form, exclusive of any acid-protective vehicle.

Second, the acid (pH-lowering agent) of the composition may be provided in the form of coated acid particles. The coating on these particles is a pharmaceutically acceptable protective coating that is non-acidic and has a solubility in water of at least one gram per 100 milliliters of water at room temperature. In addition to desirably separating the pharmaceutical acid (pH-lowering agent) from the peptide compound, this coating on the acid particles may help protect the solid oral dosage form's acid resistant protective vehicle from the undesirable effects acid can have on quick uniform dissolution of the outer coating in the intestines. This is true even in embodiments of the present disclosure that do not include the protective water soluble barrier layer. In some, but not all, embodiments of the present disclosure, both (1) the protective water soluble barrier layer is present, and (2) the acid (pH-lowering agent) is supplied, at least in part, in the form of coated acid particles.

Likewise, providing acid (pH-lowering agent) to the solid oral dosage form in the form of the foregoing coated acid particles provides numerous advantages that are independent of any effect on enteric coating, and independent of whether or not a protective water soluble barrier layer is used. Such coated acid particles may therefore be used advantageously even in embodiments of the present disclosure that include neither outer coating of acid protective vehicle, nor protective barrier layer. In particular, acid (pH-lowering agent) in the form of coated particles may desirably be thoroughly intermixed with the peptide compound, while undesirable acid-peptide interaction is minimized. Without intending to be bound by theory, this thorough intermixing is believed to facilitate uniform release of each component together so that acid (pH-lowering agent) may better protect the peptide compound, in the intestinal environment, by reducing peptide degradation from the activity of local proteases having neutral or basic pH optima.

In some but not all embodiments, an absorption enhancer is included in a solid oral dosage form to further enhance bioavailability. In some embodiments, coated acid particles, API, absorption enhancer, acid protective vehicle and protective water soluble barrier layer are all present. The use of coated acid particles, in addition to reducing undesirable acid interactions with other components discussed herein, desirably reduces acid interaction with absorption enhancer (when used) or with surfactant (when used).

In some embodiments, coated acid, API, and, optionally, one or more of any optional components discussed herein, e.g. an absorption enhancer, are thoroughly intermixed. The mixture is then coated with both a protective water soluble barrier layer and an outer acid-protective vehicle. In some embodiments, the water soluble barrier layer lies just inside of an acid protective vehicle layer, and separates the vehicle layer from the intermixed remaining contents. In some embodiments, the acid resistant protective vehicle is present at a weight which is from about 3.0% to about 10.0% of the weight of the remainder of the solid oral dosage form. In some embodiments, the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, the water-soluble barrier layer is present at a weight which is from about 6.0% to about 15.0% of the weight of the remainder of the solid oral dosage form. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form.

The acid protective vehicle preferably constitutes an outermost protective layer surrounding the remainder of the solid oral dosage form. The vehicle does not dissolve in the acidic stomach environment, thus protecting the peptide compound from stomach proteases. Without intending to be bound by theory, it is believed that, later, in the basic pH environment of the intestines, the vehicle dissolves quickly without interference from the pharmaceutical acid from which the vehicle is separated by either the barrier layer, or the coating on the acid particles, or both. It is believed that, once the protective vehicle dissolves, the water-soluble barrier layer and the coating surrounding the acid particles release the remaining components of the composition.

The acid (also referred herein as pH lowering agent) is believed to lower the local intestinal pH (where the active agent has been released) to levels below the optimal range for many intestinal proteases. It is believed that this decrease in pH reduces the proteolytic activity of the intestinal proteases, thus affording protection to the peptide compound from potential degradation. The activity of these proteases is diminished by the temporarily acidic environment provided by a solid oral dosage form of the present disclosure. In some embodiments, sufficient acid is provided so that local intestinal pH is lowered temporarily to 5.5 or below. In some embodiments, sufficient acid is provided so that local intestinal pH is lowered temporarily to 4.7 or below. In some embodiments, sufficient acid is provided so that local intestinal pH is lowered temporarily to 3.5 or below. The sodium bicarbonate test, described in the section captioned "the pH-Lowering Agent", is indicative of the required acid amount. Preferably, conditions of reduced intestinal pH persist for a time period sufficient to protect the API (e.g. peptide, hormone or analogue thereof) from proteolytic degradation until at least some of the peptide compound has had an opportunity to cross the intestinal wall into the bloodstream. Optionally, absorption enhancers, when used, may synergistically promote peptide absorption into the blood while conditions of reduced proteolytic activity prevail. Preferred absorption enhancers and their use are discussed in more detail in a separate section.

Acid and API (e.g. peptide compound) and, when present, the absorption enhancer, should be released together to the extent possible. The acid is then better able to protect, for example, the peptide compound by reducing degradation of the peptide compound by action of neutral or basic-acting proteases until the peptide compound crosses the intestinal wall into the bloodstream. A concomitant release of absorption enhancer (when used) can further enhance that crossing of the intestinal wall. In a tablet of the present disclosure, additional optional materials, discussed in separate sections herein, aid in forming tablets of appropriate hardness that resist breaking prior to administration, and undergo consistent and complete dissolution at the appropriate time after administration.

In some embodiments, the API comprises a peptide compound. In some embodiments, the API is a peptide compound that includes a plurality of amino acids and at least one peptide bond in its molecular structure. In some embodiments, the molecular weight of the peptide compound ranges from about 500 Daltons up to about 10,000 Daltons. In some embodiments, the peptide compound is a peptide hormone or analogue thereof. In some embodiments, the hormone or analogue thereof is selected from a gonadotrophin releasing hormone (GnRH) analogue including, but not limited to, triptorelin, leuprorelin and goserelin. In some embodiments, the hormone analogue is leuprorelin. In some embodiments, the single oral dosage form is a single tablet or capsule. In some embodiments, an average particle size of the coated acid particles is between 30 mesh and 140 mesh.

A single dosage form for oral delivery of a peptide compound includes from about 1 mg to about 3 mg of a gonadotrophin releasing hormone (GnRH) analogue; from about 250 mg to about 500 mg of citric acid; from about 11 mg/cm$^2$ to about 19 mg/cm$^2$ of a water-soluble undercoat; and from about 5 mg/cm$^2$ to about 15 mg/cm$^2$ of an enteric coating; wherein the gonadotrophin releasing hormone (GnRH) analogue and the citric acid are in the same layer of the dosage form. In some embodiments, the absorption enhancer is an acyl carnitine. In some embodiments, the absorption enhancer is lauroyl-L-carnitine. In some embodiments, the gonadotrophin releasing hormone (GnRH) analogue is selected from the group consisting of triptorelin, leuprorelin and goserelin. In some embodiments, the gonadotrophin releasing hormone analogue is leuprorelin.

In some embodiments, the solid oral dosage form comprises a peptide compound intermixed with coated acid particles, the coated acid particles comprising citric acid that is coated with a pharmaceutically acceptable protective coating to separate the acid from the peptide compound in the solid oral dosage form, the coated acid particles present at a range from about 250 mg to about 500 mg; an acid resistant protective vehicle; and a water-soluble barrier layer that separates the pH-lowering agent from the acid resistant protective vehicle, wherein the acid resistant protective vehicle is present at a weight from about 7% to about 10%, and wherein the water-soluble barrier layer is present at a weight from about 3.0% to about 12.0%. In some embodiments, the solid oral dosage form further comprises a cellulose filler. In some embodiments, the cellulose filler is a high viscosity cellulose filler. In some embodiments, the solid oral dosage form further comprises an absorption enhancer. In some embodiments, the solid oral dosage form further comprises a pharmaceutical binder. In some embodiments, when the solid oral dosage form is ingested, the acid-resistant protective vehicle is breached in the intestine in the distal part of the duodenum, the jejunum, the ileum, or the colon, the citric acid is released from the coated acid particles. In some embodiments, the citric acid can reduce the activity of intestinal proteases.

One of the mechanisms by which the present disclosure is believed to accomplish the goal of enhanced bioavailability is aided by having an enteric coating having a suitable thickness, and active components of the pharmaceutical composition released together as uniformly as possible. The acid-resistant protective vehicle should normally add less than about 30% to the weight of the remainder of solid oral dosage form (i.e., the other components of the composition excluding the acid-resistant protective vehicle). When a water-soluble barrier layer is used in addition to the acid-resistant protective vehicle, less acid-resistant protective vehicle may be required. In some embodiments, the acid resistant protective vehicle is present at a weight which is from about 3.0% to about 10.0% of the weight of the remainder of the solid oral dosage form. In some embodiments, the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form.

According to aspects illustrated herein, there is disclosed a solid oral dosage form that includes a therapeutically effective amount of at least one hormone or analogue thereof; at least one pharmaceutically acceptable pH-lowering agent; an acid resistant protective vehicle; and a water-soluble barrier layer that separates the pH-lowering agent from the acid resistant protective vehicle. In some embodiments, the pH-lowering agent is present in the solid oral dosage form in a quantity which, if the solid oral dosage form were added to ten milliliters of 0.1M aqueous sodium bicarbonate solution, would be sufficient to lower the pH of said solution to no higher than 5.5. In some embodiments, the acid resistant protective vehicle is present at a weight which is from about 3.0% to about 10.0% of the weight of the remainder of the solid oral dosage form. In some embodiments, the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form. In some embodiments, the solid oral dosage form further includes an absorption enhancer. In some embodiments, the absorption enhancer is a surface active agent. In some embodiments, the surface active agent is absorbable or biodegradable. In some embodiments, the surface active agent is selected from the group consisting of acylcarnitines, phospholipids and bile acids. In some embodiments, the surface active agent is an acyl carnitine. In some embodiments, the solid oral dosage form further comprises a pharmaceutical binder. In some embodiments, the hormone, or analogue thereof, is selected from a gonadotrophin releasing hormone (GnRH) analogue including, but not limited to, triptorelin, leuprorelin and goserelin. In some embodiments, the hormone analogue is leuprorelin. In some embodiments, the acid is selected from citric acid, tartaric acid and an acid salt of an amino acid. In some embodiments, the single oral dosage form is a single tablet or capsule. In some embodiments, an average particle size of the coated acid particles is between 30 mesh and 140 mesh.

According to aspects illustrated herein, there is disclosed a solid oral dosage form of leuprolide that results in about 5% to about 10% absolute oral bioavailability. In some embodiments, a sufficient amount of active agent is included in the dosage form of the invention to achieve a serum level (Cmax) of the active agent of from about 45,000 to about 131,000 (pg/mL) (mg/kg).

In some embodiments, a solid oral dosage form comprising about 500 mg of citric acid and 50 mg of LLC is linear with respect to dose in the range of 1 mg to 3 mg of leuprolide.

According to aspects illustrated herein, there is disclosed a solid oral dosage form for oral delivery of a peptide active ingredient that includes a therapeutically effective amount of at least one peptide active ingredient; at least one pharmaceutically acceptable pH-lowering agent; an acid resistant protective vehicle; and a water-soluble barrier layer that separates the pH-lowering agent from the acid resistant protective vehicle. In some embodiments, the pH-lowering agent is present in the solid oral dosage form in a quantity which, if the solid oral dosage form were added to ten milliliters of 0.1M aqueous sodium bicarbonate solution, would be sufficient to lower the pH of said solution to no higher than 5.5. In some embodiments, the acid resistant protective vehicle is present at a weight which is from about 3.0% to about 10.0% of the weight of the remainder of the solid oral dosage form. In some embodiments, the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form. In some embodiments, the solid oral dosage form further includes an absorption enhancer. In some embodiments, the absorption enhancer is a surface active agent. In some embodiments, the surface active agent is absorbable or biodegradable. In some embodiments, the surface active agent is selected from the group consisting of acylcarnitines, phospholipids and bile acids. In some embodiments, the surface active agent is an acyl carnitine. In some embodiments, the solid oral dosage form further comprises a pharmaceutical binder. In some embodiments, the peptide active ingredient is human calcitonin. In some embodiments, the peptide active ingredient is salmon calcitonin. In some embodiments, the peptide active ingredient is eel calcitonin. In some embodiments, the pH-lowering agent is selected from citric acid, tartaric acid and an acid salt of an amino acid. In some embodiments, the single oral dosage form is a single tablet or capsule.

According to aspects illustrated herein, there is disclosed a solid oral dosage form that includes a therapeutically effective amount of at least one hormone or analogue thereof intermixed with coated acid particles, the coated acid particles comprising at least one pharmaceutically acceptable acid that is coated with a pharmaceutically acceptable protective coating to separate the acid from the hormone or analogue thereof in the solid oral dosage form; an acid resistant protective vehicle; and a water-soluble barrier layer that separates the pH-lowering agent from the acid resistant protective vehicle, wherein the hormone or analogue thereof and the coated acid particles are in the same layer of the solid oral dosage form, wherein total acid in the solid oral dosage form is in a quantity which, if added to ten milliliters of 0.1 M aqueous sodium bicarbonate solution, would be sufficient to lower the pH of the solution to no higher than 5.5. In some embodiments, the acid resistant protective vehicle is present at a weight which is from about 3.0% to about 10.0% of the weight of the remainder of the solid oral dosage form. In some embodiments the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form. In some embodiments, the solid oral dosage form further comprises a cellulose filler. In some embodiments, the solid oral dosage form further comprises an absorption enhancer. In some embodiments, the absorption enhancer is an acyl carnitine. In some embodiments, the absorption enhancer is lauroyl-L-carnitine. In some embodiments, the solid oral dosage form further comprises a pharmaceutical binder. In some embodiments, when the solid oral dosage form is ingested, the acid-resistant protective vehicle is breached in the intestine, the acid is released from the coated acid particles, and the acid reduces the activity of intestinal proteases. In some embodiments, the hormone or analogue thereof is selected from a gonadotrophin releasing hormone (GnRH) analogue including, but not limited to, triptorelin, leuprorelin and goserelin. In some embodiments, the hormone analogue is leuprorelin. In some embodiments, the acid is selected from citric acid, tartaric acid and an acid salt of an amino acid. In some embodiments, the single oral dosage form is a single tablet or capsule. In some embodiments, an average particle size of the coated acid particles is between 30 mesh and 140 mesh.

According to aspects illustrated herein, there is disclosed a solid oral dosage form that includes a therapeutically effective amount of at least one peptide active ingredient intermixed with coated acid particles, the coated acid particles comprising at least one pharmaceutically acceptable acid that is coated with a pharmaceutically acceptable protective coating to separate the acid from the peptide active ingredient in the solid oral dosage form; an acid resistant protective vehicle; and a water-soluble barrier layer that separates the pH-lowering agent from the acid resistant protective vehicle, wherein the peptide active ingredient and the coated acid particles are in the same layer of the solid oral dosage form, wherein total acid in the solid oral dosage form is in a quantity which, if added to ten milliliters of 0.1 M aqueous sodium bicarbonate solution, would be sufficient to lower the pH of the solution to no higher than 5.5. In some embodiments, the protective coating of the coated acid particles comprises maltodextrin. In some embodiments, the acid resistant protective vehicle is present at a weight which is from about 3.0% to about 10.0% of the weight of the remainder of the solid oral dosage form. In some embodiments, the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form. In some embodiments, the solid oral dosage form further comprises a cellulose filler. In some embodiments, the solid oral dosage form further comprises an absorption enhancer. In some embodiments, the absorption enhancer is an acyl carnitine. In some embodiments, the absorption enhancer is lauroyl-L-carnitine. In some embodiments, the solid oral dosage form further comprises a pharmaceutical binder. In some embodiments, when the solid oral dosage form is ingested, the acid-resistant protective vehicle is breached in the intestine, the acid is released from the coated acid particles, and the acid reduces the activity of intestinal proteases. In some embodiments, the peptide active ingredient is human calcitonin. In some embodiments, the peptide active ingredient is salmon calcitonin. In some embodiments, the peptide active ingredient is eel calcitonin. In some embodiments, the acid is selected from citric acid, tartaric acid and an acid salt of an amino acid. In some embodiments, the single oral dosage form is a single tablet or capsule. In some embodiments, an average particle size of the coated acid particles is between 30 mesh and 140 mesh.

According to aspects illustrated herein, there is disclosed a single dosage form for oral delivery of a hormone or analogue thereof comprising: (A) said hormone or analogue thereof; (B) at least one pharmaceutically acceptable acid wherein acid is present in said dosage form in a quantity which, if added to 10 milliliters of 0.1M aqueous sodium bicarbonate solution, would be sufficient to lower the pH of said solution to no higher than 5.5; (C) an acid resistant protective vehicle effective to transport said dosage form through the stomach of a patient while preventing contact between said hormone or analogue thereof and stomach proteases; and (D) a water soluble barrier layer that separates said acid from said protective vehicle; wherein said hormone or analogue thereof and said acid are in the same layer of said dosage form. In some embodiments, the total acid in the solid oral dosage form is in a quantity which, if added to ten milliliters of 0.1 M aqueous sodium bicarbonate solution, would be sufficient to lower the pH of the solution to no higher than 5.5. In some embodiments, the acid resistant protective vehicle is present at a weight which is from about 3.0% to about 10.0% of the weight of the remainder of the solid oral dosage form. In some embodiments, the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form. In some embodiments, the solid oral dosage form further comprises a cellulose filler. In some embodiments, the solid oral dosage form further comprises an absorption enhancer. In some embodiments, the absorption enhancer is an acyl carnitine. In some embodiments, the absorption enhancer is lauroyl-L-carnitine. In some embodiments, the solid oral dosage form further comprises a pharmaceutical binder. In some embodiments, when the solid oral dosage form is ingested, the acid-resistant protective vehicle is breached in the intestine, the acid is released from the coated acid particles, and the acid reduces the activity of intestinal proteases. In some embodiments, the hormone or analogue thereof is selected from a gonadotrophin releasing hormone (GnRH) analogue including, but not limited to, triptorelin, leuprorelin and goserelin. In some embodiments, the hormone analogue is leuprorelin.

According to aspects illustrated herein, there is disclosed a single dosage form for oral delivery of a peptide active ingredient comprising: (A) said peptide active ingredient; (B) at least one pharmaceutically acceptable acid wherein acid is present in said dosage form in a quantity which, if added to 10 milliliters of 0.1M aqueous sodium bicarbonate solution, would be sufficient to lower the pH of said solution to no higher than 5.5; (C) an acid resistant protective vehicle effective to transport said dosage form through the stomach of a patient while preventing contact between said peptide active ingredient and stomach proteases; and (D) a water soluble barrier layer that separates said acid from said protective vehicle; wherein said peptide active ingredient and said acid are in the same layer of said dosage form. In some embodiments, the total acid in the solid oral dosage form is in a quantity which, if added to ten milliliters of 0.1 M aqueous sodium bicarbonate solution, would be sufficient to lower the pH of the solution to no higher than 5.5. In some embodiments, the acid resistant protective vehicle is present at a weight which is from about 3.0% to about 10.0% of the weight of the remainder of the solid oral dosage form. In some embodiments, the acid resistant protective vehicle is present at a weight of about 3.6% of the weight of the remainder of the solid oral dosage form. In some embodiments, the acid resistant protective vehicle is present at a weight of about 7.0% of the weight of the remainder of the solid oral dosage form. In some embodiments, the acid resistant protective vehicle is present at a weight of about 10.0% of the weight of the remainder of the solid oral dosage form. In some embodiments, the water-soluble barrier layer is present at a weight which is from about 7.0% to about 12.0% of the weight of the remainder of the solid oral dosage form. In some embodiments, the water-soluble barrier layer is present at a weight of about 7.0% of the weight of the remainder of the solid oral dosage form. In some embodiments, the water-soluble barrier layer is present at a weight of about 12.0% of the weight of the remainder of the solid oral dosage form. In some embodiments, the amount of water-soluble barrier layer exceeds the amount of acid-protective vehicle.

In some embodiments, the solid oral dosage form further comprises a cellulose filler. In some embodiments, the solid oral dosage form further comprises an absorption enhancer. In some embodiments, the absorption enhancer is an acyl carnitine. In some embodiments, the absorption enhancer is lauroyl-L-carnitine. In some embodiments, the solid oral dosage form further comprises a pharmaceutical binder. In some embodiments, when the solid oral dosage form is ingested, the acid-resistant protective vehicle is breached in the intestine, the acid is released from the coated acid particles, and the acid reduces the activity of intestinal proteases. In some embodiments, the peptide active ingredient is human calcitonin. In some embodiments, the peptide active ingredient is salmon calcitonin. In some embodiments, the peptide active ingredient is eel calcitonin. In some embodiments, the acid is selected from citric acid, tartaric acid and an acid salt of an amino acid. In some embodiments, the single oral dosage form is a single tablet or capsule. In some embodiments, an average particle size of the coated acid particles is between 30 mesh and 140 mesh.

According to aspects illustrated herein, there is disclosed a pharmaceutical tablet for oral delivery of a physiologically active peptide agent comprising: (A) the active peptide agent; (B) L-lauroyl carnitine; (C) coated citric acid particles intermixed with the active peptide agent, wherein the coating separates the citric acid from the active peptide agent in the composition, wherein total citric acid, exclusive of coating, exceeds 100 milligrams per tablet; (D) at least one chymotrypsin inhibitor; (E) a cellulose filler; (F) a pharmaceutical binder; (G) an outer layer of an acid-resistant enteric coating effective to transport the pharmaceutical tablet through the stomach of a patient while preventing contact between the active peptide agent and stomach proteases; and (H) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone, and being present in an amount higher than three percent by weight relative to the total weight of the pharmaceutical, exclusive of the outer layer and the barrier layer, wherein the tablet has been compressed into tablet form such that the maximum weight loss during friability testing is no greater than 1%, and wherein the tablet reduces the activity of neutral to basic-acting proteases upon dissolution in the small intestine by reducing intestinal pH.

According to aspects illustrated herein, there is disclosed a pharmaceutical tablet for oral delivery of a hormone or analogue thereof comprising: (A) the hormone or analogue thereof; (B) L-lauroyl carnitine; (C) coated citric acid particles intermixed with the hormone or analogue thereof, wherein the coating separates the citric acid from the hormone or analogue thereof in the tablet, wherein total citric acid, exclusive of coating, exceeds 100 milligrams per tablet; (D) a cellulose filler; (E) a pharmaceutical binder; (F) an outer layer of an acid-resistant enteric coating effective to transport the pharmaceutical tablet through the stomach of a patient while preventing contact between the hormone or analogue thereof and stomach proteases; and (G) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone, and being present in an amount higher than three percent by weight relative to the total weight of the pharmaceutical tablet, exclusive of the outer layer and the barrier layer, wherein the tablet has been compressed into tablet form such that the maximum weight loss during friability testing is no greater than 1%, and wherein the tablet reduces the activity of neutral to basic-acting proteases upon dissolution in the small intestine by reducing intestinal pH.

According to aspects illustrated herein, there is disclosed a pharmaceutical tablet for oral delivery of a peptide active ingredient comprising: (A) the peptide active ingredient; (B) L-lauroyl carnitine; (C) coated citric acid particles intermixed with the peptide active ingredient, wherein the coating separates the citric acid from the peptide active ingredient in the tablet, wherein total citric acid, exclusive of coating, exceeds 100 milligrams per tablet; (D) a cellulose filler; (E) a pharmaceutical binder; (F) an outer layer of an acid-resistant enteric coating effective to transport the pharmaceutical tablet through the stomach of a patient while preventing contact between the peptide active ingredient and stomach proteases; and (G) a water soluble barrier layer beneath the outer layer of enteric coating that separates the enteric coating from the coated acid, the barrier layer comprising a compound selected from hydroxypropylmethylcellulose, hydroxypropylcellulose, methylcellulose and polyvinylpyrrolidone, and being present in an amount higher than three percent by weight relative to the total weight of the pharmaceutical tablet, exclusive of the outer layer and the barrier layer, wherein the tablet has been compressed into tablet form such that the maximum weight loss during friability testing is no greater than 1%, and wherein the tablet reduces the activity of neutral to basic-acting proteases upon dissolution in the small intestine by reducing intestinal pH.

According to aspects illustrated herein, there is disclosed a method of treating prostate cancer that includes orally administering to a subject in need thereof, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles.

According to aspects illustrated herein, there is disclosed a method of treating endometriosis that includes orally administering to a subject in need thereof, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles.

According to aspects illustrated herein, there is disclosed a method of treating uterine fibroids that includes orally administering to a subject in need thereof, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles.

According to aspects illustrated herein, there is disclosed a method of treating breast cancer that includes orally administering to a subject in need thereof, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles.

According to aspects illustrated herein, there is disclosed a method of treating precocious puberty that includes orally administering to a subject in need thereof, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles.

According to some aspects, disclosed herein are modified release solid oral compositions. In some embodiments, the modified release solid dosage composition comprise (a) a core comprising: (i) an effective amount of active pharmaceutical ingredient, (ii) a pH lowering agent, (iii) an absorption enhancer, (iv) a filler comprising an hydrogel-forming polymer, and (v) less than 10% by weight of disintegrant; and (b) an enteric coating surrounding the core, the composition providing a pharmacokinetic profile for the active agent with a $T_{lag}$ greater than 1.0 h and less than 16 h post-administration and a $T_{max}$ greater than ($T_{lag}$+0.5 h) and less than 20 h post-administration.

In some embodiments, the pharmacokinetic release profile targets release of the pharmaceutical active ingredient to the jejunum, the ileum or the jejunum and the ileum. In some embodiments, the composition is designed so that substantially no active pharmaceutical ingredient is released in the stomach, the duodenum or the stomach and duodenum post-administration.

In some embodiments, the composition further comprises a water soluble barrier beneath the enteric coating. In some embodiments, the water soluble barrier is in amount from about 6% to about 15% by weight. In some embodiments, the water soluble barrier is one of polyvinylpyrrolidone, hydroxymethylcellulose, hydroxypropylcellulose, methylcellulose and combinations thereof.

In some embodiments, the absorption enhancer has a critical micelle concentration of about 1.0 mM to about 40 mM. In some embodiments, the absorption enhancer has a critical micelle concentration of about 1.0 mM to about 15 mM.

In some embodiments, the hydrogel-forming polymer has a viscosity of about 3,000 to about 120,000 cP at 20° C. In some embodiments, the filler comprises microcrystalline cellulose, hydroxypropylcellulose, hydroxypropylmethylcellulose, chitosan or a combination thereof. In some embodiments, the hydrogel-forming polymer comprises hydroxypropylcellulose, hydroxypropylmethylcellulose or a combination thereof.

In some embodiments, the active pharmaceutical ingredient comprises a peptide or a peptidomimetic. In some embodiments, the peptide is one of leuprolide, insulin, vasopressin, calcitonin, calcitonin gene-related peptide, parathyroid hormone, desmopressin, gonadotrophin releasing hormone (GnRH), luteinizing hormone-releasing factor, erythropoietin, tissue plasminogen activators, human growth hormone, adrenocorticotropin, interleukins, enkephalin, glucagon-like peptide-1, desmopressin, 2,6-dimethyltyrosine-D-arginine-phenylalanine-lysine amide and analogs thereof.

In some embodiments, the active pharmaceutical ingredient comprises a small molecule. In some embodiments, the small molecule is classified as BCS Class II, BCS Class III or BCS Class IV. In some embodiments, the small molecule is one of tigecycline, zanamivir, kanamycin, tobramycin and fenofibrate.

In some embodiments, the absorption enhancer comprises a cationic surface active agent, an anionic surface active agent or a combination thereof. In some embodiments, the cationic surface active agent comprises an acylcarnitine. In some embodiments, the anionic surface active agent comprises sodium dodecyl sulfate. In some embodiments, the absorption enhancer comprises sodium dodecyl sulfate.

In some embodiments, the pH lowering agent comprises citric acid, tartaric acid or a combination thereof. In some embodiments, the pH lowering agent is in the form of coated acid particles. In some embodiments, the acid particles are coated with a water-soluble coating. In some embodiments, the pH lowering agent is in the form of coated citric acid particles. In some embodiments, the composition comprises from about 50 mg to about 500 mg of citric acid. In some embodiments, the composition comprises from about 250 mg to about 500 mg of citric acid. In some embodiments, the citric acid is in the form of coated citric acid.

In some embodiments, the composition comprises from about 5 mg/cm² to about 25 mg/cm² of enteric coating.

In some aspects, the modified release solid oral composition comprises (a) a core comprising: (i) an effective amount of active pharmaceutical ingredient, (ii) a pH lowering agent, (iii) an absorption enhancer, (iv) a filler comprising an hydrogel-forming polymer, wherein the core is substantially free of disintegrant; and (b) an enteric coating surrounding the core, wherein the composition provides a pharmacokinetic profile for the active agent with a $T_{lag}$ greater than 1.0 h and less than 16 h post-administration and a $T_{max}$ greater than ($T_{lag}$+0.5 h) and less than 20 h post-administration.

In some embodiments, the pharmacokinetic release profile targets release of the pharmaceutical active ingredient to the jejunum, the ileum or the jejunum and the ileum. In some embodiments, the composition is designed so that substantially no active pharmaceutical ingredient is released in the stomach, the duodenum or the stomach and duodenum post-administration.

In some embodiments, the composition further comprises a water soluble barrier beneath the enteric coating. In some embodiments, the water soluble barrier is in amount from about 6% to about 15% by weight. In some embodiments, the water soluble barrier is one of polyvinylpyrrolidone, hydroxymethylcellulose, hydroxypropylcellulose, methylcellulose and combinations thereof.

In some embodiments, the absorption enhancer has a critical micelle concentration of from about 1.0 to about 40 mM or of from about 1.0 to about 15 mM.

In some embodiments, the hydrogel-forming polymer has a viscosity of about 3,000 to about 120,000 cP at 20° C. In some embodiments, the filler comprises microcrystalline cellulose, hydroxypropylcellulose, hydroxypropylmethylcellulose, chitosan or a combination thereof. In some embodiments, the hydrogel-forming polymer comprises hydroxypropylcellulose, hydroxypropylmethylcellulose or a combination thereof.

In some embodiments, the active pharmaceutical ingredient comprises a peptide or a peptidomimetic. In some embodiments, the peptide is one of leuprolide, insulin, vasopressin, calcitonin, calcitonin gene-related peptide, parathyroid hormone, desmopressin, gonadotrophin releasing hormone (GnRH), luteinizing hormone-releasing factor, erythropoietin, tissue plasminogen activators, human growth hormone, adrenocorticotropin, interleukins, enkephalin, glucagon-like peptide-1, desmopressin, 2,6-dimethyltyrosine-D-arginine-phenylalanine-lysine amide and analogs thereof.

In some embodiments, the active pharmaceutical ingredient comprises a small molecule. In some embodiments, the small molecule is classified as BCS Class II, BCS Class III or BCS Class IV. In some embodiments, the small molecule is one of tigecycline, zanamivir, kanamycin, tobramycin and fenofibrate.

In some embodiments, the absorption enhancer comprises a cationic surface active agent, an anionic surface active agent or a combination thereof. In some embodiments, the cationic surface active agent comprises an acylcarnitine. In some embodiments, the anionic surface active agent comprises sodium dodecyl sulfate. In some embodiments, the absorption enhancer comprises sodium dodecyl sulfate.

In some embodiments, the pH lowering agent comprises citric acid, tartaric acid or a combination thereof. In some embodiments, the pH lowering agent is in the form of coated acid particles. In some embodiments, the acid particles are coated with a water-soluble coating. In some embodiments, the pH lowering agent is in the form of coated citric acid particles. In some embodiments, the composition comprises from about 50 mg to about 500 mg of citric acid. In some embodiments, the composition comprises from about 250 mg to about 500 mg of citric acid. In some embodiments, the citric acid is in the form of coated citric acid.

In some embodiments, the composition comprises from about 5 mg/cm$^2$ to about 25 mg/cm$^2$ of enteric coating.

Methods of Treatment

Some aspects relate to methods of treating a patient are disclosed. In some embodiments, the method of treating comprises (a) providing a solid oral dosage form comprising (i) a core comprising an effective amount of active pharmaceutical ingredient, a pH lowering agent, an absorption enhancer, a filler comprising an hydrogel-forming polymer, and less than 10% by weight of disintegrant; and (ii) an enteric coating surrounding the core; and (b) administering orally to a patient, the solid oral dosage form, wherein the solid oral dosage form provides a pharmacokinetic release profile for the active agent with a $T_{lag}$ greater than 1.0 h and less than 16 h post-administration and a $T_{max}$ greater than ($T_{lag}$+0.5 h) and less than 20 h post-administration.

In some embodiments, the pharmacokinetic release profile targets release of the pharmaceutical active ingredient to the jejunum, the ileum or the jejunum and the ileum.

In some embodiments, the solid oral dosage form is substantially free of disintegrant. In some embodiments, the solid oral dosage form further comprises a water soluble barrier beneath the enteric coating.

In some embodiments, the absorption enhancer has a critical micelle concentration of about 1.0 to about 40 mM. In some embodiments, the absorption enhancer has a critical micelle concentration of about 1.0 to about 15 mM.

In some embodiments, the hydrogel-forming polymer has a viscosity of about 3,000 to about 120,000 cP at 20° C. In some embodiments, the filler comprises microcrystalline cellulose, hydroxypropyl cellulose, hydroxypropyl methyl cellulose, chitosan or a combination thereof. In some embodiments, the hydrogel-forming polymer comprises hydroxypropyl cellulose, hydroxypropyl methyl cellulose or a combination thereof.

In some embodiments, the active pharmaceutical ingredient comprises a peptide or a peptidomimetic. In some embodiments, the peptide is one of leuprolide, insulin, vasopressin, calcitonin, calcitonin gene-related peptide, parathyroid hormone, desmopressin, gonadotrophin releasing hormone (GnRH), luteinizing hormone-releasing factor, erythropoietin, tissue plasminogen activators, human growth hormone, adrenocorticotropin, interleukins, enkephalin, glucagon-like peptide-1, desmopressin, 2,6-dimethyltyrosine-D-arginine-phenylalanine-lysine amide and analogs thereof.

In some embodiments, the active pharmaceutical ingredient comprises a small molecule. In some embodiments, the small molecule is classified as BCS Class II, BCS Class III or BCS Class IV. In some embodiments, the small molecule is one of tigecycline, zanamivir, kanamycin, tobramycin and fenofibrate.

In some embodiments, the absorption enhancer comprises a cationic surface active agent, an anionic surface active agent or a combination thereof. In some embodiments, the cationic surface active agent comprises an acylcarnitine. In some embodiments, the anionic surface active agent comprises sodium dodecyl sulfate. In some embodiments, the absorption enhancer comprises sodium dodecyl sulfate.

In some embodiments, the pH lowering agent comprises citric acid, tartaric acid or a combination thereof. In some embodiments, the pH lowering agent is in the form of coated acid particles. In some embodiments, the acid particles are coated with a water-soluble coating. In some embodiments, the pH lowering agent is in the form of coated citric acid particles. In some embodiments, the composition comprises from about 50 mg to about 500 mg of citric acid. In some embodiments, the composition comprises from about 250 mg to about 500 mg of citric acid. In some embodiments, the citric acid is in the form of coated citric acid.

In some embodiments, the composition comprises from about 5 mg/cm$^2$ to about 25 mg/cm$^2$ of enteric coating.

The compositions of the invention may be administered orally in an effective amount within the dosage ranges described herein in a regimen of single or multiple (twice, etc.) daily or single or multiple weekly doses. In some embodiments, the compositions of the invention may be administered orally in an effective amount for a suitable period of time to treat a disease in a subject in need thereof. As used herein, the term "a suitable period of time" refers to the period of time starting when a subject begins treatment for a condition using a method of the present disclosure, throughout the treatment, and up until when the subject stops treatment due to either a reduction in symptoms associated with the condition or due to a laboratory diagnosis indicating that the condition is under control. In an embodiment, a suitable period of time is one (1) week. In some embodiments, a suitable period of time is between one (1) week and two (2) weeks. In some embodiments, a suitable period of time is two (2) weeks. In some embodiments, a suitable period of time is between two (2) weeks and three (3) weeks. In some embodiments, a suitable period of time is three (3) weeks. In an embodiment, a suitable period of time is between three (3) weeks and four (4) weeks. In an embodiment, a suitable period of time is four (4) weeks. In some embodiments, a suitable period of time is between four (4) weeks and five (5) weeks. In some embodiments, a suitable period of time is five (5) weeks. In some embodiments, a suitable period of time is between five (5) weeks and six (6) weeks. In some embodiments, a suitable period of time is six (6) weeks. In some embodiments, a suitable period of time is between six (6) weeks and seven (7) weeks. In some embodiments, a suitable period of time is seven (7) weeks. In some embodiments, a suitable period of time is between seven (7) weeks and eight (8) weeks. In some embodiments, a suitable period of time is eight (8) weeks. In some embodiments, a suitable period of time is between one (1) month and eight (8) months. In some embodiments, a suitable period of time is between two (2) months and six (6) months. In some embodiments, a suitable period of time is between three (3) months and five (5) months.

According to aspects of the invention, the compositions of the present invention provide the predictable delivery of an active agent with surprisingly low inter-subject variability in terms of maximum plasma concentration ($C_{max}$) and the time to reach the maximum plasma concentration ($T_{max}$). In some embodiments, the delivery of the therapeutic agent optimizes absorption beyond the duodenum.

In some embodiments, the solid oral dosage form in accordance with the present disclosure may be used to treat patients who suffer from disease states including, but not limited to, bacterial or viral infectious diseases, metabolic disorders, cardiovascular, neurological, endocrine, pulmonary, or oncological diseases.

In some embodiments, a solid oral dosage form of a gonadotrophin releasing hormone (GnRH) analogue in accordance with the present disclosure may be used to treat patients who suffer from hormone-responsive cancers. The present disclosure may be used, for example, to treat prostate cancer or breast cancer. In a specific embodiment of the present disclosure, a solid oral dosage form of a GnRH analogue in accordance with the present disclosure may be used to treat patients who suffer from estrogen-dependent conditions. The present disclosure may be used, for example, to treat endometriosis or uterine fibroids, to treat precocious puberty, and to control ovarian stimulation in In Vitro Fertilization.

According to aspects illustrated herein, a patient having prostate cancer can be treated with a solid oral dosage form of the present disclosure. In an embodiment, such treatment includes orally administering the patient, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles. In exemplary embodiments, amounts of leuprolide that may be administered to a patient being treated for prostate cancer can measure between 1-20 mg per day, once or twice daily, for 4, 12, 16 or 24 weeks and continued as necessary.

According to aspects illustrated herein, a patient having endometriosis can be treated with a solid oral dosage form of the present disclosure. In an embodiment, such treatment includes orally administering the patient, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles. In exemplary embodiments, amounts of leuprolide that may be administered to a patient being treated for endometriosis can measure between 0.5-20 mg per day, once or twice daily, for up to 6 months.

According to aspects illustrated herein, a patient having uterine fibroids can be treated with a solid oral dosage form of the present disclosure. In an embodiment, such treatment includes orally administering the patient, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles. In exemplary embodiments, amounts of leuprolide that may be administered to a patient being treated for uterine fibroids can measure between 0.5-20 mg per day, once or twice daily, for up to 3 months.

According to aspects illustrated herein, a patient having breast cancer can be treated with a solid oral dosage form of the present disclosure. In an embodiment, such treatment includes orally administering the patient, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles. In exemplary embodiments, amounts of leuprolide that may be administered to a patient being treated for breast cancer can measure between 0.5-20 mg per day, once or twice daily, for up to 24 months.

According to aspects illustrated herein, a patient having precocious puberty can be treated with a solid oral dosage form of the present disclosure. In an embodiment, such treatment includes orally administering the patient, for a suitable period of time, a pharmaceutical tablet that includes (A) a gonadotrophin releasing hormone (GnRH) analogue; (B) an absorption enhancer; (C) coated acid particles intermixed with the GnRH analogue, wherein the coating separates the citric acid from the GnRH analogue in the tablet; (D) an outer layer of an acid-resistant enteric coating effective to transport the pharmaceutical tablet through the stomach of a patient while preventing contact between the GnRH analogue and stomach proteases; and (E) a water soluble barrier layer beneath the outer layer of enteric coating that separates the enteric coating from the coated acid particles. In exemplary embodiments, amounts of leuprolide that may be administered to a patient being treated for precocious puberty can measure between 1-40 mg per day, once or twice daily. Treatment should be continued until the appropriate age of the onset of puberty, at the discretion of the physician.

EXAMPLES

Example 1

Enteric Coat Film Layer Thickness

Tablets were manufactured with varying amounts of the functional excipient citric acid, with and without lauroyl-L-carnitine (LLC). A non-enhanced tablet, Prototype D, was manufactured with no functional excipients. The cores were seal coated with an immediate release water-soluble film barrier layer and then enteric coated. Briefly, the drug substance and active excipients were dry-blended with inert excipients (binder, filler, disintegrant), lubricant was added (magnesium stearate) and then directly compressed into tablet cores using a hand press.

Prototype E was formulated to dissolve slowly upon transition to the neutral medium, but otherwise similar to Prototype C. Prototype G was formulated to dissolve rapidly upon transition to the neutral medium, but otherwise similar to Prototype C. The results of Prototype C served as the center-point.

Table 1 shows the tablet formulations active excipient contents. The coating quantities are described in terms of weight/surface area, primarily for scaling and comparison to different sized tablets, and also in terms of overall weight gain, which is calculated based on the targeted weight/surface area value on a per-batch basis.

TABLE 1

Tablet Formulations Active Excipient Contents

| Item | Prototype Tablet A | Prototype Tablet B | Prototype Tablet C | Prototype Tablet D | Prototype Tablet E (SLOW) | Prototype Tablet G (FAST) |
|---|---|---|---|---|---|---|
| Leuprolide | 3 mg | 1 mg | 3 mg | 3 mg | 3 mg | 3 mg |
| Citric Acid | 500 mg | 500 mg | 250 mg | None | 250 mg | 250 mg |
| Lauroyl-L-Carnitine | 50 mg | 50 mg | 50 mg | None | 50 mg | 50 mg |
| Immediate Release Coat | 19 mg/cm$^2$ (10% weight gain) | 19 mg/cm$^2$ (10% weight gain) | 19 mg/cm$^2$ (12% weight gain) | 19 mg/cm$^2$ (12% weight gain) | 19 mg/cm$^2$ (12% weight gain) | 11 mg/cm$^2$ (7% weight gain) |
| Enteric Coat | 10 mg/cm$^2$ (6% weight gain) | 10 mg/cm$^2$ (6% weight gain) | 10 mg/cm$^2$ (7% weight gain) | 10 mg/cm$^2$ (7% weight gain) | 15 mg/cm$^2$ (10% weight gain) | 5 mg/cm$^2$ (3.6% weight gain) |

Methods of Manufacturing

Any suitable methods can be used to mix the formulation comprising the API. In some embodiments, the solid dosage form is a tablet or the like. In some embodiments, the core of the solid dosage form can be manufactured with varying amounts of the active agent, active excipients (pH lowering agent, permeation enhancer), binder/filler, and with or without disintegrant. In some embodiments, the core can be seal coated with an immediate release water-soluble film barrier layer and then enteric coated.

In some embodiments, the API and active excipients were dry-blended with inert excipients (binder, filler, optionally disintegrant), lubricant was optimally added and then directly compressed into tablet cores or the like using a hand press.

In some embodiments, the solid dosage forms are tablets and the tablets can be tested for in-process tests (weight, hardness, friability, disintegration time), then coated with immediate-release coating followed by enteric coating.

The invention is further illustrated by the following non-limiting examples.

Tableting In-Process Controls

In-process characterizations during tableting operations were performed according the following USP compendial tests:
 USP<1216> Tablet Friability (Distek model DF3 Automated Friabilator)
 USP<1217> Tablet Breaking Force (Pharmatron model 6D or MT50 Tablet Testers)
 USP<701> Disintegration, method described for uncoated tablets (Distek 3100 series bathless disintegration system)

Assay of Tablets and SC Solution by RP-HPLC

The method involves a gradient elution of leuprolide using a C18 column and Water/MeCN/IPA/TFA buffer system with detection at 220 nm, see Table 2.

Diluent: 3.33 mg/mL lauroyl-L-carnitine in water.

3 mg Tablet Standard: Dilute reference standard (1.0 mg/mL) to 0.2 mg/mL with Diluent.

1 mg Tablet Standard: Dilute reference standard (1.0 mg/mL) to 0.067 mg/mL with Diluent.

Tablet Extraction: An individual tablet was added to a tared vial and weighed. For tablets containing LLC in the formulation, the tablet was crushed in the same vial and 15 mL of water was added. For the unformulated tablets (without LLC), Diluent was used in place of water. The mixtures were placed on a stir plate and mixed for 30 minutes. Approximately 2 mL of the mixture was transferred to a polypropylene microtube and clarified by centrifugation.

Tablet Assay Calculation: The assay of each test article was measured relative to the responses in the working standards. Tablet soluble matter and extract solution density were considered in the calculations.

SC Solution Standard: Reference standard (1.0 mg/mL) was diluted 1:10 using a solution of 0.9% sodium chloride.

SC Test Article: Inject neat.

TABLE 2

| HPLC Method | |
|---|---|
| Stationary Phase | Proto 200 C18 5 μm, 100 × 2.1 mm (Higgins Analytical PN RS-10210D185) |
| Mobile Phase A | 5% acetonitrile, 0.1% trifluoroacetic acid |
| Mobile Phase B | 70% acetonitrile, 20% 2-propanol, 0.07% trifluoroacetic acid |
| Column Temperature | 50° C. |
| Flow Rate | 1.2 mL/minute |
| Run Time | 6 minutes |
| Detection | 220 nm |
| Injection Volume | 7 μL for 3 mg tablet assay, 20 μL for 1 mg tablet assay, and 15 μL for SC solution assay |

| | Time | % Mobile Phase B |
|---|---|---|
| Time Program | 0.0 | 20% |
| | 3.5 | 30% |
| | 3.6 | 100% |
| | 5.0 | 100% |
| | 5.1 | 20% |
| | 6.0 | 20% |

Figure 2:
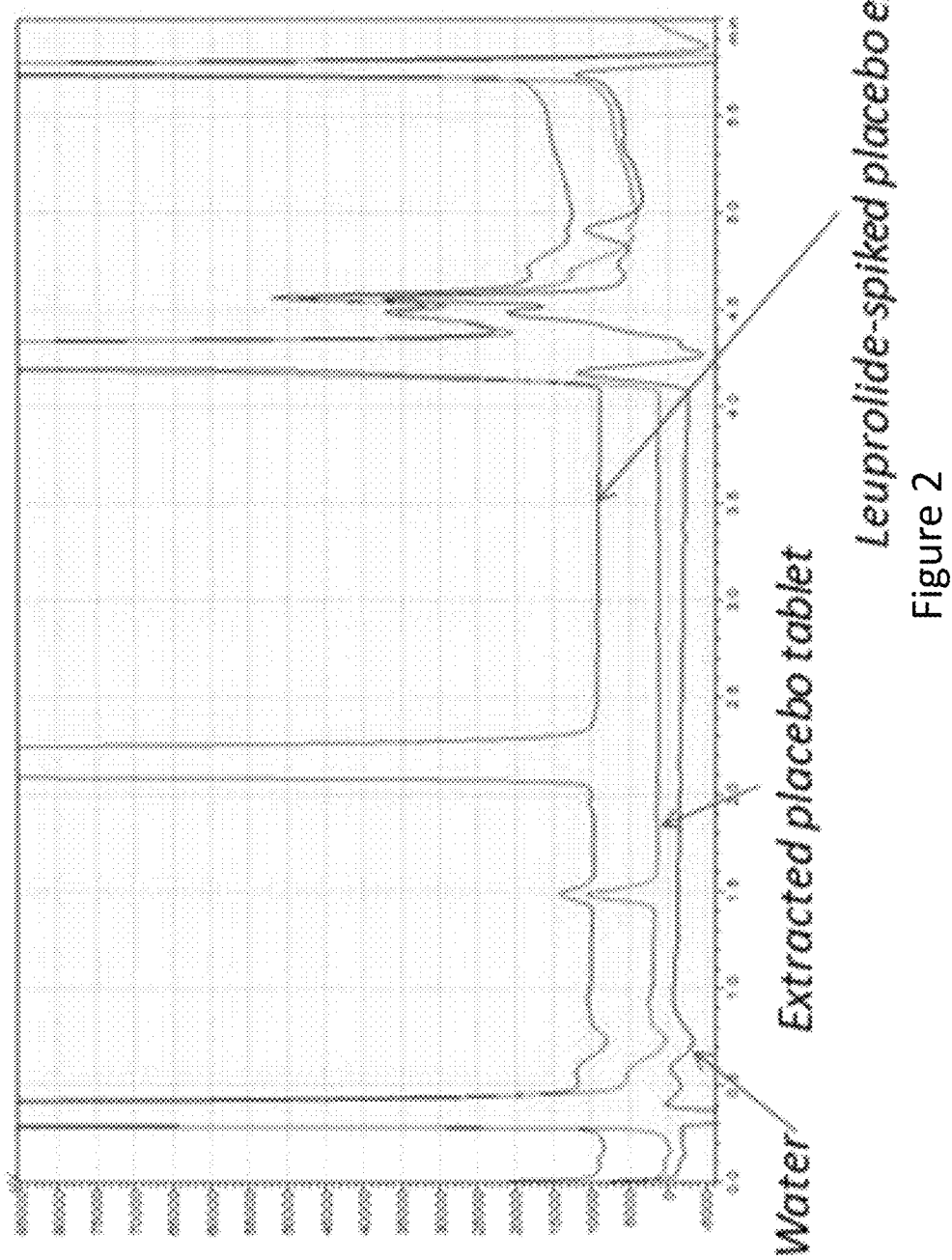
FIG. 2 shows RP-HPLC chromatograms of water, extracted placebo tablet, and leuprolide-spiked placebo extract.
Figure 3:
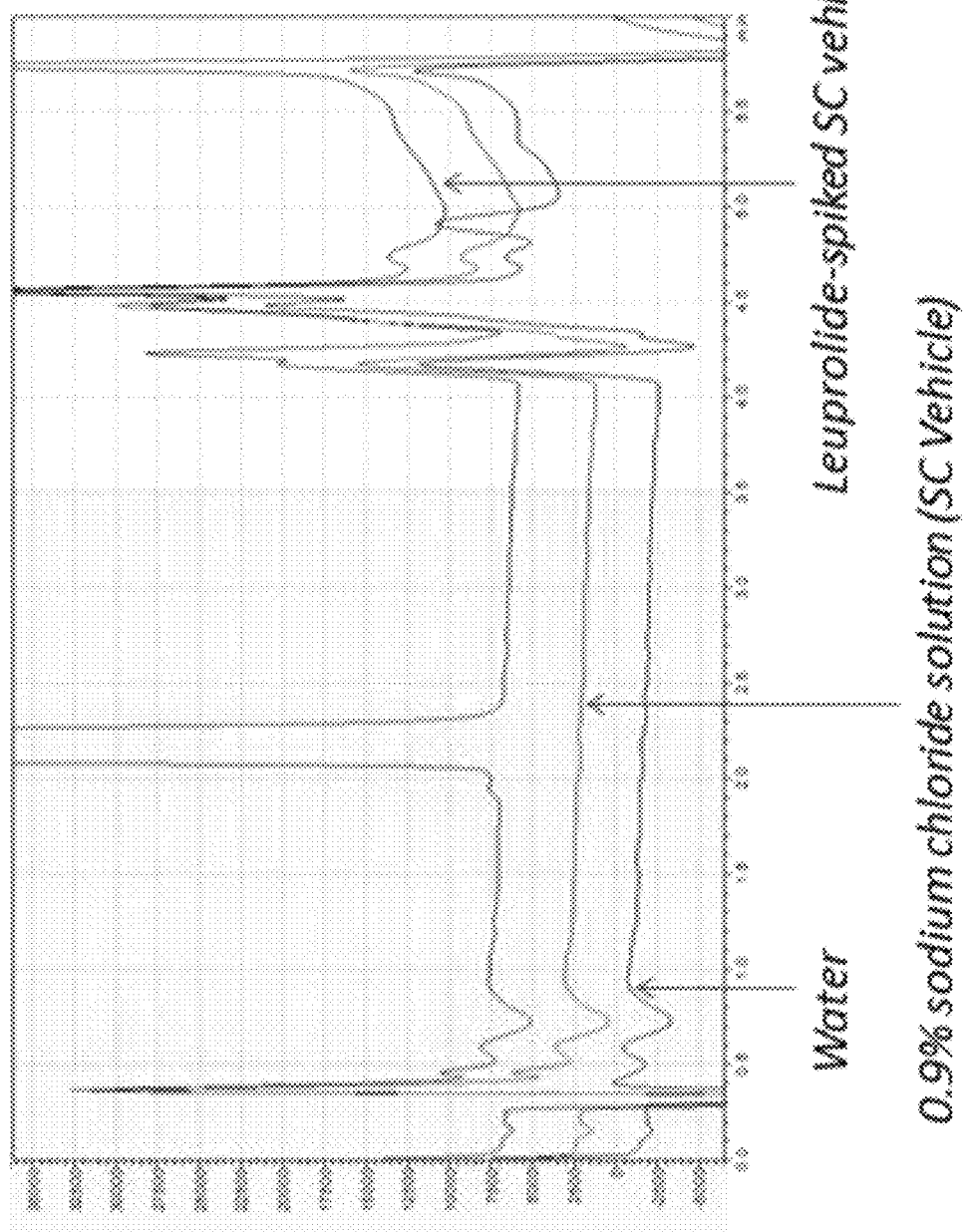
FIG. 3 shows RP-HPLC chromatograms of water, 0.9% sodium chloride solution (SC vehicle), and leuprolide-spiked SC vehicle.

A rapid RP-HPLC method for leuprolide assay was developed utilizing an aqueous/acetonitrile/2-propanol/TFA solvent system and a C18 stationary phase. The method demonstrated linearity across a wide range of column loads indicating suitability for the analysis of test articles at various concentrations (see FIG. 1) The same method was used for determining assay of the SC solution and tablet assay and content uniformity with only minor modifications to injection volumes and standard preparations. For reference, the column loads for SC and Tablet test articles ranged from 1.33 to 1.5 μg. Representative chromatograms are provided in FIG. 2 and FIG. 3. Overlaid with blank injections, the figures demonstrate that leuprolide is fully resolved from any potentially interfering peaks in the tablet and vehicle matrices. Leuprolide elutes at about 2.2 minutes Dissolution Method The dissolution procedure was performed according to USP chapter<711>, Apparatus 2 (paddles) for Delayed Release Dosage Forms. The acid stage was conducted in 300 mL of 0.1 N hydrochloric acid with a 50 rpm paddle speed for 120 minutes. The buffer stage was performed using 500 mL of 50 mM phosphate, pH 6.8, with a paddle speed of 50 rpm for 60 minutes (plus an infinity time point). Samples were taken at the end of the acid stage and after 10, 20, 30, 45 and 60 minutes in the buffer stage and after the infinity time point. Samples were assayed according to a rapid RP-HPLC method described above with modifications to the standard preparations and injection volumes to accommodate the more dilute solutions.

The subcutaneous (SC) comparator was formulated to a final concentration of 0.1 mg/mL in an isotonic sodium chloride solution. Briefly, leuprolide acetate was dissolved in 0.9% sodium chloride to a concentration of 0.1 mg/mL, and stored refrigerated. The comparator was shipped to the animal test site on ice and sterile filtered immediately prior to dosing of the dogs. The formulation was tested during the week before dosing and again upon return of the remaining solution. A summary of the analytical test results is presented in Table 3.

TABLE 3

| Subcutaneous (SC) Formulation and Dose | | |
|---|---|---|
| Formulation | Assay Date | Concentration (mg/mL) |
| 0.1 mg/mL Leuprolide in 0.9% Sodium Chloride | before dosing after dosing | 0.1010 0.1006 |

The tablets were characterized by in-process and final product tests as follows:

In process tests: friability, breaking force, disintegration time

Final product tests: content uniformity, assay (calculated from CU), dissolution.

The stability of the prototypes was confirmed after dosing (testing for assay only).

The concentration of a SQ solution was verified before and after administration.

A small quantity of tablets from Prototype A (3 mg strength, 500 mg citric acid and 50 mg LLC) were packaged in HDPE bottles with desiccant and tested placed in a brief stability study (6 months, 5° C. and 25° C., assay and degradation, only).

The tablets were analyzed for assay, content uniformity and dissolution (acid stage and buffer stage). The assay and content uniformity results are summarized in Table 4A and 4B, and indicate good overall recovery and excellent content uniformity.

TABLE 4A

| Assay and Content Uniformity of tablets in Prototypes A-D | | | | | | | | |
|---|---|---|---|---|---|---|---|---|
| | Prototype A | | Prototype B | | Prototype C | | Prototype D | |
| Unit No. | mg/unit | % LC (3 mg) | mg/unit | % LC (1 mg) | mg/unit | % LC (3 mg) | mg/unit | % LC (3 mg) |
| 1 | 2.91 | 97.1% | 0.98 | 98.4% | 2.70 | 89.9% | 2.93 | 97.7% |
| 2 | 2.88 | 95.9% | 0.97 | 96.5% | 2.52 | 84.1% | 2.63 | 87.7% |
| 3 | 2.85 | 95.0% | 0.94 | 93.9% | 2.77 | 92.2% | 2.83 | 94.3% |
| 4 | 2.88 | 95.9% | 0.96 | 95.6% | 2.76 | 91.9% | 2.87 | 95.6% |

TABLE 4A-continued

Assay and Content Uniformity of tablets in Prototypes A-D

| Unit No. | Prototype A | | Prototype B | | Prototype C | | Prototype D | |
|---|---|---|---|---|---|---|---|---|
| | mg/unit | % LC (3 mg) | mg/unit | % LC (1 mg) | mg/unit | % LC (3 mg) | mg/unit | % LC (3 mg) |
| 5 | 2.90 | 96.8% | 0.99 | 99.2% | 2.80 | 93.5% | 2.84 | 94.8% |
| 6 | 2.87 | 95.7% | 0.91 | 91.3% | 2.78 | 92.8% | 2.90 | 96.6% |
| 7 | 2.90 | 96.8% | 0.99 | 98.6% | 2.87 | 95.6% | 2.92 | 97.3% |
| 8 | 2.85 | 95.0% | 0.98 | 98.3% | 2.52 | 83.9% | 2.90 | 96.6% |
| 9 | 2.88 | 95.9% | 0.95 | 95.1% | 2.70 | 89.9% | 2.86 | 95.3% |
| 10 | 2.91 | 97.1% | 0.97 | 97.5% | 2.53 | 84.5% | 2.81 | 93.7% |
| Average | 2.88 | 96.1% | 0.96 | 96.4% | 2.69 | 89.8% | 2.85 | 95.0% |
| SD | 0.02 | 0.8% | 0.03 | 2.5% | 0.13 | 4.2% | 0.09 | 2.9% |

The assay and content uniformity results for the coated prototype E tablets are summarized in Table 4B, and indicate good overall recovery and excellent content uniformity. Because prototype G was made from the same tablet cores as prototype E, the assay and uniformity was assigned to both batches.

TABLE 4B

Assay and Content Uniformity of Tablet in Prototypes E/G

| Sample | mg/Tablet | % LC |
|---|---|---|
| Leuprolide Prototype E-CU1 | 2.77 | 92.3% |
| Leuprolide Prototype E-CU2 | 2.76 | 92.0% |
| Leuprolide Prototype E-CU3 | 2.91 | 96.9% |
| Leuprolide Prototype E-CU4 | 2.75 | 91.5% |
| Leuprolide Prototype E-CU5 | 2.73 | 90.9% |
| Leuprolide Prototype E-CU6 | 2.69 | 89.5% |
| Leuprolide Prototype E-CU7 | 2.80 | 93.4% |
| Leuprolide Prototype E-CU8 | 3.02 | 100.6% |
| Leuprolide Prototype E-CU9 | 2.64 | 88.1% |
| Leuprolide Prototype E-CU10 | 2.80 | 93.4% |
| Average: | 2.79 | 92.9% |
| SD: | 0.11 | 3.6% |

Figure 4:
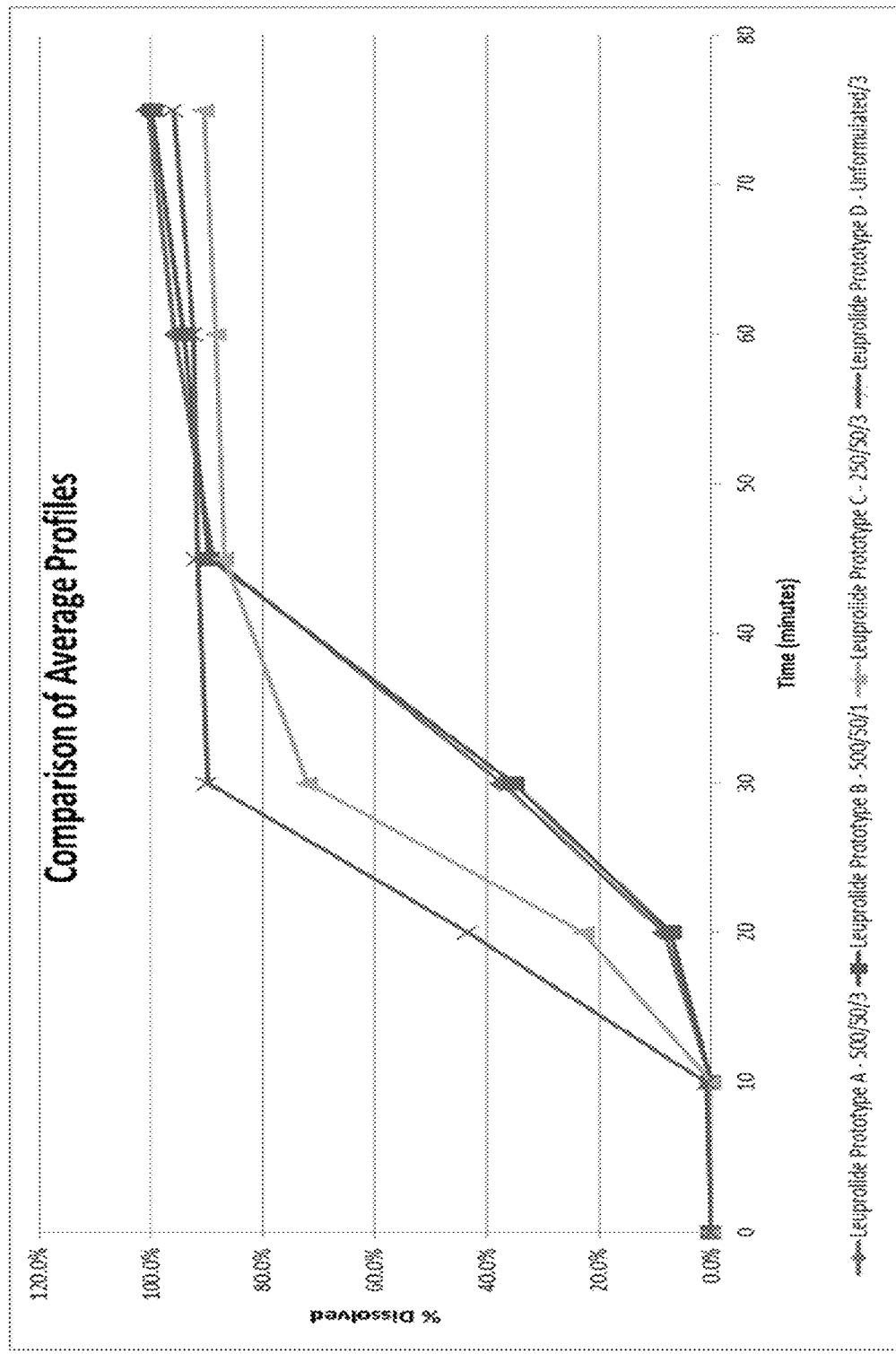
FIG. 4 shows average dissolution profiles of various leuprolide tablets of the present disclosure.
Figure 5:
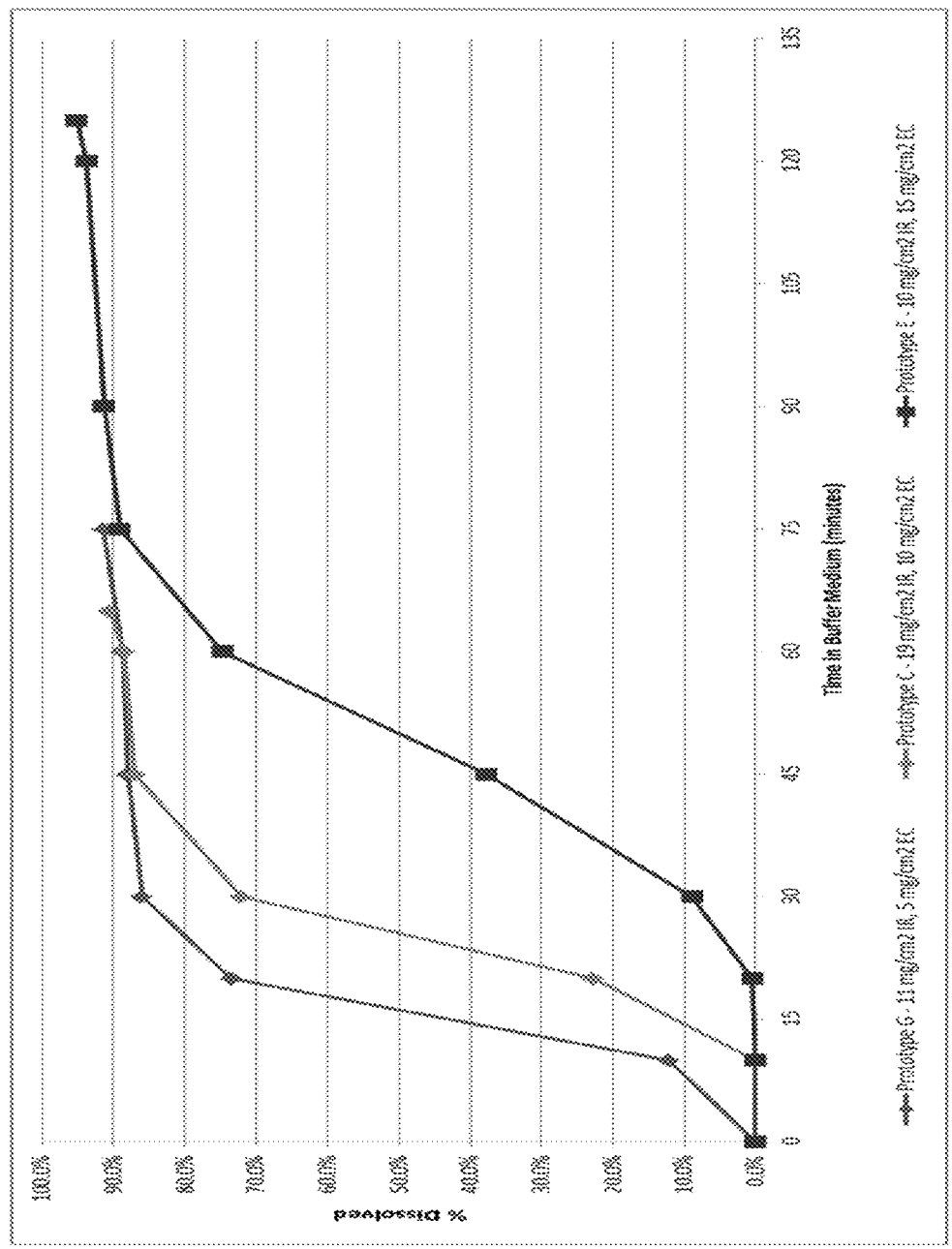
FIG. 5 shows average dissolution profiles of various leuprolide tablets of the present disclosure.
Figure 6:
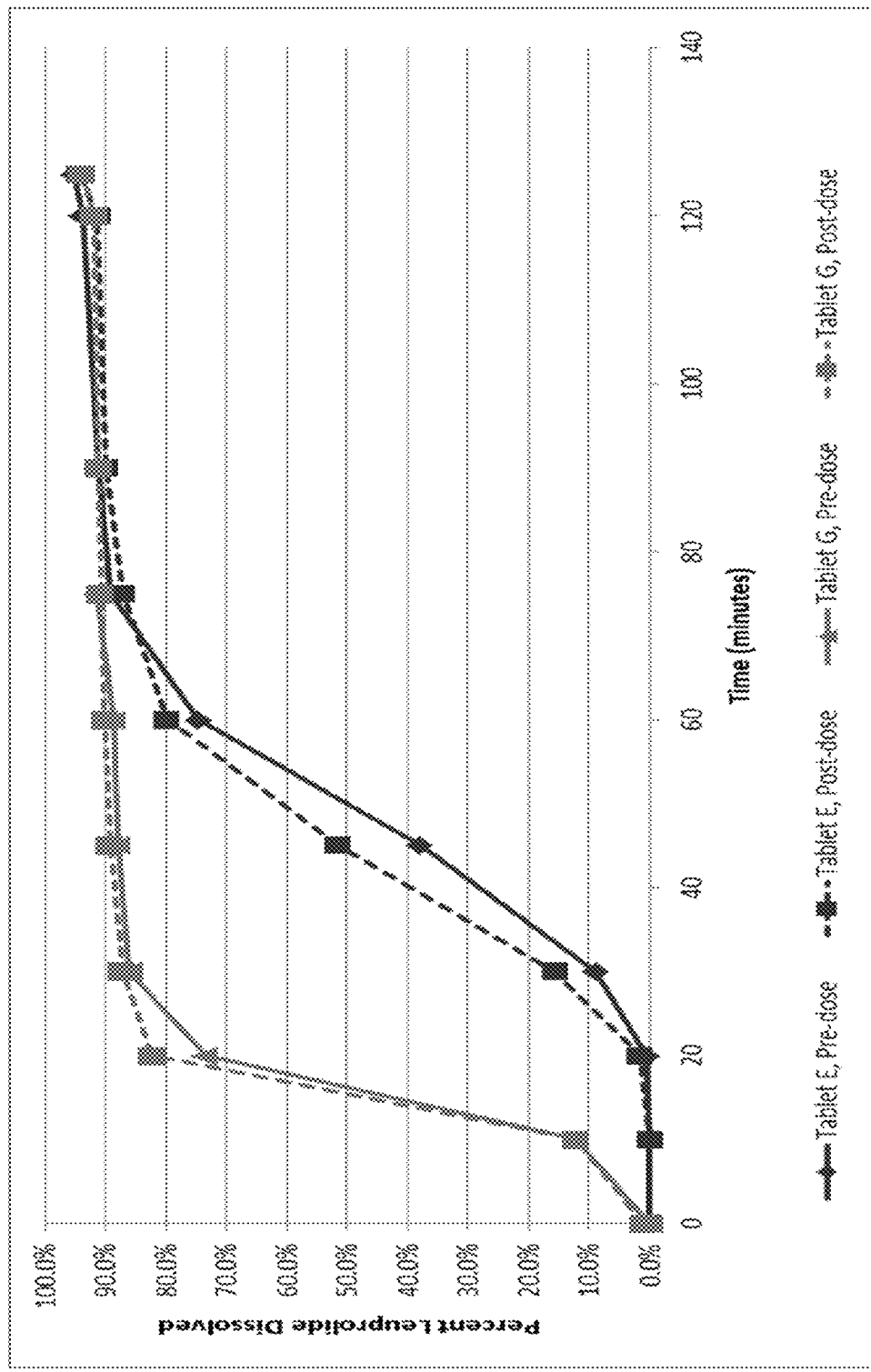
FIG. 6 shows stability of various leuprolide tablets of the present disclosure.

The dissolution results for each batch are summarized in FIGS. 4 and 5. The results confirm acid resistance of all batches (reported at 0 minutes) and larger tablets dissolve at a slower rate. The tablets were stored refrigerated and shipped to the animal test site on ice. Extra tablets were returned for dose verification as summarized in Table 5 and FIG. 6. The data indicate that the dissolution profiles and final percent dissolved (assays) were not significantly affected by time or shipping. The test articles were stable for the duration of the study.

TABLE 5

Prototype Tablet Dose Verification/Assay Stability

| | Prototype Tablet A (ULB-231/035) | Prototype Tablet B (ULB-231/036) | Prototype Tablet C (ULB-231/037) | Prototype Tablet D (ULB-231/038) |
|---|---|---|---|---|
| Leuprolide/tablet at release | 2.88 mg | 0.96 mg | 2.69 mg | 2.85 mg |
| Leuprolide/tablet after dosing | 2.91 mg | 0.95 mg | 2.68 mg | 2.84 mg |

In Vivo Studies

This study evaluated the pharmacokinetics of leuprolide in dogs following a single subcutaneous (SC) dose (0.01 mg/kg) and single oral doses of enteric-coated tablets containing either 1 mg or 3 mg amounts of leuprolide with various amounts of excipients. The active excipients evaluated were lauroyl-L-carnitine (LLC) and citric acid. The parameters examined were ratios of citric acid to LLC and the absolute amount of citric acid. An unformulated tablet (no citric acid, no LLC) was included as a control.

Materials and Methods

Drug Substance

A 2.0 gram quantity of Leuprolide Acetate, GMP quality, was purchased and received from PolyPeptide Group.

Reference Standard

Approximately 60 mg of Leuprolide Acetate was used to establish a 1 mg/mL aqueous reference standard.

Analytical Development

A commercially available ELISA kit was qualified for measuring concentrations of Leuprolide in plasma samples. A rapid HPLC method was developed to measure leuprolide content in assay, content uniformity and dissolution (by USP<711>) samples of the tablet prototype test articles.

Each prototype was evaluated by dosing a single tablet in beagle dogs. Six dogs were dosed for prototypes A, B, C, E and G and three dogs were dosed for prototype D. [plus 3 dogs for SQ =24 dogs total] Plasma samples were collected over a 24 hour period, with time points: pre-dose, 0.5, 1, 1.33, 1.66, 2, 2.33, 2.66, 3, 3.33, 3.66, 4, 6, 8, 12 and 24 hours. [16 samples/dog×21 dogs=336 samples]

Animals

Adult beagle dogs weighing approximately 8 to 16 kg were used in the study. Primary enclosures were specified in the USDA Welfare Act (9 CFR Parts 1, 2, and 3) and as described in the Guide for the Care and Use of Laboratory Animals (National Academy Press, Washington, S.C., 1996). A 12-hour light/12-hour dark photoperiod was maintained. Room temperature was set to be maintained at approximately 20+5° C. Relative humidity was monitored, but not controlled. Animal room and pen cleaning were performed according to testing facility (Sinclair) standard operating procedures (SOPs).

Purina® Dog Chow Canine Diet was provided once daily in amounts (~250 g) appropriate for the size and age of the animals. Tap water was available ad libitum via automatic watering device or water bowls. Animals were fasted overnight prior to drug administration and fed six hours after dosing.

Doses and Route of Administration

Subcutaneous doses of leuprolide were administered as a bolus injection into beagle dogs at a dose volume of 0.1 mL/kg. For a 10 kg dog, this would result in a dose of 0.1 mg. Oral dosing of tablets was accomplished by administering them to the back of the dog's mouth followed with 1.0 mL/kg of water.

Study Design and Pharmacokinetic Sample Collection

Adult beagle dogs were each dosed with tablet prototypes A, B, C, E or G. During a subsequent phase, three dogs were dosed with the SC formulation.

Prior to the study, the dogs were fasted overnight before administration of the test articles, but were allowed free access to water. On the following day, a pre-dose blood sample of about 2 mL was collected from each animal. Subsequently, each group of animals was given a single SC injection or tablet containing leuprolide blended in the specified formulation. The dogs were fed 6 hours after dosing.

After SC administration of the drug (0.01 mg/kg), 2 mL blood samples were collected from the brachial vein at 0.17, 0.33, 0.5, 0.75, 1, 1.5, 2, 3, 4, 6, 8, 12 and 24 hours post-dose. After oral administration, 2 mL blood samples were collected from the brachial vein at 0.5, 1, 1.33, 1.67, 2, 2.33, 2.67, 3, 3.33, 3.67, 4, 6, 8, 12 and 24 hours post administration.

Pharmacokinetic Software

The pharmacokinetic (PK) profile of leuprolide was determined using plasma assay data. Plasma concentration-time data for individual subjects were analyzed by non-compartmental methods using the actual blood draw times, estimating the area under the curve (AUC) with the trapezoidal rule. Microsoft® Excel 2010 was used for all calculations. Section 0 provides a list of the PK parameters that were determined from the plasma concentration-time data.

Pharmacokinetic Data

The following PK metrics were estimated on the basis of non-compartmental analysis of plasma concentration-time course data using nominal blood sampling times:

$T_{lag}$ —the time of the first measurable plasma concentration value;

$T_{max}$ —the time to reach maximum plasma concentration;

T½—the time necessary for the concentration of drug in the plasma to decrease by one-half $C_{max}$ —the maximum observed plasma concentration (in picograms per milliliter).

$AUC_{(0-24\ hr)}$ —the area under the plasma concentration versus time curve from time zero to the time of the last measurable plasma concentration.

$$AUC(pg/mL*hr) = \sum_{0}^{t}\left(\frac{(Cp_2 + Cp_1)}{2} \times (t_2 - t_1)\right).$$

The calculated AUCs were then corrected for the actual dose given based on assay data and the subject body weight (mg/kg). The values were corrected for actual dose based on assay and body weight of the individual dog;

% F—absolute bioavailability (Fraction absorbed relative to intravenous administration) was calculated from the mean subcutaneous response, using normalized AUC. The bioavailability of leuprolide by subcutaneous injection is comparable to that by intravenous administration. Bioavailability was calculated using the mg/kg-corrected AUCs [(hr*pg/mL)/(mg/kg)]:

$$\% F = \frac{AUC^{PO}}{AUC^{IV}} \times 100\%.$$

All PK parameters were summarized using descriptive statistics (average and percent coefficient of variation [% CV]) for each treatment. Data from all individual dogs were included in the analyses.

A summary of the PK results is provided in Table 6A and 6B.

TABLE 6A

Summary of Pharmacokinetic Results

| Dosage Form | Tlag (hrs.) | | Tmax (hrs.) | | T½ (hrs.) | |
|---|---|---|---|---|---|---|
| | Avg. | CV | Avg. | CV | Avg. | CV |
| A: 500 mg CA, 50 mg LLC, 3 mg Leuprolide (n = 6) | 2.5 | 93% | 3 | 60% | 1.56 | 15% |
| B: 500 mg CA, 50 mg LLC, 1 mg Leuprolide (n = 6) | 0.81 | 35% | 1.81 | 29% | 2.13 | 38% |
| C: 250 mg CA, 50 mg LLC, 3 mg Leuprolide (n = 6) | 1.72 | 35% | 2.33 | 36% | 1.41 | 22% |
| D: Unformulated 3 mg Leuprolide (n = 6) | 1.18 | 16% | 1.5 | 16% | 1.39 | 35% |
| E: 250 mg CA, 50 mg LLC, 3 mg Leuprolide SLOW (n = 6) | 1.89 | 41% | 2.51 | 35% | 1.58 | 19% |
| G: 250 mg CA, 50 mg LLC, 3 mg Leuprolide FAST (n = 6) | 1.64 | 76% | 2.22 | 84% | 1.9 | 32% |
| SC: 0.1 mg Leuprolide (n = 3) | 0.17 | 17% | 0.94 | 59% | 1.72 | 16% |

TABLE 6B

Summary of Pharmacokinetic Results

| Dosage Form | Cmax (pg/mL)/(mg/kg) | | AUC(pg/mL* hr.)/(mg/kg) | | % F | | |
|---|---|---|---|---|---|---|---|
| | Avg. | CV | Avg. | CV | Avg. | Median | CV |
| A: 500 mg CA, 50 mg LLC, 3 mg Leuprolide (n = 6) | 58907 | 55% | 164499 | 56% | 6.10% | 6.80% | 56% |
| B: 500 mg CA, 50 mg LLC, 1 mg Leuprolide (n = 6) | 45661 | 61% | 140215 | 53% | 5.20% | 5.80% | 53% |
| C: 250 mg CA, 50 mg LLC, 3 mg Leuprolide (n = 6) | 101786 | 68% | 200111 | 68% | 7.40% | 5.00% | 68% |
| D: Unformulated 3 mg Leuprolide (n = 6) | 7677 | 93% | 15625 | 87% | 0.60% | | 87% |

TABLE 6B-continued

Summary of Pharmacokinetic Results

| Dosage Form | Cmax (pg/mL)/(mg/kg) | | AUC(pg/mL* hr.)/(mg/kg) | | % F | | |
|---|---|---|---|---|---|---|---|
| | Avg. | CV | Avg. | CV | Avg. | Median | CV |
| E: 250 mg CA, 50 mg LLC, 3 mg Leuprolide SLOW (n = 6) | 130942 | 63% | 262777 | 56% | 9.80% | 10.60% | 56% |
| G: 250 mg CA, 50 mg LLC, 3 mg Leuprolide FAST (n = 6) | 87552 | 57% | 238811 | 83% | 8.90% | 6.60% | 83% |
| SC: 0.1 mg Leuprolide (n = 3) | 1081540 | 33% | 2686192 | 21% | 100% | | 21% |

Subcutaneous (SC) Administration of Leuprolide

Figure 7:
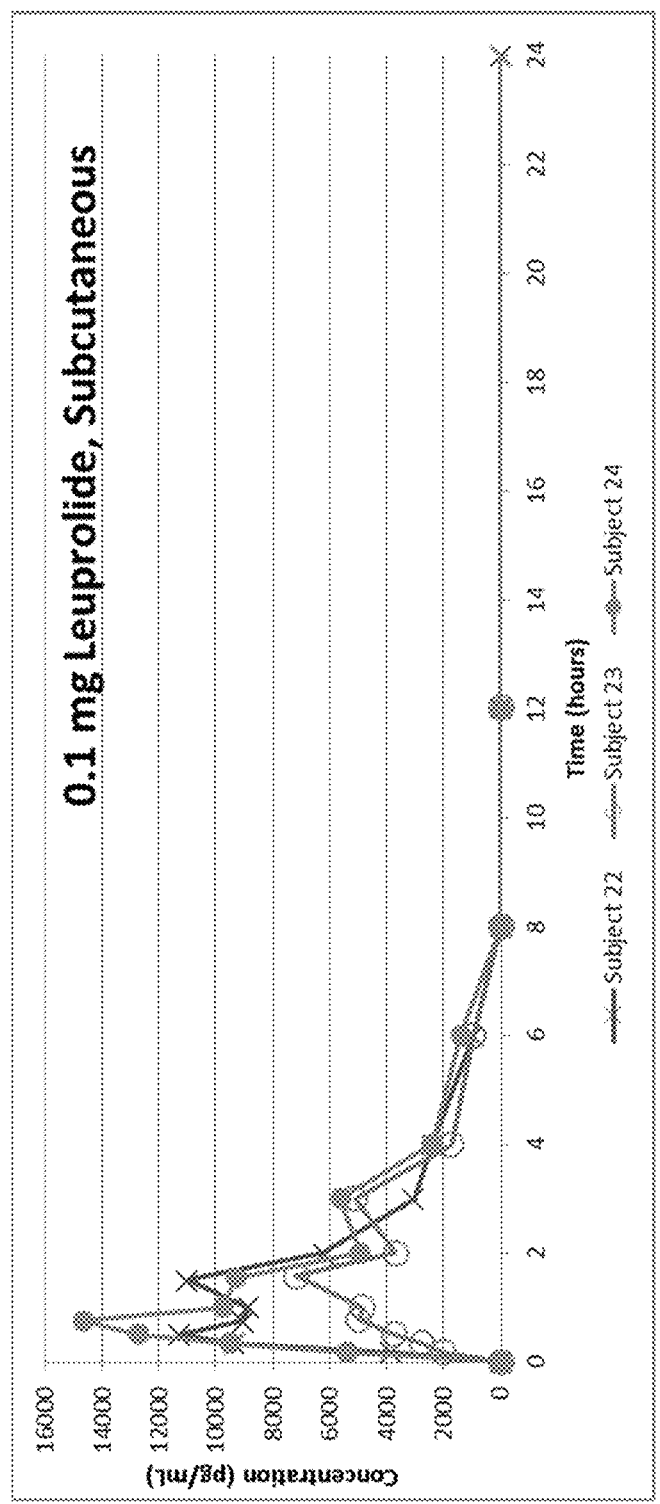
FIG. 7 shows a linear time-concentration curve after subcutaneous administration to beagle dogs of 0.1 mg/kg of leuprolide.
Figure 8:
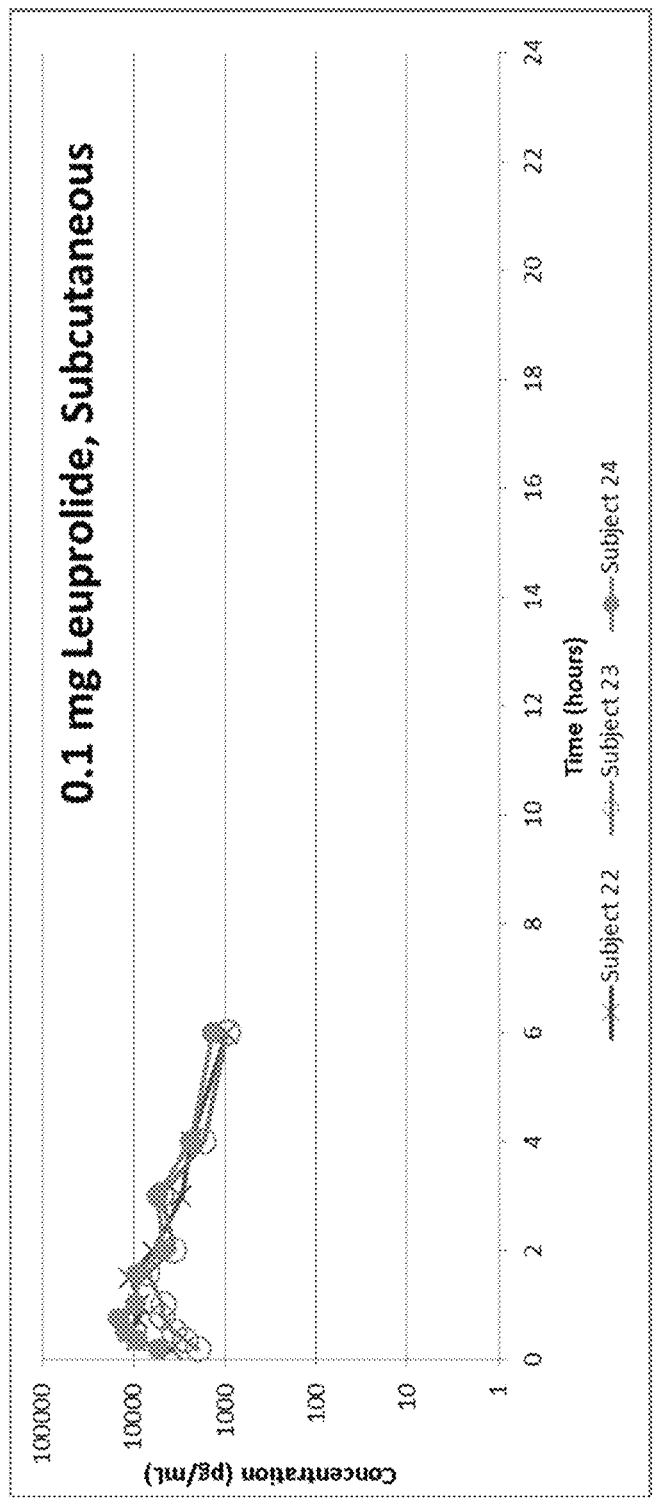
FIG. 8 shows a semi-log time-concentration curve after subcutaneous administration to beagle dogs of 0.1 mg/kg of leuprolide.

The entire time-concentration plot is provided in FIG. 7 on a linear scale and is duplicated in FIG. 8 using a semi-log scale.

3 mg Leuprolide Tablets with 500 mg Citric Acid and 50 mg LLC (Prototype A)

Figure 9:
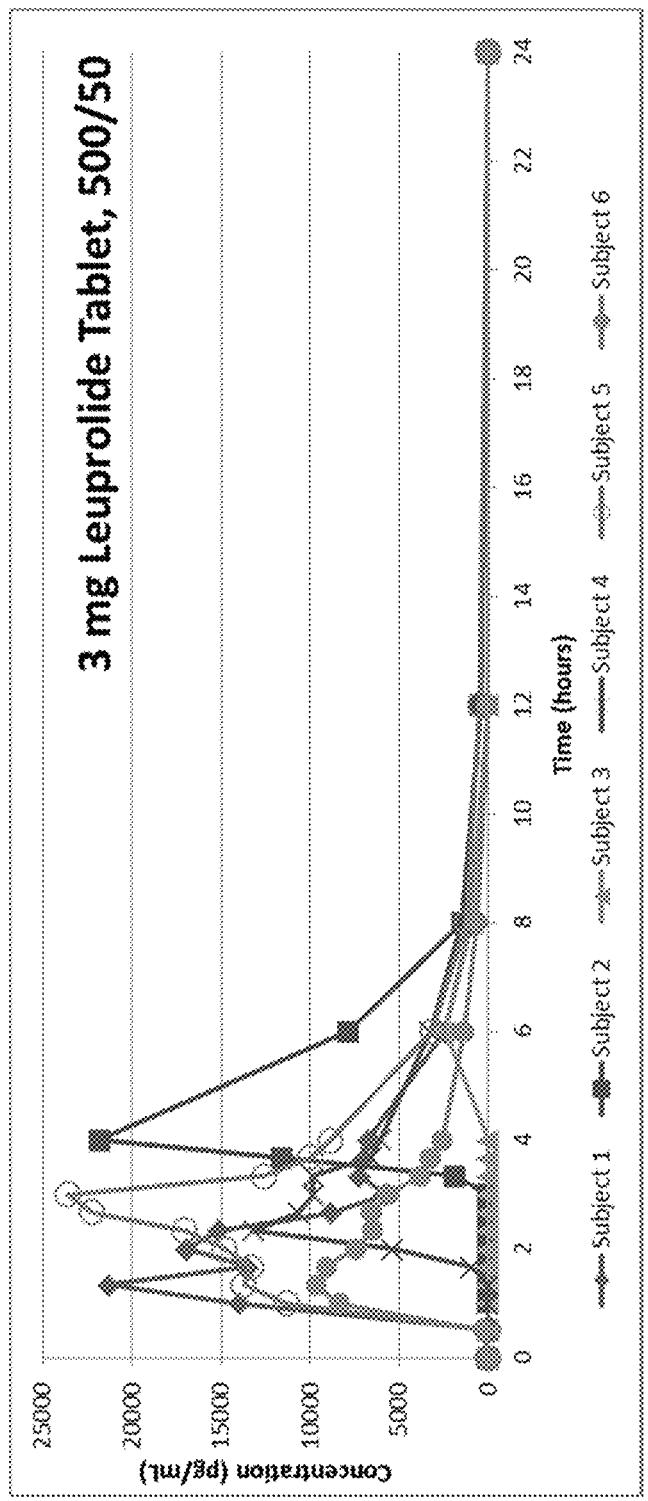
FIG. 9 shows a linear time-concentration curve after oral administration to beagle dogs "Prototype A" tablets of the present disclosure containing 3.0 mg of leuprolide. The Prototype A tablets included 500 mg citric acid and 50 mg LLC, and were enteric coated.
Figure 10:
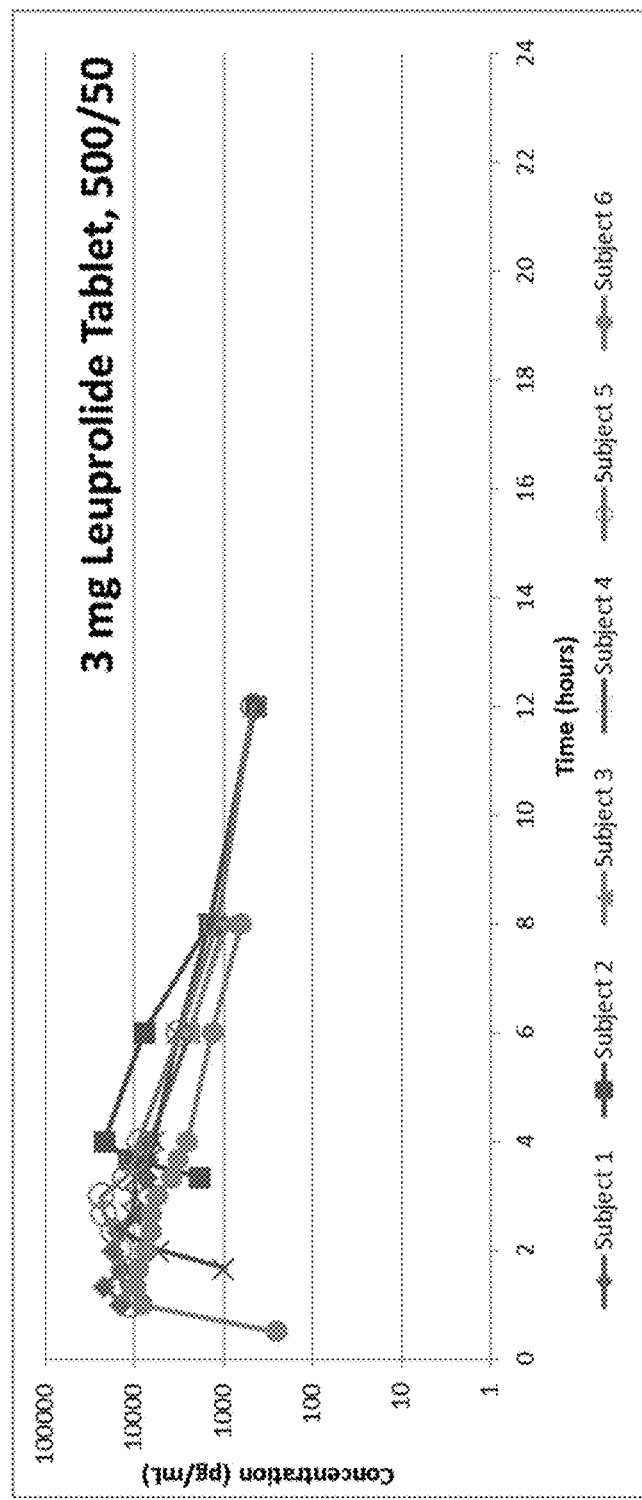
FIG. 10 shows a semi-log time-concentration curve after oral administration to beagle dogs "Prototype A" tablets of the present disclosure containing 3.0 mg of leuprolide. The Prototype A tablets included 500 mg citric acid and 50 mg LLC, and were enteric coated.

Six dogs were dosed with single units of the enhanced formulation prototype A (3 mg strength, enteric coated, 500 mg of citric acid and 50 mg of LLC). The entire time-concentration plot is provided (FIG. 9) on a linear scale and is duplicated in using a semi-log scale (FIG. 10). The data indicate a 10-fold increase in bioavailability relative to the non-enhanced formulation (prototype D).

1 mg Leuprolide Tablets with 500 mg Citric Acid and 50 mg LLC (Prototype B)

Figure 11:
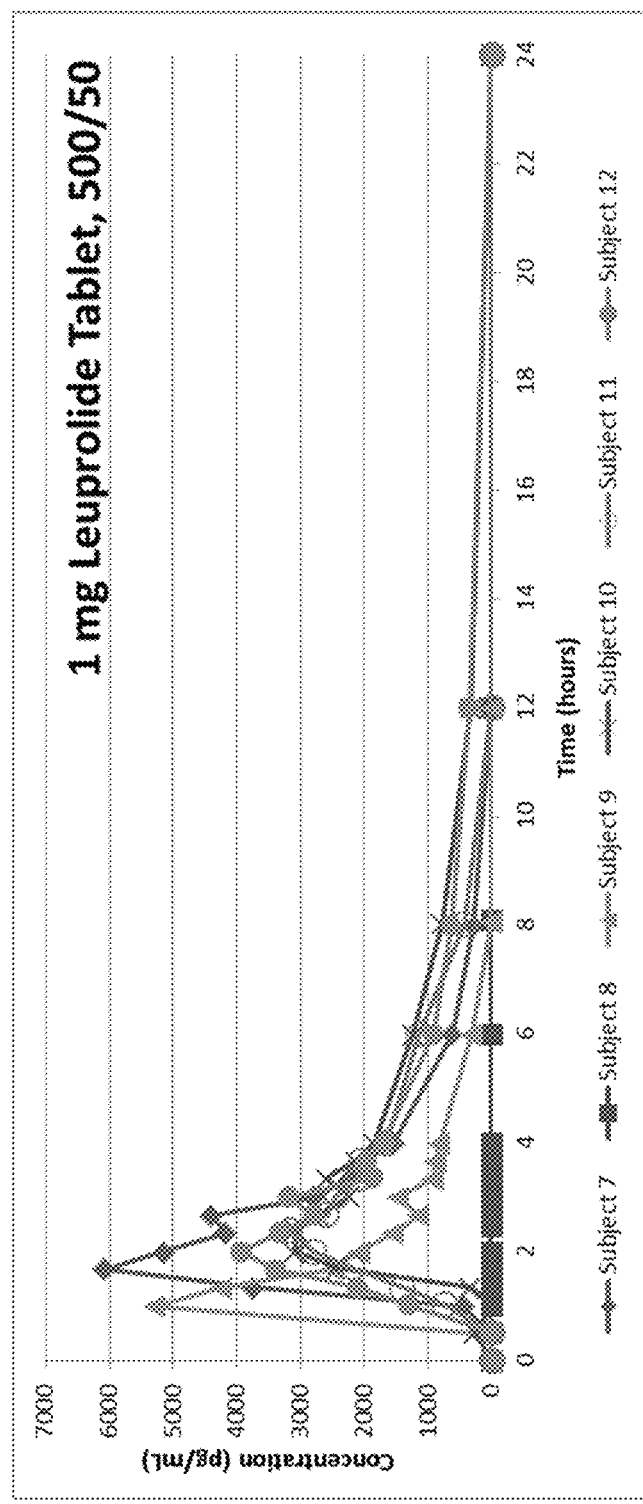
FIG. 11 shows a linear time-concentration curve after oral administration to beagle dogs "Prototype B" tablets of the present disclosure containing 1.0 mg of leuprolide. The Prototype B tablets included 500 mg citric acid and 50 mg LLC, and were enteric coated.
Figure 12:
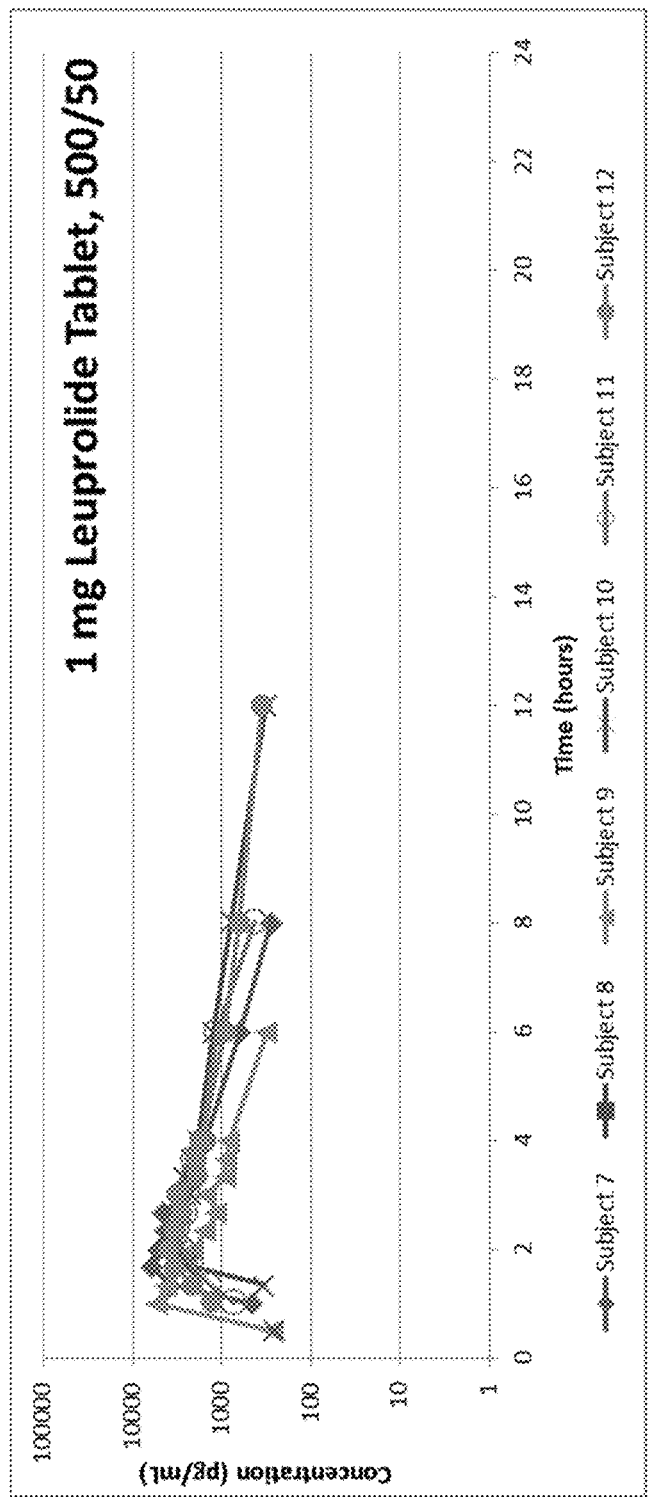
FIG. 12 shows a semi-log time-concentration curve after oral administration to beagle dogs "Prototype B" tablets of the present disclosure containing 1.0 mg of leuprolide. The Prototype B tablets included 500 mg citric acid and 50 mg LLC, and were enteric coated.

Six dogs were dosed with single units of the enhanced formulation prototype B (1 mg strength, enteric coated, 500 mg of citric acid and 50 mg of LLC). The entire time-concentration plot is provided in (FIG. 11) on a linear scale and is duplicated using a semi-log scale in (FIG. 12). Prototype B was identical in formulation to prototype A with the exception of strength. The data indicated that the PK response was linear with respect to dose in the 1 mg to 3 mg range.

3 mg Leuprolide Tablets with 250 mg Citric Acid and 50 mg LLC (Prototype C)

Figure 13:
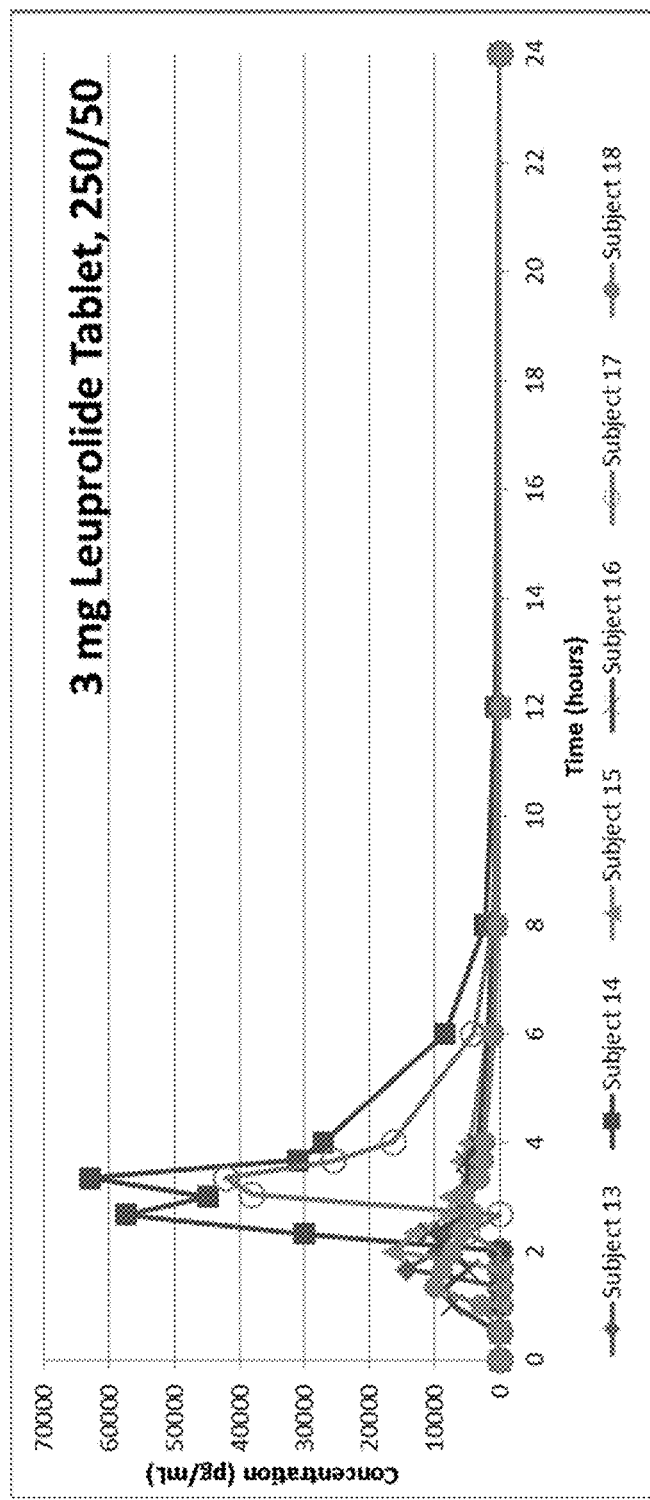
FIG. 13 shows a linear time-concentration curve after oral administration to beagle dogs "Prototype C" tablets of the present disclosure containing 3.0 mg of leuprolide. The Prototype C tablets included 250 mg citric acid and 50 mg LLC, and were enteric coated.
Figure 14:
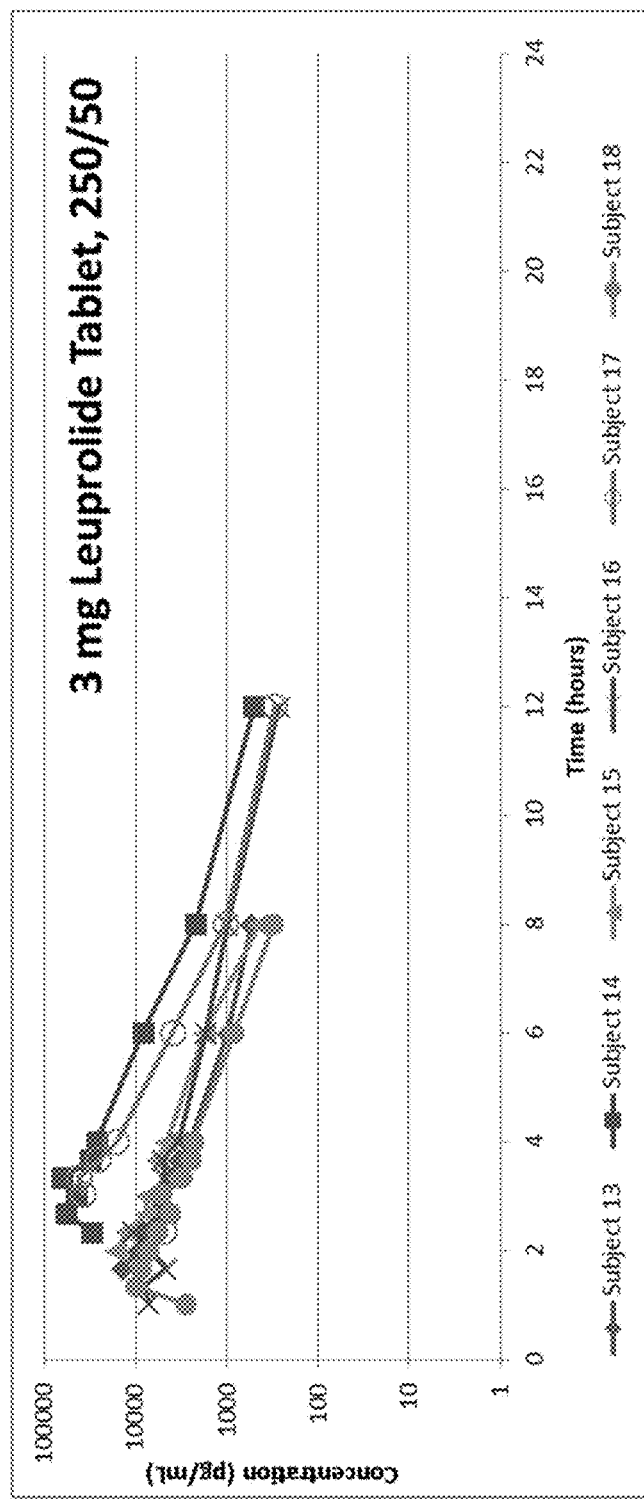
FIG. 14 shows a semi-log time-concentration curve after oral administration to beagle dogs "Prototype C" tablets of the present disclosure containing 3.0 mg of leuprolide. The Prototype C tablets included 250 mg citric acid and 50 mg LLC, and were enteric coated.

Six dogs were dosed with individual units of the enhanced 3 mg leuprolide Prototype C tablets (3 mg strength, enteric coated, 250 mg of citric acid and 50 mg of LLC). The entire time-concentration plot is provided in (FIG. 13) on a linear scale and is duplicated in (FIG. 14) using a semi-log scale. Prototype C tablets differ from prototype A in that there is half the amount of citric acid (only 250 mg) and that the tablet size is substantially smaller. The mean bioavailability for prototype C was 5.6% with a 46% CV which is consistent with the results for prototype A.

3 mg Non-Enhanced Leuprolide Tablet (Prototype D)

Figure 15:
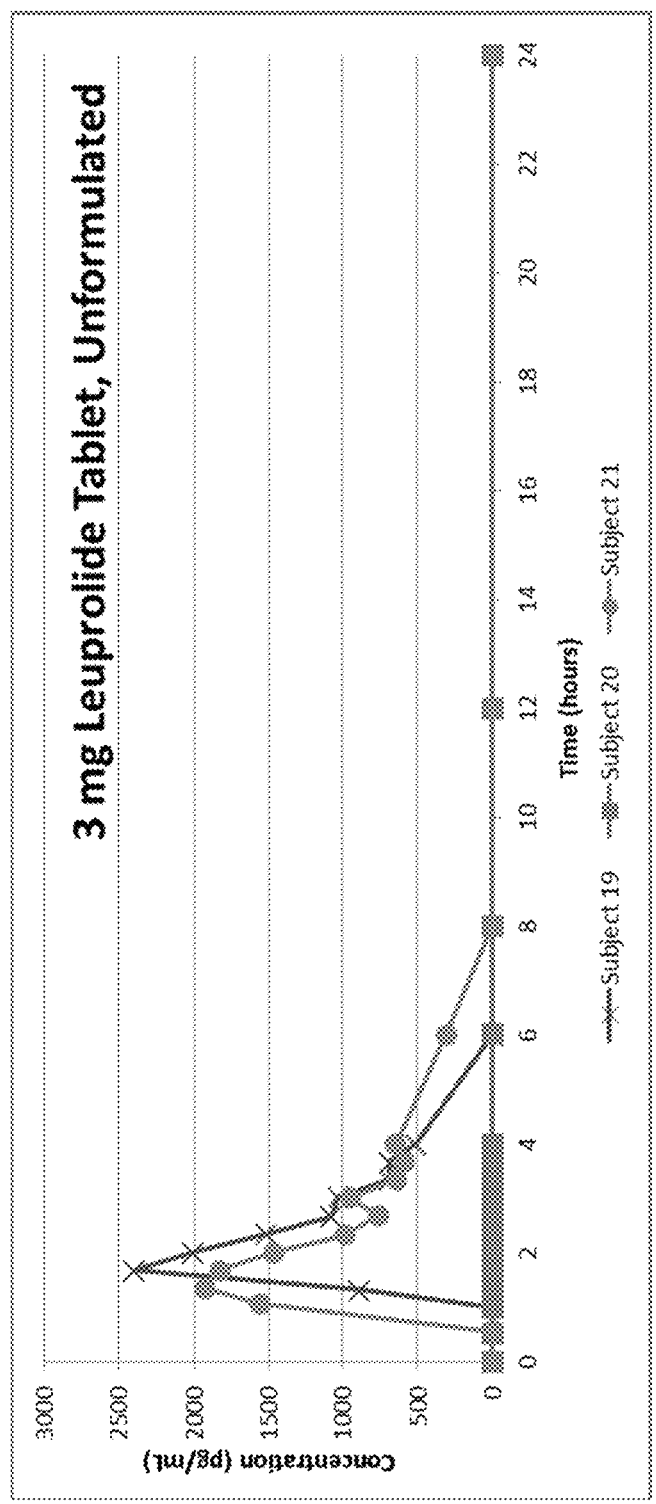
FIG. 15 shows a linear time-concentration curve after oral administration to beagle dogs of unformulated containing 3.0 mg of leuprolide.
Figure 16:
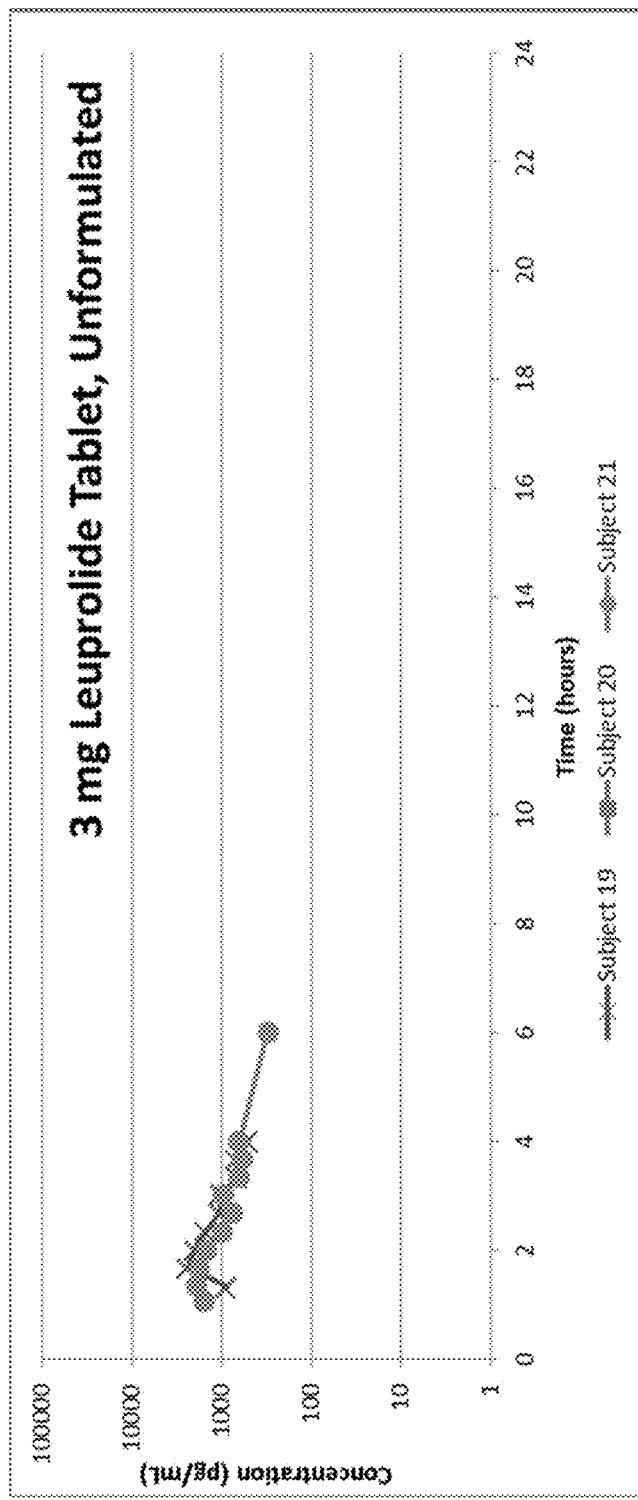
FIG. 16 shows a semi-log time-concentration curve after oral administration to beagle dogs of unformulated containing 3.0 mg of leuprolide.

Three dogs were dosed with the non-enhanced 3 mg leuprolide tablets (enteric coated, but without citric acid or LLC). The entire time-concentration plot is provided in (FIG. 15) on a linear scale and is duplicated in (FIG. 16) using a semi-log scale.

Slower Dissolving Tablet with 250 mg Citric Acid and 50 mg LLC (Prototype E)

Figure 17:
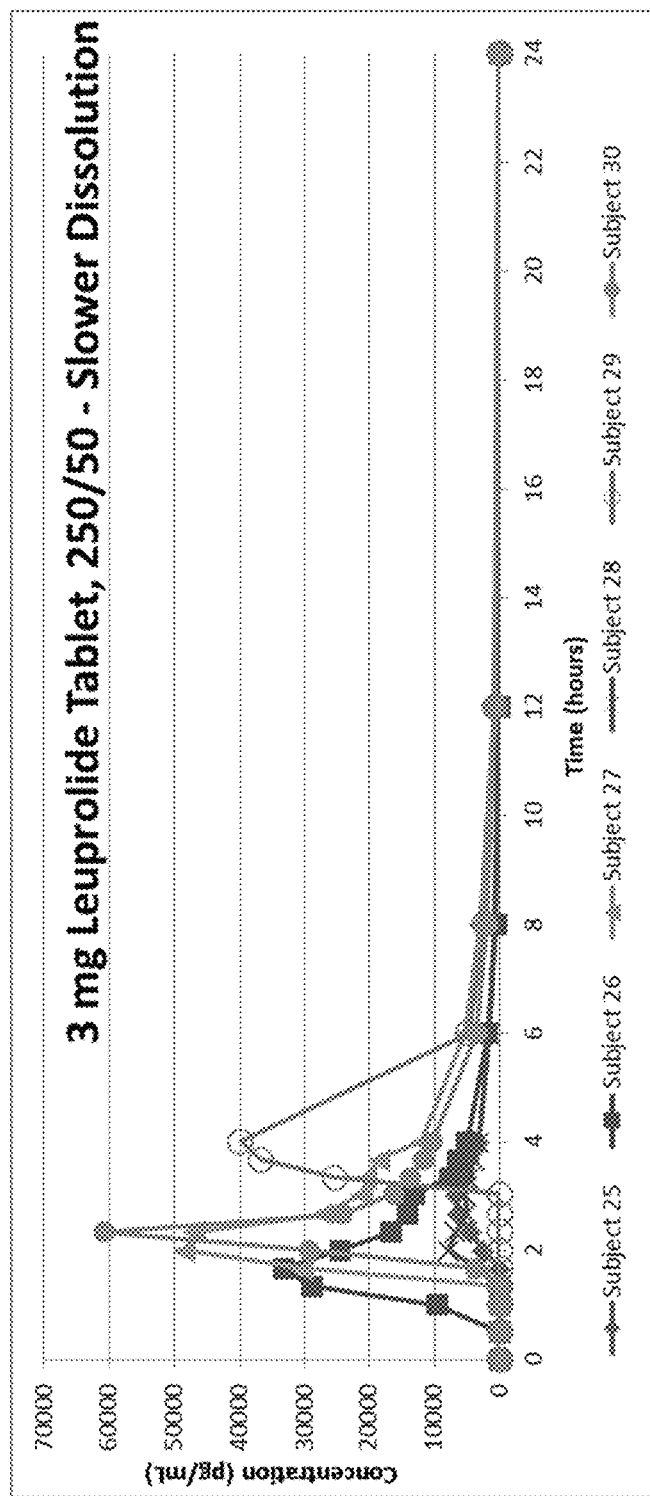
FIG. 17 shows a linear time-concentration curve after oral administration to beagle dogs "Prototype E" tablets of the present disclosure containing 3.0 mg of leuprolide. The Prototype E tablets included 250 mg citric acid and 50 mg LLC, and were enteric coated.
Figure 18:
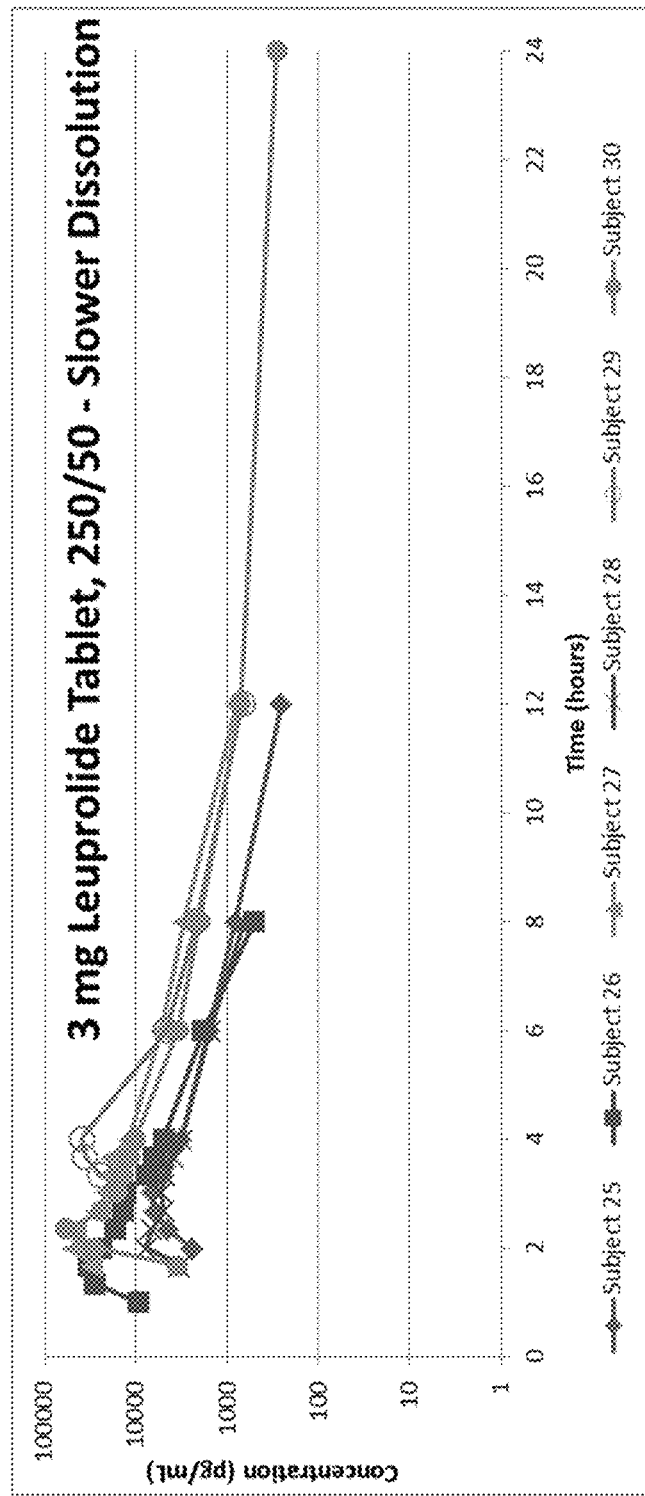
FIG. 18 shows a semi-log time-concentration curve after oral administration to beagle dogs "Prototype E" tablets of the present disclosure containing 3.0 mg of leuprolide. The Prototype E tablets included 250 mg citric acid and 50 mg LLC, and were enteric coated.

Six dogs were dosed with single units of the enhanced formulation prototype E (3 mg strength, 250 mg of CA and 50 mg of LLC, 19 mg/cm$^2$ IR, 15 mg/cm$^2$ EC). The entire time-concentration plot is provided in (FIG. 17) on a linear scale and is duplicated in (FIG. 18) using a semi-log scale.

Faster Dissolving Tablet with 250 mg Citric Acid and 50 mg LLC (Prototype G)

Figure 19:
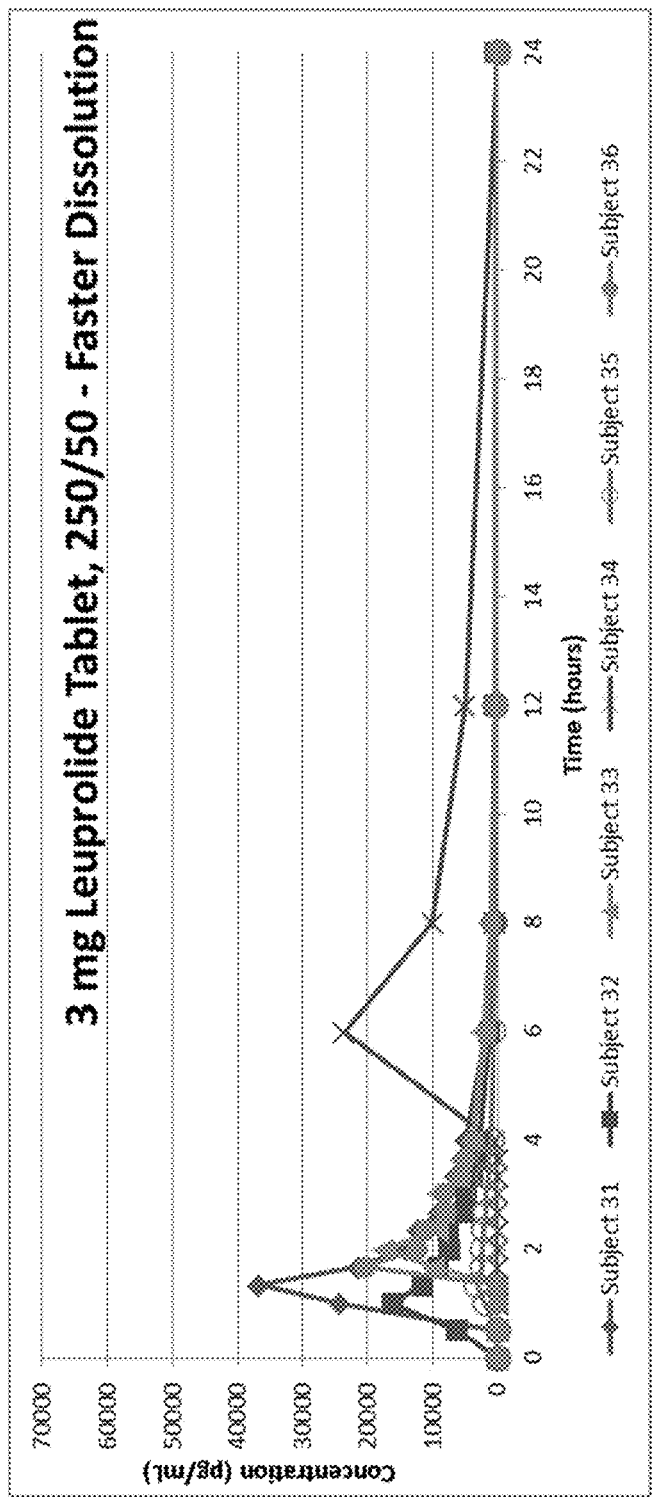
FIG. 19 shows a linear time-concentration curve after oral administration to beagle dogs "Prototype G" tablets of the present disclosure containing 3.0 mg of leuprolide. The Prototype G tablets included 250 mg citric acid and 50 mg LLC, and were enteric coated.
Figure 20:
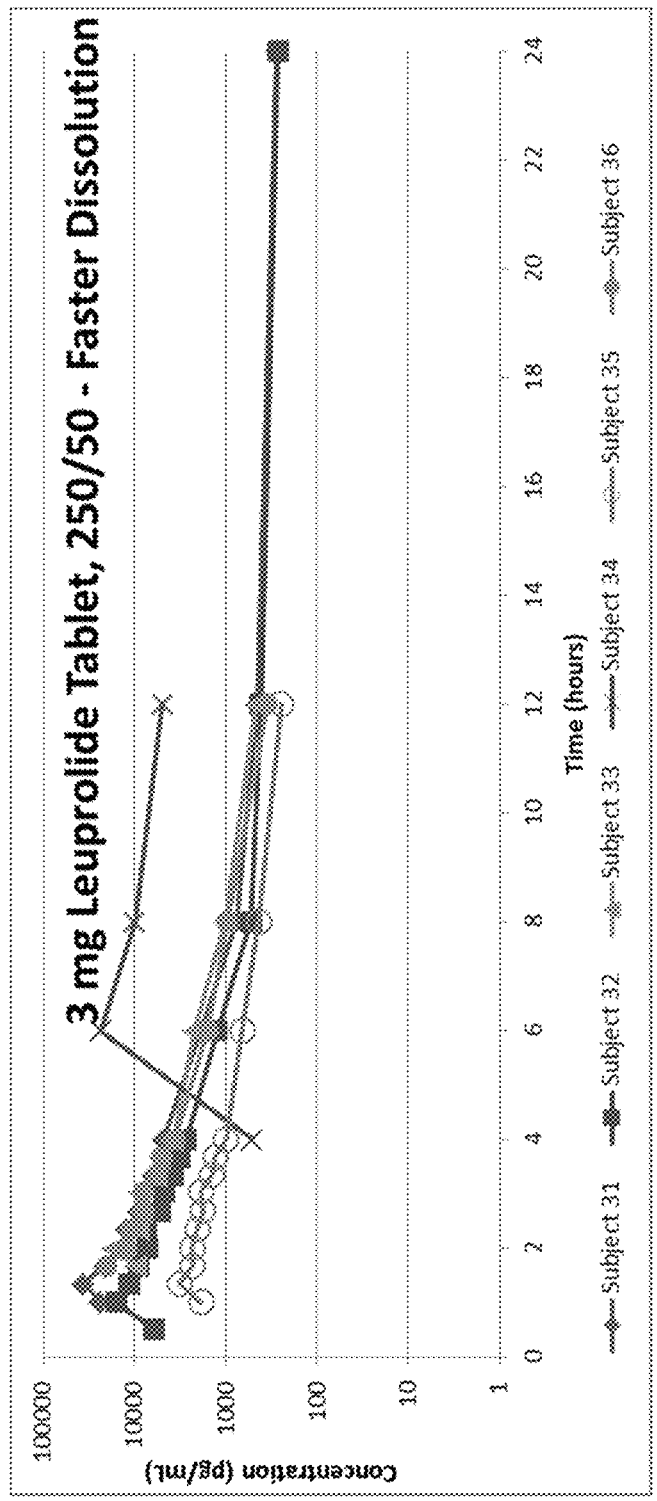
FIG. 20 shows a semi-log time-concentration curve after oral administration to beagle dogs "Prototype G" tablets of the present disclosure containing 3.0 mg of leuprolide. The Prototype G tablets included 250 mg citric acid and 50 mg LLC, and were enteric coated.

Six dogs were dosed with single units of the enhanced formulation prototype E (3 mg strength, 250 mg of CA and 50 mg of LLC, 11 mg/cm$^2$ IR, 5 mg/cm$^2$ EC). The entire time-concentration plot is provided in (FIG. 19) on a linear scale and is duplicated in (FIG. 20).

A 250 mg citric acid formulation (Prototypes C, E and G) may be favored over a 500 mg citric acid formulation (Prototypes A and B) for a number of reasons. However, as illustrated in the results from Prototype C, that formulation did show moderately higher variability than its 500 mg citric acid counterparts (Prototypes A and B). The smaller sized tablet (Prototype C) showed median absorption levels similar to or slightly less than the larger tablets (Prototypes A and B) containing more citric acid, but often with one or two very high values which in-turn skew the averages higher than other tablets tested. The present study was undertaken to elucidate the effect, if any, of deliberate variations of the dissolution profile on absorption of tablets which are otherwise similar to prototype C.

Figure 21:
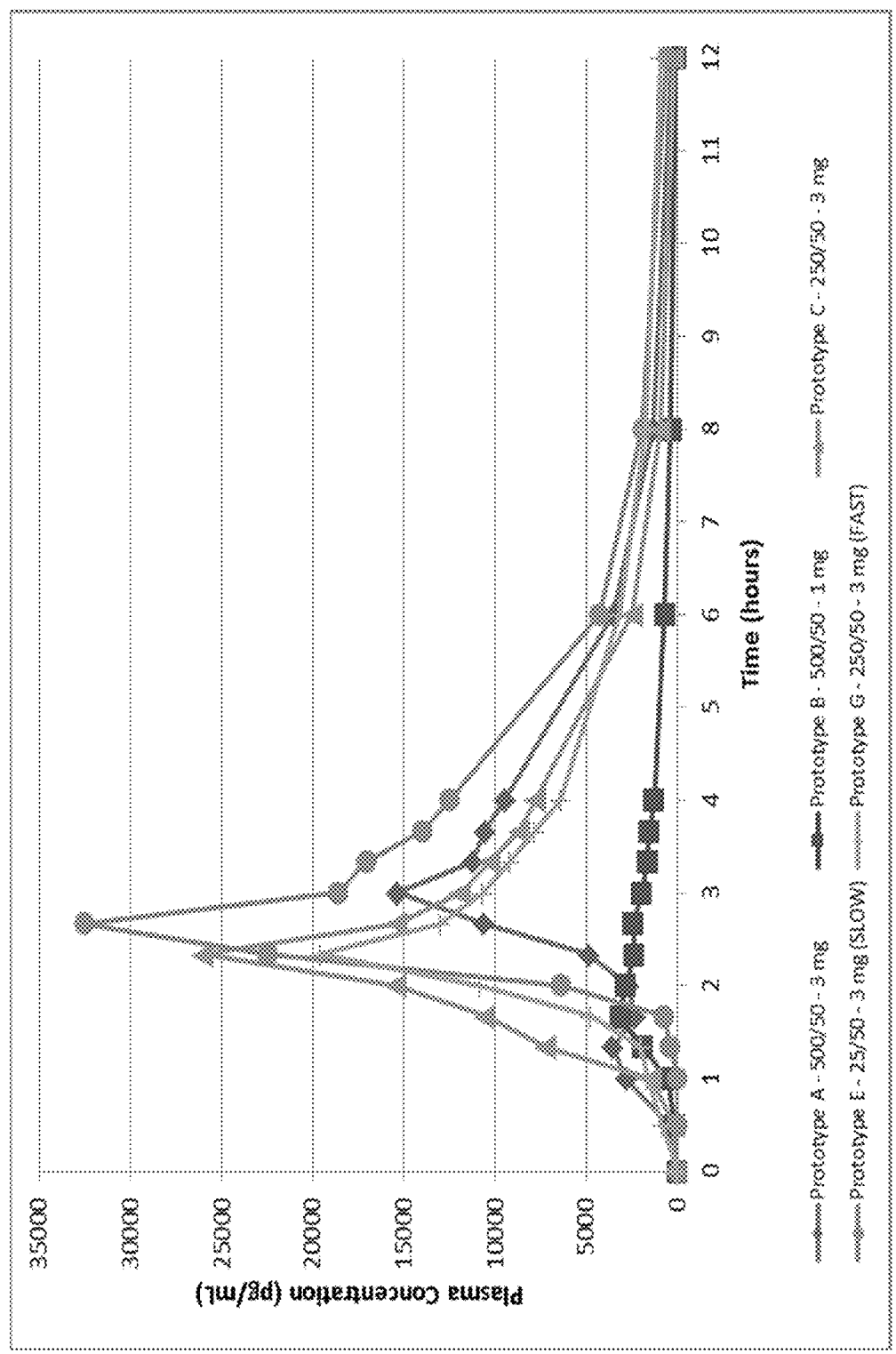
FIG. 21 shows a linear time-concentration curve after oral administration of various leuprolide tablets of the present disclosure to beagle dogs.

FIG. 21 shows a linear time-concentration curve after oral administration of various leuprolide tablets of the present disclosure to beagle dogs. The tablets that showed the shortest lag time ($T_{lag}$) before opening in the neutral medium, in-vitro, (prototype G, see Table 6A) also showed the earliest average times of first measurable response and maximum concentration in the dogs. Likewise, the tablets which showed the longest lag time ($T_{lag}$) in-vitro (prototype E, see Table 6A), showed the longest average times of first measurable response and maximum concentration in the dogs.

Figure 22:
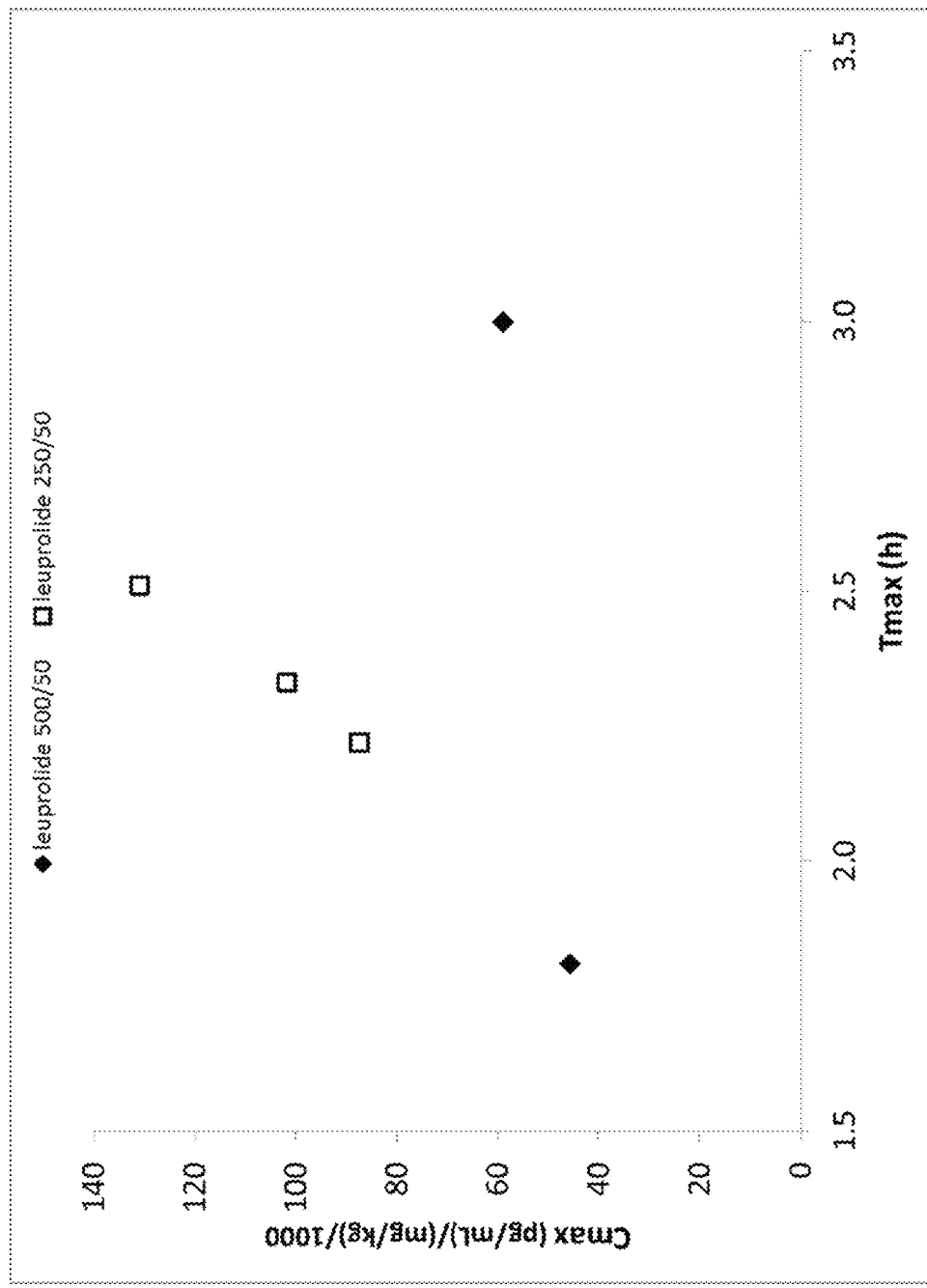
FIG. 22 shows the values of $C_{max}$ vs. $T_{max}$ for the leuprolide tablet prototypes.
Figure 23:
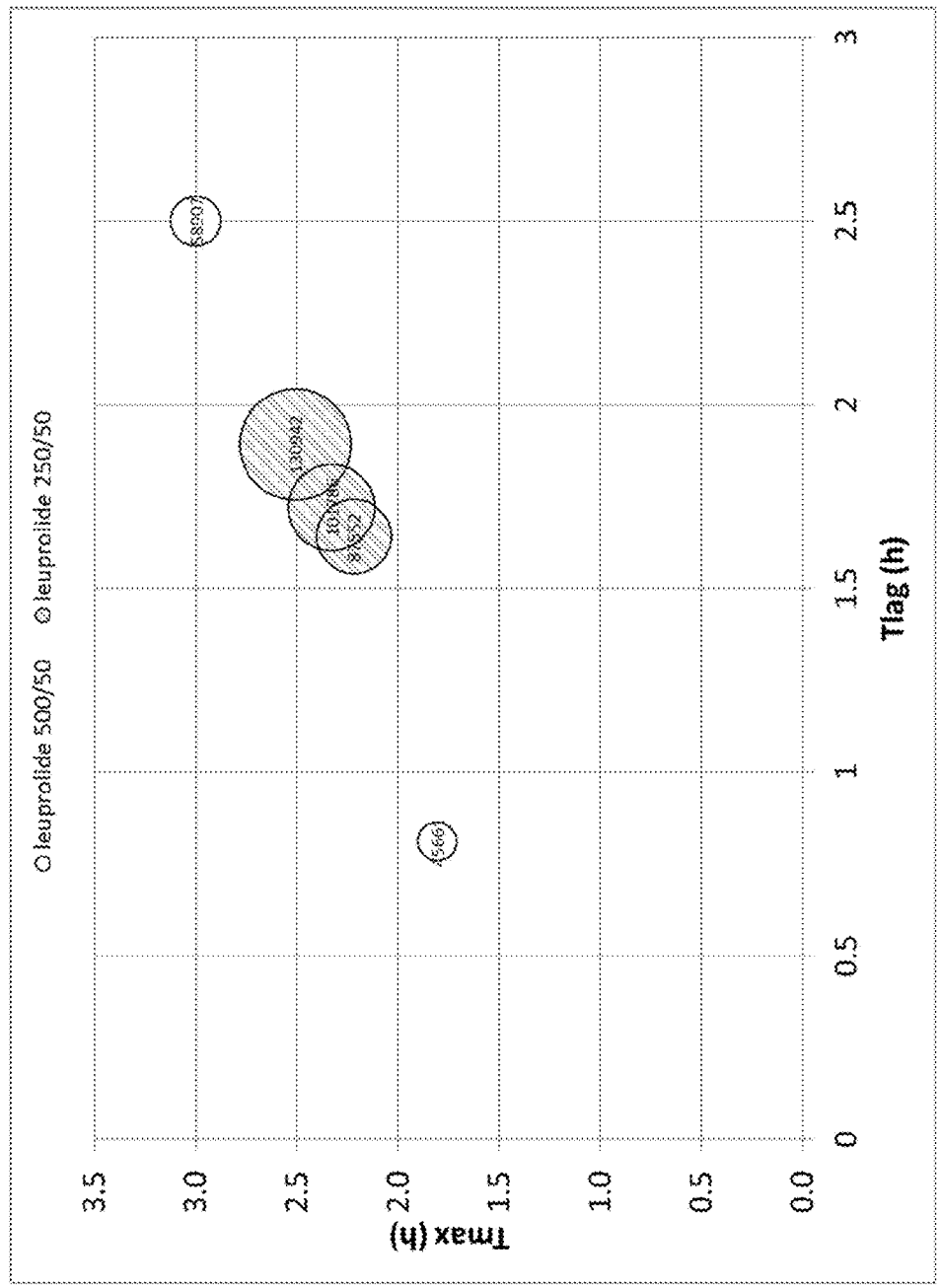
FIG. 23 shows a bubble plot representation of the leuprolide data, showing $T_{max}$ versus $T_{lag}$. The size of the bubble corresponds to the absolute bioavailability (also labeled on the data points).

The effects of $T_{lag}$ and $T_{max}$ on absorption are illustrated in FIG. 22 and FIG. 23. In FIG. 22, the response of $C_{max}$ vs. $T_{max}$ is shown. For both the formulations containing 500 mg CA/50 mg LLC (prototypes A and B, "leuprolide 500/50") and those containing 250 mg CA/50 mg LLC (prototypes C, E and G, "leuprolide 250/50"), there is an increase in $C_{max}$ as $T_{max}$ increases. FIG. 23 shows the dependence of $C_{max}$ on both $T_{lag}$ and $T_{max}$. In this bubble plot, the size of the bubble corresponds to the magnitude of $C_{max}$ (also labeled on the data points). The data demonstrate that, for each formulation, an increase in $T_{lag}$, $T_{max}$, or both $T_{lag}$ and $T_{max}$ results in increased absorption.

One of the formulation principles prior to this study was dosage forms (e.g. tablets) which dissolved as rapidly as possible after passage through the stomach to achieve a highly localized bolus concentration of API and absorption enhancers. That principle was derived, in part, from the literature, where it is expected that dissolution of the drug in the duodenum would result in the highest absorption and that variability would be reduced as a consequence of those higher overall bioavailabilities. The data in the present study, however, showed an unexpected and surprising trend in that the tablet which was slowest to open and dissolve (prototype E) showed the greatest average leuprolide absorption with the most precise individual absorptions. While the rapidly dissolving formulation (Prototype G) did show the highest individual absorption of the leuprolide (23.0% F), the average and median % F values were lower and less precise, when compared to Prototype E. The results suggest that the added coating material, and thus longer lag before dissolution, might moderate the extreme high and low absorption values commonly observed with the more lightly coated and therefore more rapidly dissolving tablets.

The results indicated that the dissolution profiles of the tablets can be manipulated to show measureable differences in the pharmacokinetic responses in dogs. Specifically, the data demonstrated that the greatest enteric coat film layer thickness (15 mg/cm$^2$, or approximately 10% weight gain) resulted in higher average bioavailability with improved precision when compared to prototypes with relatively less coating. Bioavailabilities between 9-11% with CVs in the 50-60% s can be achieved.

It is believed that mixtures of Eudragit® L 30 D-55 (an enteric coat which dissolves at pH 5.5 and above) available from Evonik Laboratories and Eudragit® FS 30 D (an enteric coat which dissolves at pH 7.4 and above) available from Evonik Laboratories, for example at a ratio of at least 75:25 mixture of Eudragit® FS 30: Eudragit® L 30 D-55 D, can delay an onset of dissolution further down the small intestine compared to at least one example discussed above (e.g., but not limited to, prototype E). The resulting delayed dissolution should be comparable to a tablet coated with more than 15 mg/cm$^2$ layer of Eudragit® L 30 D-55.

A tablet of the present disclosure may include a reduced amount (e.g., between about 0.1% to about 99% reduction or between about 1% to about 99% reduction) of the tablet disintegrant compared with, e.g., but not limited to, the examples described herein. Alternatively, a tablet of the present disclosure may not include a tablet disintegrant.

A tablet of the present disclosure may include a HPC/HPMC filler and/or other viscous or low solubility additive, to result in slowing the disintegration of the tablet core after the coating film layers dissolve.

Alternatively, a tablet of the present disclosure may include both (1) a mixture of Eudragit® L 30 D-55 and Eudragit® FS 30 D and (2) a reduced amount of tablet disintegrant and/or a viscous additive (e.g., but not limited to, a HPMC filler).

Example 2

Modified Core

Materials and Methods:

Tablets containing a peptide, triptorelin, were manufactured as described in Table 7. Triptorelin is a decapeptide (pGlu-His-Trp-Ser-Tyr-D-Trp-Leu-Arg-Pro-Gly-NH2), synthetic analogue of gonadotropin-releasing hormone (GnRH) agonist. The tablets were manufactured with and without disintegrant (Kollidon CL), with or without hydroxypropyl cellulose (HPC), HPMC (hydroxypropyl methyl cellulose) or chitosan.

Several formulations of a tablet containing triptorelin as a model peptide API, a pH-lowering agent, and an absorption enhancer were manufactured. The tablet cores varied in the type and amount of filler/binder (microcrystalline cellulose, hydroxypropyl cellulose, hydroxypropyl methyl cellulose, or chitosan), with or without a super-disintegrant (Kollidon CL), in order to vary the rate of release of the peptide API and enhancing agents. A slower release rate from the dosage form is expected to cause a delay in $T_{max}$. Furthermore, the tablets were coated with an acid-resistant enteric coating, which varied in thickness and buffer capacity. Tablets with thick (10% w/w) enteric coats or enhanced buffer capacity (pH 2.3) are expected to open later in the gastrointestinal tract, and hence have a larger value of $T_{lag}$ relative to tablets coated with 6% (w/w) enteric coat or decreased buffer capacity (pH 5.2-5.3). Also tested were tablets containing no enhancing excipients, and a tablet in which the permeation enhancer LLC was replaced with SDS (a surfactant with a higher critical micelle concentration (CMC) resulting in stronger surfactant properties).

TABLE 7

| | Formulations | | | | | | | |
|---|---|---|---|---|---|---|---|---|
| Component | JSV-003-178 | JSV-003-180 | JSV-003-182 | ULB-231-201 | ULB-231-204 | ULB-231-254 | ULB-231-256 | ELB-020-014 |
| triptorelin † (mg) | 4 | 4 | 4 | 4 | 4 | 4 | 4 | 4 |
| LLC-Cl (mg) | 50 | 50 | 0 | 50 | 50 | 50 | 50 | 0 |
| SDS (mg) | 0 | 0 | 0 | 0 | 0 | 0 | 0 | 50 |
| Citric Acid DCF20 (mg) | 250 | 250 | 0 | 250 | 250 | 250 | 250 | 250 |
| Kollidon CL (% w/w) | 0 | 3.5 | 3.5 | 0 | 0 | 0 | 0 | 3.5 |
| Chitosan (% w/w) | 0 | 0 | 0 | 40 | 0 | 40 | 0 | 0 |
| HPC A4MP (% w/w) | 23 | 0 | 0 | 0 | 17 | 0 | 17 | 0 |
| HPMC E3 (% w/w) | 0 | 0 | 0 | 0 | 6 | 0 | 6 | 0 |
| enteric coat (% w/w) | 6 | 10 | 10 | 6 | 6 | 6 | 6 | 6 |
| enteric coat pH | 2.3 | 2.3 | 2.3 | 5.3* | 5.3* | 5.2 | 5.2 | 5.2 |

† As triptorelin free base

*After the dosing events, it was found that the enteric coat of these batches did not pass acid-stage dissolution, and the enteric coat showed substantial cracking when highlighted with a water-soluble dye Results:
The PK data summary is shown in Tables 8A and 8B.

TABLE 8A

| Formulation | Description† | n | Tlag (h) Avg | Tlag (h) CV in % | Tmax (h) Avg | Tmax (h) CV in % | T½ (h) Avg | T½ (h) CV in % |
|---|---|---|---|---|---|---|---|---|
| IV | 0.1 mg/mL triptorelin in PBS | 3 | 0.00 | NC | 0.00 | NC | 2.76 | 35 |
| SC | 0.1 mg/mL triptorelin in PBS | 3 | 0.17 | 0 | 0.53 | 40 | 2.10 | 26 |
| JSV-003-182 | 4 mg triptorelin/ 0 CA/0 LLC, 10% EC (neat) | 3 | 2.67 | NC | 4.00 | NC | 1.44 | NC |
| JSV-003-180 | 4 mg triptorelin/ 250 CA/50 LLC, 10% EC (neat) | 5 | 1.33 | 20 | 1.58 | 26 | 1.70 | 17 |
| JSV-003-178 | 4 mg triptorelin/ 250 CA/50 LLC/MR, 6% EC (neat) | 5 | 1.73 | 37 | 3.07 | 59 | 1.70 | 38 |
| ULB-231-201* | 4 mg triptorelin/ 250 CA/50 LLC/chitosan, 6% EC (pH 5.3) | 6 | 0.67 | 39 | 2.06 | 51 | 2.23 | 20 |
| ULB-231-204* | 4 mg triptorelin/ 250 CA/50 LLC/MR, 6% EC (pH 5.3) | 4 | 0.75 | 38 | 1.33 | 20 | 2.01 | 30 |
| ULB-231-254 | 4 mg triptorelin/ 250 CA/50 LLC/chitosan, 6% EC (pH 5.2) | 6 | 1.03 | 30 | 1.39 | 35 | 1.29 | 16 |
| ULB-231-256 | 4 mg triptorelin/ 250 CA/50 LLC/MR, 6% EC (5.2) | 4 | 1.17 | 61 | 2.39 | 40 | 1.78 | 28 |
| ELB-020-014 | 4 mg triptorelin/ 250 CA/50 SDS, 6% EC (pH 5.2) | 6 | 0.75 | 37 | 1.08 | 45 | 1.43 | 43 |

†PBS, phosphate-buffered saline; CA, citric acid; LLC, lauroyl-L-carnitine; EC, enteric coat; MR, modified release core (HPC/HPMC)
*After the dosing events, it was found that the enteric coat of these batches did not pass acid-stage dissolution, and the enteric coat showed substantial cracking when highlighted with a water-soluble dye

TABLE 8B

| Formulation | Description† | n | Cmax (ng/mL)/(mg/kg) Avg | Cmax CV in % | AUC (ng/mL*h)/(mg/kg) Avg | AUC CV in % | % F (0-24 h) Avg | % F CV |
|---|---|---|---|---|---|---|---|---|
| IV | 0.1 mg/mL triptorelin in PBS | 3 | 5243 | 16 | 8827 | 29 | 100.00% | 29% |
| SC | 0.1 mg/mL triptorelin in PBS | 3 | 2039 | 12 | 5372 | 9 | 60.9% | 9% |
| JSV-003-182 | 4 mg triptorelin/ 0 CA/0 LLC, 10% EC (neat) | 3 | 1.3 | 173 | 4.0 | 173 | 0.05% | 173% |
| JSV-003-180 | 4 mg triptorelin/ 250 CA/50 LLC, 10% EC (neat) | 5 | 31 | 37 | 48 | 34 | 0.55% | 34% |
| JSV-003-178 | 4 mg triptorelin/ 250 CA/50 LLC/MR, 6% EC (neat) | 5 | 48 | 91 | 114 | 81 | 1.29% | 81% |
| ULB-231-201* | 4 mg triptorelin/ 250 CA/50 LLC/chitosan, 6% EC (pH 5.3) | 6 | 18.7 | 133 | 51.2 | 139 | 0.58% | 139% |
| ULB-231-204* | 4 mg triptorelin/ 250 CA/50 LLC/MR, 6% EC (pH 5.3) | 4 | 7.6 | 117 | 19.2 | 90 | 0.22% | 90% |
| ULB-231-254 | 4 mg triptorelin/ 250 CA/50 LLC/chitosan, 6% EC (pH 5.2) | 6 | 5.1 | 64 | 6.4 | 51 | 0.07% | 51% |
| ULB-231-256 | 4 mg triptorelin/ 250 CA/50 LLC/MR, 6% EC (5.2) | 4 | 23.2 | 92 | 56.6 | 108 | 0.64% | 108% |
| ELB-020-014 | 4 mg triptorelin/ 250 CA/50 SDS, 6% EC (pH 5.2) | 6 | 26.3 | 73 | 46.3 | 84 | 0.52% | 84% |

Figure 24:
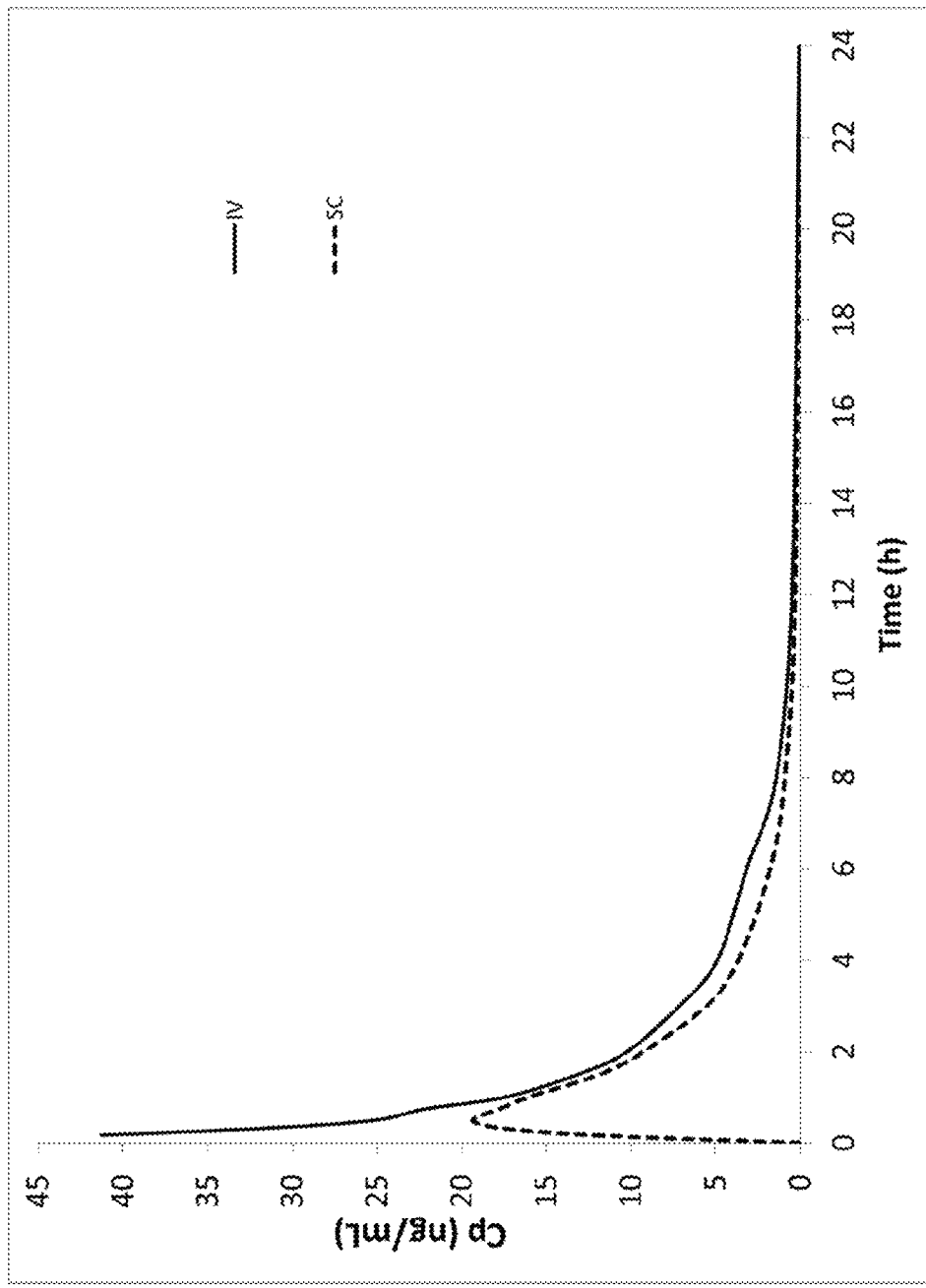
FIG. 24 shows the average PK curves for the intravenous (IV) and subcutaneous (SC) doses.

The average PK curves for the intravenous (IV) and subcutaneous (SC) doses are shown in FIG. 24.

Figure 25A:
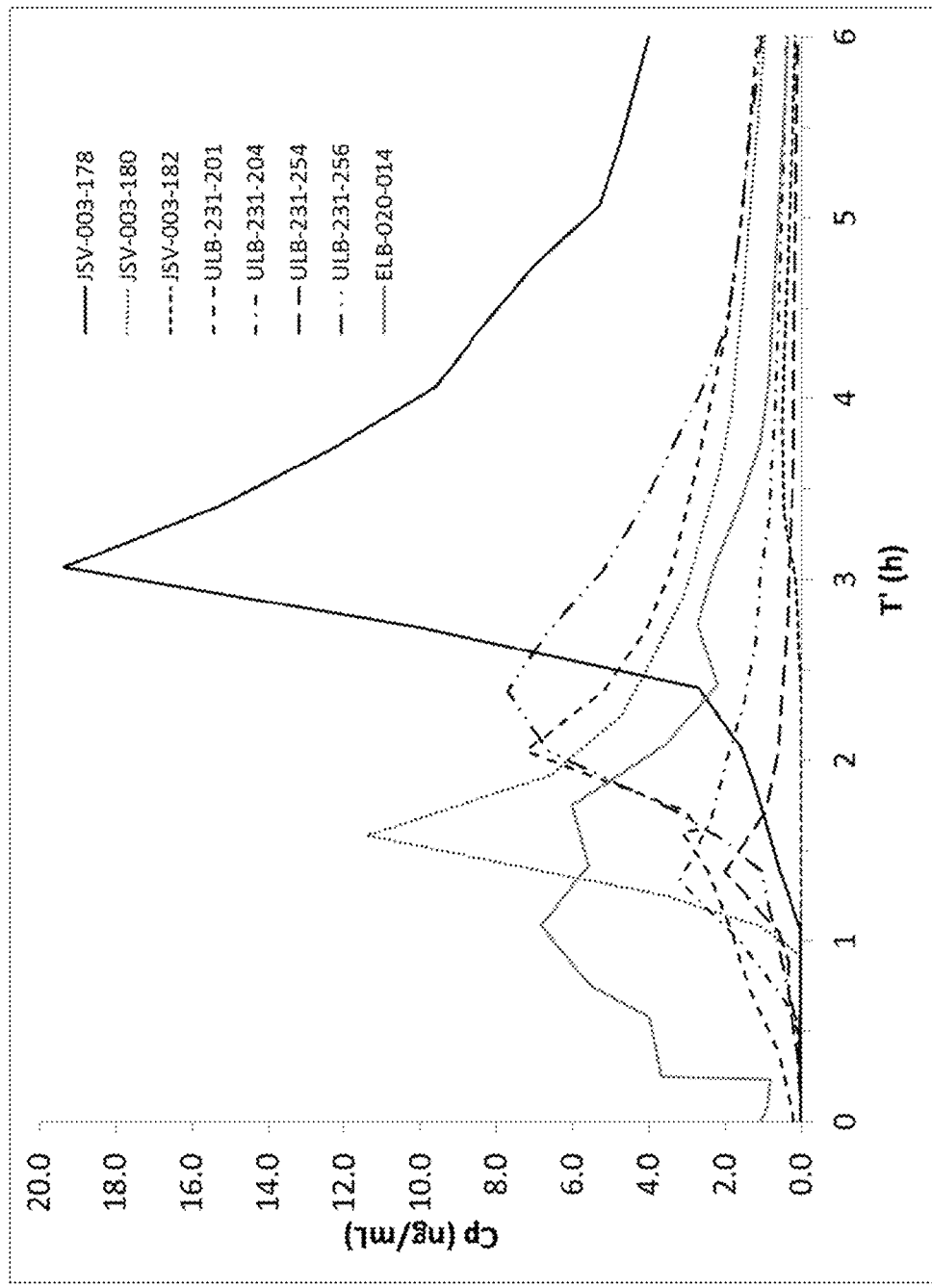
FIGS. 25A and 25B show the average curves for PO doses, corrected for Tmax, for JSV-003-178: 250 CA/50 LLC/MR, 6% EC (pH 2.3), JSV-003-180: 250 CA/50 LLC, 10% EC (pH 2.3), JSV-003-182: 0 CA/0 LLC, 10% EC (pH 2.3), ULB-231-201: 250 CA/50 LLC/chitosan, 6% EC (pH 5.2), ULB-231-204: 250 CA/50 LLC/MR, 6% EC (pH 5.2), ULB-231-254: 250 CA/50 LLC/chitosan, 6% EC (pH 5.3), ULB-231-254: 250 CA/50 LLC/chitosan, 6% EC (pH 5.3), ULB-231-256: 250 CA/50 LLC/MR, 6% EC (pH 5.3) and ELB-020-014: 250 CA/50 SDS, 6% EC (pH 5.3).
Figure 25B:
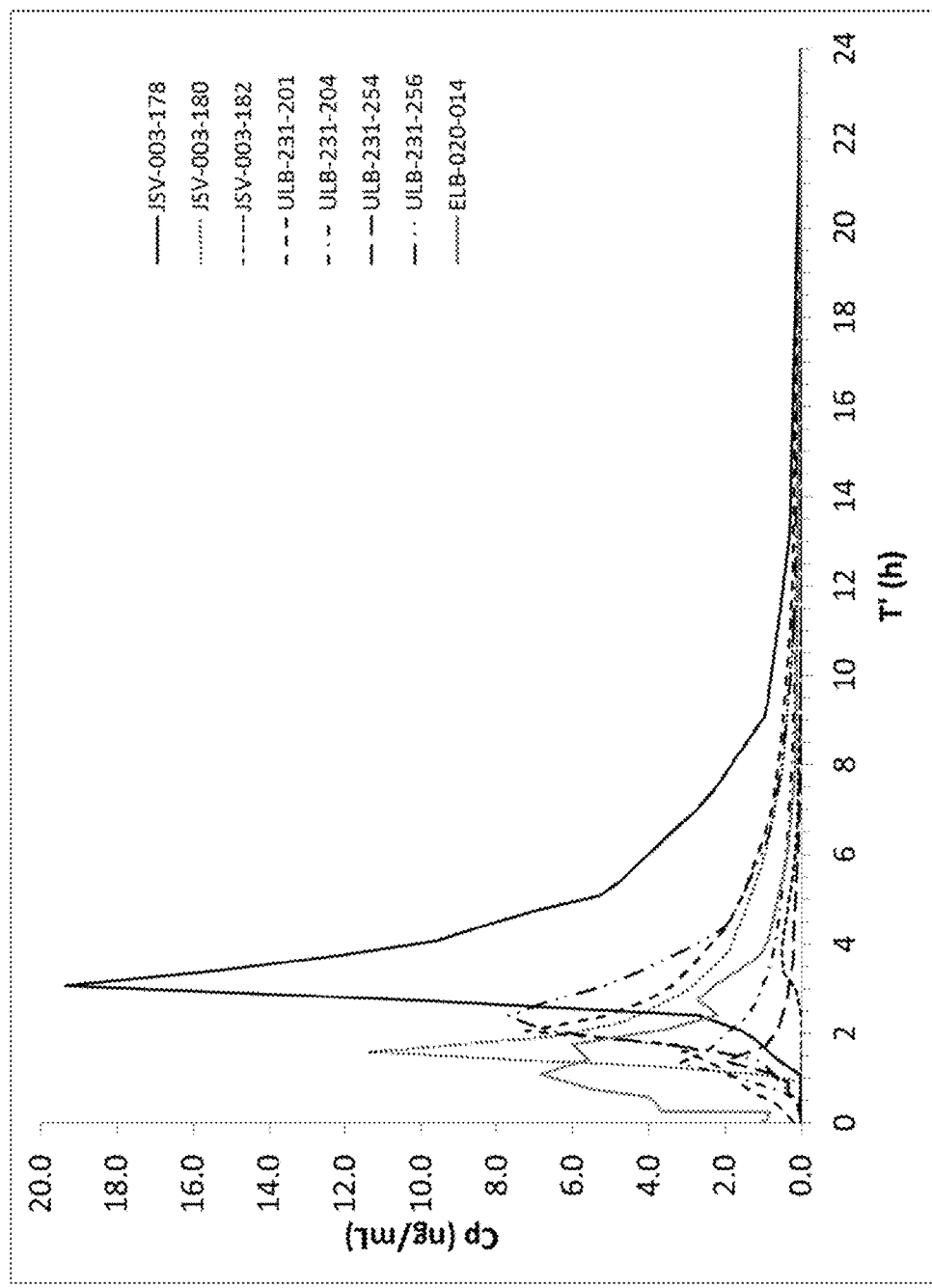

The average curves for PO doses, corrected for $T_{max}$ are shown in FIGS. 25A and 25B.

Figure 26:
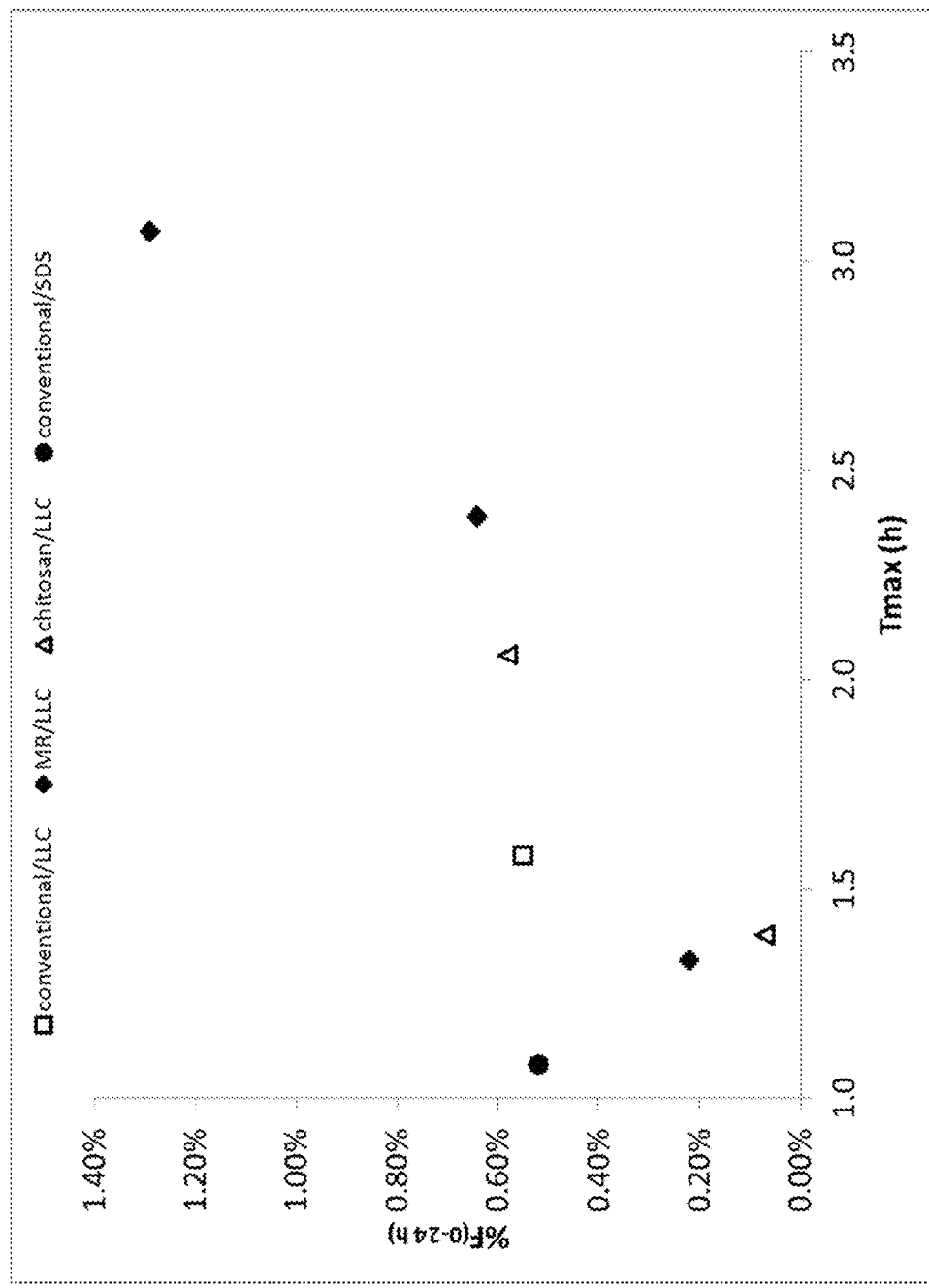
FIG. 26 shows the systemic bioavailability vs. $T_{max}$ "Conventional" denotes a core containing disintegrant, "MR" cores contain HPC or HPMC (no disintegrant), "chitosan" cores contain medium-weight chitosan (no disintegrant). Permeation enhancers were either LLC (lauroyl-L-carnitine) or SDS (sodium dodecyl sulfate).

FIG. 26 shows the bioavailability vs. $T_{max}$. "Conventional" denotes a core containing disintegrant, "Modified Release" or "MR" cores contain HPC or HPMC (and do not contain disintegrant), "chitosan" cores contain medium-weight chitosan (and do not disintegrant). Permeation enhancers were either LLC (lauroyl-L-carnitine) or SDS (sodium dodecyl sulfate). Note that % F increases as $T_{max}$ increases —contrary to the dosage forms with a conventional core and/or enteric coating having a faster, more immediate release.

Figure 27:
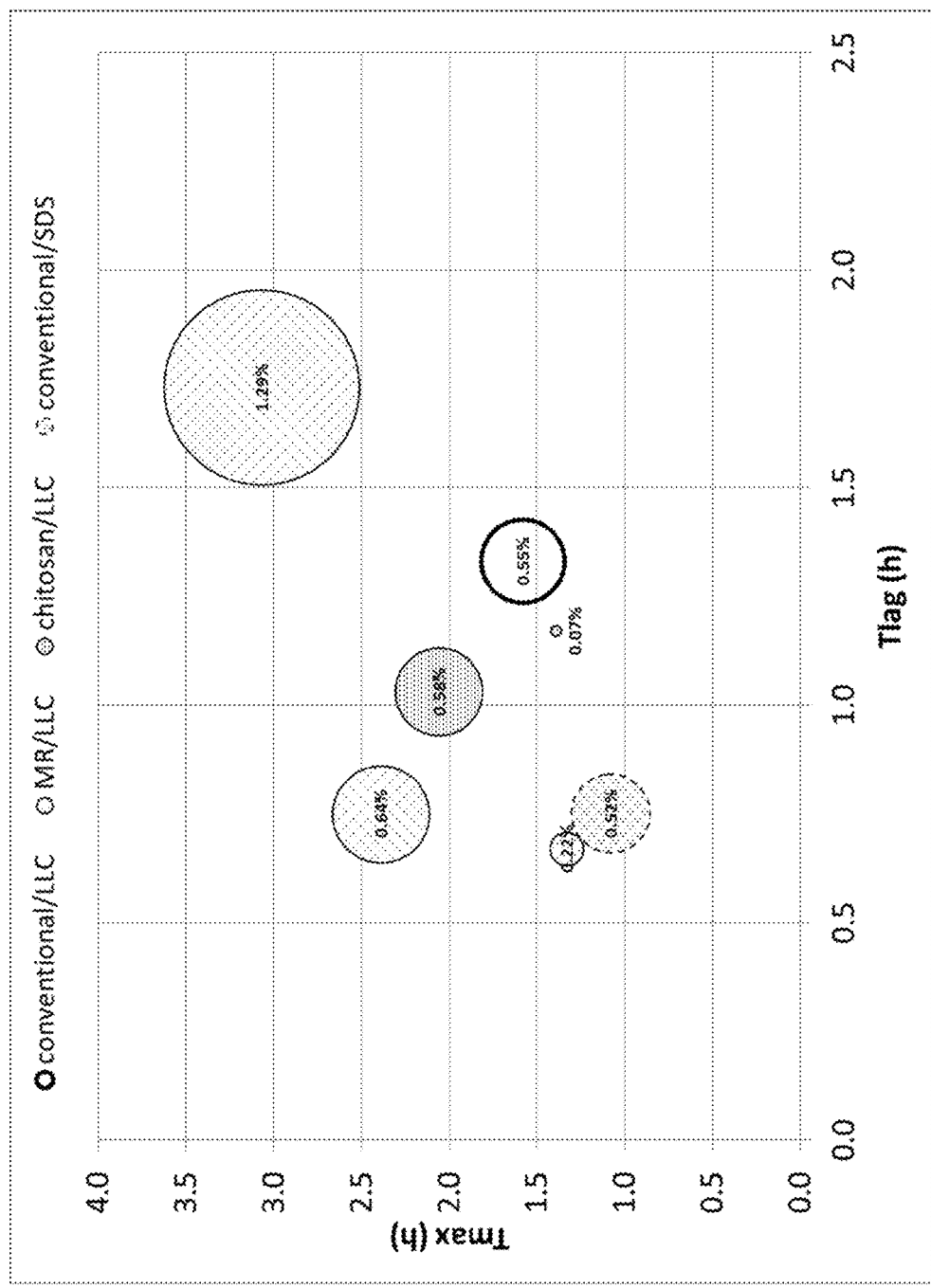
FIG. 27 is a bubble plot representation of the triptorelin data, showing $T_{max}$ versus $T_{lag}$. The size of the bubble corresponds to the absolute bioavailability (also labeled on the data points).

FIG. 27 is a bubble plot representation of the data, showing the influence of $T_{lag}$ and $T_{max}$ on % F. The size of the bubble corresponds to the value of % F (also labeled on the data points).

The conventional tablet with LLC (JSV-003-180, see U.S Pat. No. 8,377,863, which is incorporated by reference herein in its entirety) is the baseline comparison for all formulations containing LLC. This formulation contains a super-disintegrant; thus, the tablet core disintegrates in solution. In contrast, the MR cores (JSV-003-178, ULB-231-204, and ULB-231-256) and chitosan cores (ULB-231-201 and ULB-231-254) do not contain a super-disintegrant. These cores do not disintegrate in solution, but instead form a viscous hydrogel that slowly erodes.

The chitosan cores demonstrate the advantage of a delayed $T_{max}$. The data for batch ULB-231-254 show a relatively early $T_{lag}$ and $T_{max}$ (vs. JSV-003-180), which results in poor bioavailability. However, despite having a slightly earlier $T_{lag}$ (than the aforementioned batches), batch ULB-231-201 has a longer $T_{max}$ than both ULB-231-254 and JSV-003-180. This results in an 8-fold increase in % F for ULB-231-201 vs. ULB-231-254.

The MR cores also show that longer $T_{lag}$ and $T_{max}$ result in increased % F. Batch ULB-231-204 has both $T_{lag}$ and $T_{max}$ sooner than JSV-003-180, and lower bioavailability. By increasing $T_{lag}$ and $T_{max}$, batch ULB-231-256, there is a 3-fold increase in % F over batch ULB-231-204. In batch JSV-003-178, both $T_{lag}$ and $T_{max}$ are again increased, resulting in an additional 2-fold increase in % F (vs. ULB-231-256), or an overall 6-fold increase vs. ULB-231-204, or an overall 2.3-fold increase over the conventional formulation JSV-003-180.

The conventional core with SDS (batch ELB-020-014, which contains a super-disintegrant) shows that, for relatively early $T_{lag}$ and $T_{max}$ (compared to "conventional/LLC" JSV-003-180), a much more potent surfactant (having a higher CMC) than LLC can be used to achieve a similar % F. In this case, the CMC for SDS is about 10 mM, compared to about 1.2 mM for LLC.

The data show, within a formulation and across different formulations, that the bioavailability of the peptide (e.g. triptorelin) can be modulated by controlling the $T_{lag}$ and $T_{max}$ of the dosage form. A longer $T_{lag}$ can be achieved by increasing the thickness or buffer capacity of the enteric coat. A longer $T_{max}$ can be achieved by increasing the viscosity of the tablet core through the use of viscous fillers (HPC, HPMC, chitosan) in the absence of a super-disintegrant. Together, longer $T_{lag}$ and $T_{max}$ results in greater systemic bioavailability, in general.

In addition, the data show that the fine-tuning of these parameters can further augment systemic bioavailability. For example, in the case of the "MR/LLC" formulations, an increase in $T_{lag}$ achieved by increased enteric coat buffer capacity (JSV-003-178) increased bioavailability, despite only slightly increasing $T_{max}$ (compared to the "MR/LLC" formulation, ULB-231-256). Both of these batches perform better than ULB-231-204, which has the shortest $T_{lag}$ and $T_{max}$ of the three.

In the case of the "conventional" tablet core ELB-020-014, where $T_{lag}$ and $T_{max}$ were relatively short compared to the conventional core JSV-003-180, bioavailability can be enhanced by using a permeation enhancer with a greater CMC. In this case, substitution of LLC with SDS was able to achieve comparable bioavailability, despite the small values of $T_{lag}$ and $T_{max}$.

$T_{max}$ can be increased by slowing the dissolution of the tablet core, which can be done a number of ways through the core formulation. For example, a core composed of HPC or HPMC without disintegrant ("MR") can take longer to completely dissolve than a conventional core.

Based on these data, it is believed that that a tablet containing a pharmaceutical active ingredient (e.g. peptide), pH-lowering agent, and permeation enhancer, systemic bioavailability can be increased through a combination of:

1. Increasing the $T_{lag}$ (the time delay between oral dose administration and the first measurable concentration of the API in systemic circulation).
2. Increasing $T_{max}$ —the time at which the maximum concentration of API ($C_{max}$) is in systemic circulation.
3. Increasing the surfactant strength of the permeation enhancer.

Where (1) can be achieved by increasing the thickness or buffer capacity of the enteric coat, (2) can be achieved by increasing the viscosity of the tablet core, and (3) can be achieved by substituting a permeation enhancer for another with a higher CMC (e.g. of about 1.0 to about 40 mM).

Example 3

One of ordinary skill in the art would reasonable expect that additional active agents described herein (i.e. various peptides or their prodrugs, such as esters or salts, and small molecules) would achieve a targeted delivery and increased bioavailability when in administered in a dosage form as disclosed herein. Without being bound by the theory, it is believed that the further delaying $T_{lag}$ and $T_{max}$, the further the bioavailability increases. This can be achieved by changing the composition of the enteric coat to include mixtures of the polymers listed in Table 9 below.

TABLE 9

| Polymer | Dissolution Properties |
| --- | --- |
| EUDRAGIT ® L 30 D-55 | Dissolution above pH 5.5 |
| EUDRAGIT ® L 100-55 | |
| EUDRAGIT ® L 100 | Dissolution above pH 6.0 |
| EUDRAGIT ® L 12,5 | |
| EUDRAGIT ® S 100 | Dissolution above pH 7.0 |
| EUDRAGIT ® S 12,5 | |
| EUDRAGIT ® FS 30 D | |

Combinations of these polymers can result in different dissolution properties due to changes in the plasticity and dissolution pH of the mixtures. The pH of the intestine increases from ~5.5 in the duodenum to ~7 in the ileum, with intermediate values in the jejunum. Thus, $T_{lag}$ can be increased by using an enteric coat that dissolves at a pH between 5.5 and 7, due to longer intestinal transit time prior to dissolution of the coat.

Selected Eudragit® compositions are known to dissolve at different pH values ranging from pH 5.5 up to pH 7. Depending on the selected Eudragit® compositions, such coatings are suitable to avoid the acidic environment of the stomach and duodenum and to maximize the initial dissolution at a pH>5.5 of duodenal and jejunal fluid.

It is understood that the examples and embodiments described herein are for illustrative purposes only and that various modifications of changes in light thereof are to be included within the spirit and purview of this application and scope of the appended claims. All publication, patents and patent applications cited herein are hereby incorporated by reference in their entirety for all purposes.

The invention claimed is:

1. A modified release solid oral composition comprising:
   (a) a core comprising: (i) an effective amount of active pharmaceutical ingredient, wherein the active pharmaceutical ingredient is a peptide, a peptidomimetic, a small molecule, or a combination thereof, (ii) coated acid particles, wherein the acid particles are coated with a water soluble coat and wherein the acid of the coated acid particles is a pH lowering agent, (iii) an absorption enhancer, (iv) a filler comprising a hydrogel-forming polymer, wherein a 2% solution of the hydrogel-forming polymer has a viscosity between 3,000 to 120,000 cP at 20° C., and (v) less than 0.01% by weight of disintegrant, wherein the active pharmaceutical ingredient, the coated acid particles, the absorption enhancer, the filler and the less than 0.01% disintegrant are intermixed; and
   (b) about 5 mg/cm$^2$ to about 25 mg/cm$^2$ of an enteric coating surrounding the core, wherein the composition provides a pharmacokinetic profile of the active pharmaceutical ingredient with a $T_{lag}$ greater than 1.0 h and less than 16 h post-administration and a $T_{max}$ greater than ($T_{lag}$+0.5 h) and less than 20 h post-administration;
   wherein, if the composition was added to ten milliliters of 0.1 M aqueous sodium bicarbonate solution, the pH of the solution would be lowered to no higher than 5.5.

2. The composition of claim 1 further comprising a water soluble barrier beneath the enteric coating.

3. The composition of claim 1 wherein the absorption enhancer has a critical micelle concentration of from about 1.0 mM to about 40 mM.

4. The composition of claim 1 wherein the filler comprises microcrystalline cellulose, hydroxypropylcellulose, hydroxypropylmethylcellulose, chitosan or a combination thereof.

5. The composition of claim 1 wherein the absorption enhancer comprises a cationic surface active agent, an anionic surface active agent or a combination thereof.

6. The composition of claim 1 wherein the coated acid particles comprises citric acid, tartaric acid or a combination thereof.

7. The composition of claim 1 comprising from about 50 mg to about 500 mg of coated acid particles.

8. The composition of claim 1, wherein the peptide is one of leuprolide, insulin, vasopressin, calcitonin, calcitonin gene-related peptide, parathyroid hormone, desmopressin, gonadotrophin releasing hormone (GnRH), luteinizing hormone-releasing factor, erythropoietin, tissue plasminogen activators, human growth hormone, adrenocorticotropin, interleukins, enkephalin, glucagon-like peptide-1, desmopressin, or 2,6-dimethyltyrosine-D-arginine-phenylalanine-lysine amide.

9. The composition of claim 1, wherein the small molecule is classified as BCS Class II, BCS Class III or BCS Class IV.

10. The composition of claim 9 wherein the small molecule is one of tigecycline, zanamivir, kanamycin, tobramycin, or fenofibrate.

11. The composition of claim 2 wherein the water soluble barrier is in amount from about 6% to about 15% by weight.

12. The composition of claim 1 wherein the pharmacokinetic release profile targets release of the pharmaceutical active ingredient to the jejunum, the ileum or the jejunum and the ileum.

13. The composition of claim 1, wherein the coated acid particles comprise citric acid, tartaric acid or a combination thereof.

14. The composition of claim 13, wherein the water soluble coat separates the acid from the active pharmaceutical ingredient.

15. A modified release solid oral composition comprising:
   (a) a core comprising: (i) an effective amount of active pharmaceutical ingredient, wherein the active pharmaceutical ingredient is a peptide, a peptidomimetic, a small molecule, or a combination thereof, (ii) coated acid particles, wherein the acid particles are coated with a water soluble coat and wherein the acid of the coated acid particles is a pH lowering agent, (iii) an absorption enhancer, (iv) a filler comprising a hydrogel-forming polymer, wherein a 2% solution of the hydrogel-forming polymer has a viscosity between 3,000 to 120,000 cP at 20° C., wherein the core is free of disintegrant, wherein the active pharmaceutical ingredient, the coated acid particles, the absorption enhancer, and the filler are intermixed; and
   (b) about 5 mg/cm$^2$ to about 25 mg/cm$^2$ of an enteric coating surrounding the core, wherein the composition provides a pharmacokinetic profile of the active pharmaceutical ingredient with a $T_{lag}$ greater than 1.0 h and less than 16 h post-administration and a $T_{max}$ greater than ($T_{lag}$+0.5 h) and less than 20 h post-administration;
   wherein, if the composition was added to ten milliliters of 0.1 M aqueous sodium bicarbonate solution, the pH of the solution would be lowered to no higher than 5.5.

16. A method of treating a patient comprising (a) providing a solid oral dosage form comprising (i) a core comprising: an effective amount of active pharmaceutical ingredient, wherein the active pharmaceutical ingredient is a peptide, a peptidomimetic, a small molecule, or a combination thereof, coated acid particles, wherein the acid particles are coated with a water soluble coat and wherein the acid of the coated acid particles is a pH lowering agent, an absorption enhancer, a filler comprising a hydrogel-forming polymer, wherein a 2% solution of the hydrogel-forming polymer has a viscosity between 3,000 to 120,000 cP at 20° C., and less than 0.01% by weight of disintegrant, wherein the active pharmaceutical ingredient, the coated acid particles, the absorption enhancer, the filler and the less than 0.01% disintegrant are intermixed; and (ii) about 5 mg/cm$^2$ to about 25 mg/cm$^2$ of an enteric coating surrounding the core; (b) administering orally to a patient, the solid oral dosage form, wherein the composition provides a pharmacokinetic profile of the active pharmaceutical ingredient with a $T_{lag}$ greater than 1.0 h and less than 16 h post-administration and a $T_{max}$ greater than ($T_{lag}$+0.5 h) and less than 20 h post-administration;

wherein, if the composition was added to ten milliliters of 0.1 M aqueous sodium bicarbonate solution, the pH of the solution would be lowered to no higher than 5.5.

17. The method of claim 16 wherein the pharmacokinetic profile targets release of the pharmaceutical active ingredient to the jejunum, the ileum or the jejunum and the ileum.

* * * * *